US012606597B2

(12) United States Patent
Møller et al.

(10) Patent No.: US 12,606,597 B2
(45) Date of Patent: Apr. 21, 2026

(54) **VACCINES TARGETING *PSEUDOMONAS AERUGINOSA***

(71) Applicant: Evaxion Biotech A/S, Hørsholm (DK)

(72) Inventors: Niels Iversen Møller, Hørsholm (DK); Andreas Holm Mattsson, Hørsholm (DK)

(73) Assignee: Evaxion Biotech A/S, Horsholm (DK)

( * ) Notice: Subject to any disclaimer, the term of this patent is extended or adjusted under 35 U.S.C. 154(b) by 238 days.

(21) Appl. No.: 18/340,479

(22) Filed: Jun. 23, 2023

(65) Prior Publication Data

US 2024/0076325 A1 Mar. 7, 2024

Related U.S. Application Data

(62) Division of application No. 16/473,443, filed as application No. PCT/EP2018/050226 on Jan. 5, 2018, now Pat. No. 11,718,648.

(30) Foreign Application Priority Data

Jan. 5, 2017 (EP) ..................................... 17150419

(51) Int. Cl.

| | |
|---|---|
| *C07K 14/21* | (2006.01) |
| *A61K 39/00* | (2006.01) |
| *A61K 39/104* | (2006.01) |
| *A61P 31/04* | (2006.01) |
| *C07K 14/33* | (2006.01) |
| *C07K 14/34* | (2006.01) |
| *C07K 14/435* | (2006.01) |
| *C07K 16/12* | (2006.01) |
| *C07K 16/1214* | (2026.01) |
| *C12Q 1/689* | (2018.01) |
| *G01N 33/569* | (2006.01) |

(52) U.S. Cl.
CPC ............ *C07K 14/21* (2013.01); *A61K 39/104* (2013.01); *A61P 31/04* (2018.01); *C07K 14/33* (2013.01); *C07K 14/34* (2013.01); *C07K 14/43504* (2013.01); *C07K 16/1214* (2013.01); *C12Q 1/689* (2013.01); *G01N 33/56911* (2013.01); *A61K 2039/505* (2013.01); *A61K 2039/55505* (2013.01); *A61K 2039/6037* (2013.01); *A61K 2039/6081* (2013.01); *A61K 2039/627* (2013.01)

(58) Field of Classification Search
CPC .................................. C07K 14/21; A61P 31/04
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,684,611 A | 8/1987 | Schilperoot et al. |
| 4,800,159 A | 1/1989 | Mullis et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,843,650 A | 12/1998 | Segev |
| 5,846,709 A | 12/1998 | Segev |
| 5,846,783 A | 12/1998 | Wu et al. |
| 5,849,497 A | 12/1998 | Steinman |
| 5,849,546 A | 12/1998 | Sousa et al. |
| 5,849,547 A | 12/1998 | Cleuziat et al. |
| 5,858,652 A | 1/1999 | Laffler et al. |
| 5,866,366 A | 2/1999 | Kallender |
| 5,871,986 A | 2/1999 | Boyce |
| 5,916,776 A | 6/1999 | Kumar |
| 5,922,574 A | 7/1999 | Minter |
| 5,928,905 A | 7/1999 | Stemmer et al. |
| 5,928,906 A | 7/1999 | Koster et al. |
| 5,932,451 A | 8/1999 | Wang et al. |

(Continued)

FOREIGN PATENT DOCUMENTS

| | | |
|---|---|---|
| EP | 0297291 | 1/1989 |
| EP | 0357024 | 3/1990 |

(Continued)

OTHER PUBLICATIONS

Stover et al., Nature, 2000; 406: 959-964 (Year: 2000).*
Skolnick et al., Trends in Biotechnology 18: 34-39, 2000 (Year: 2000).*
Ellis, Vaccines, W.B. Saunders Company, Chapter 29, 1988, pp. 568-574 (Year: 1988).*
Boslego et al., Vaccines and Immunotherapy, 1991, Chapter 17 (Year: 1991).*
Colman, Res. Immunology, Jan. 1994, vol. 145, pp. 33-36 (Year: 1994).*

(Continued)

*Primary Examiner* — Brian Gangle
*Assistant Examiner* — Lakia J Jackson-Tongue
(74) *Attorney, Agent, or Firm* — McHale & Slavin, P.A.

(57) ABSTRACT

Immunogenic proteins from *Pseudomonas aeruginosa* as well as nucleic acids, vectors and transformed cells useful for expression of the proteins. Also disclosed are methods for prophylaxis of infection with *Pseudomonas aeruginosa* using the proteins, nucleic acids, vectors or transformed cell.

12 Claims, 9 Drawing Sheets

Figure 2:
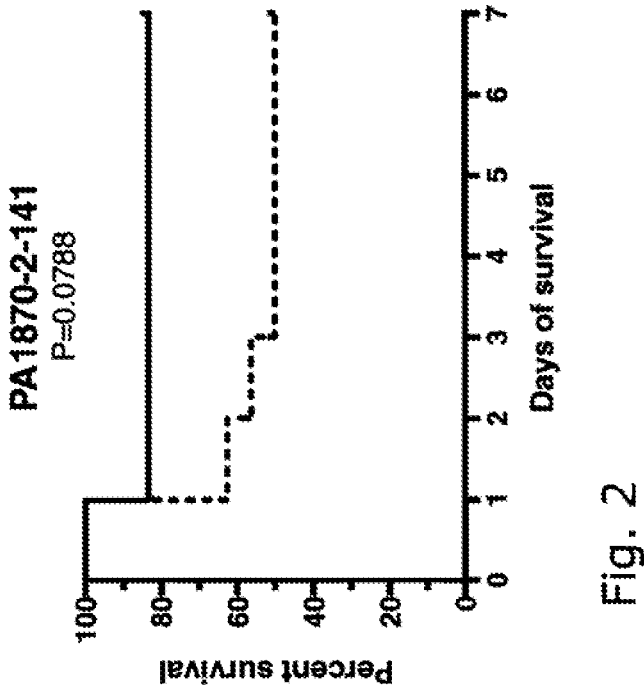

Specification includes a Sequence Listing.

(56) References Cited

U.S. PATENT DOCUMENTS

| | | | |
|---|---|---|---|
| 5,935,825 | A | 8/1999 | Nishimura et al. |
| 5,939,291 | A | 8/1999 | Loewy et al. |
| 5,942,391 | A | 8/1999 | Zhang et al. |
| 5,945,100 | A | 8/1999 | Fick |
| 5,981,274 | A | 11/1999 | Tyrrell et al. |
| 5,994,624 | A | 11/1999 | Trolinder et al. |
| 6,551,795 | B1 * | 4/2003 | Rubenfield ............ C07K 14/21 |
| | | | 435/6.15 |
| 2004/0029129 | A1 | 2/2004 | Wang et al. |
| 2007/0020624 | A1 | 1/2007 | Rubenfield et al. |

FOREIGN PATENT DOCUMENTS

| | | |
|---|---|---|
| EP | 2192172 | 6/2010 |
| EP | 1769068 | 12/2014 |
| EP | 2853599 | 4/2015 |
| GB | 2202328 | 9/1988 |
| WO | WO9014837 | 12/1990 |
| WO | WO9409699 | 5/1994 |
| WO | WO9506128 | 3/1995 |
| WO | WO9820734 | 5/1998 |
| WO | WO2002077183 | 10/2002 |
| WO | WO2005081905 | 9/2005 |
| WO | WO2011125015 | 10/2011 |
| WO | WO2015189422 | 12/2015 |
| WO | WO2017005670 | 1/2017 |
| WO | WO2018127545 | 7/2018 |

OTHER PUBLICATIONS

Petersen, B. et al, "A generic method for assignment of reliability scores applied to solvent accessibility predictions", BMC Structural Biology, vol. 9:51, pp. 1-10, (Jul. 2009).

Larsen, J. et al, "Improved method for predicting linear B-cell epitopes", Internet article: http://www.Immunome-Research.com/content/2/1/2, BioMed Central, vol. 2:2, pp. 1-7, (Apr. 2006).

Petersen, B. et al, "NetTurnP-neural network prediction of Beta-turns by use of evolutionary information and predicted protein sequence features", PlosOne, vol. 5:11:e15079, pp. 1-9, (Nov. 2010).

Kohler, G. et al, "Continuous cultures of fused cells secreting antibody of predefined specificity", Nature, vol. 256, pp. 495-497, (1975).

Robinson, H. et al, "DNA vaccines", Seminars in Immunology, vol. 9:5, pp. 271-283, (Nov. 1997).

Donnelly, J. et al, "DNA Vaccines" Annual eview of Immunology, vol. 15, pp. 617-648, (Apr. 1997).

Stover, C. et al, "Complete genome sequence of pseudomonas aeruginosa PAO1, an opposite pathogen", Nature, vol. 406, pp. 959-964, (Aug. 2000).

Skolnick, J. et al, "From genes to protein structure and function: novel applications of computational approaches in the genomic era", Tibtech, vol. 18, pp. pp. 34-39, (Jan. 2000).

Nishat, S. et al, "Entirely carbohydrate-based vaccines: an emerging field for specific and selective immune responses", Vaccines, vol. 4(19), pp. 1-16, (2016).

Harris, J. et al, "Keyhole limpet hemocyanin (KLH): a biomedical review", Micron, vol. 30, pp. 597-623, (1999).

Campbell, A., "Monoclonal antibody technology", Elsevier, Department of Biochemistry, University of Glasgow, Great Britain, vol. 13(1), pp. 1-18, (1984).

Boslego, J. et al, "Gonorrhea vaccines", Ch. 17, p. 1, Best Available Copy, (1988).

Ellis, R., "New technologies for making vaccines", Vaccines, W. B. Saunders Company, Chapter 29, pp. 568-575, (1991).

Brady, C. et al, "Carrier protein outsourcing", BioProcess International, pp. 1-9, (Nov. 2012).

Gupta, R. et al, "Pharmaceutical biotechnology", Plenum Press, New York, vol. 6, pp. 229-248, (1995).

Gourley, L. et al., "Why is a protective antigen protective?", Human Vaccines, vol. 5(12), pp. 272-875, (Dec. 2009).

Lee, D. et al., "Genomic analysis reveals that pseudomonas aeruginosa virulence is combinatorial", Genome Biology, vol. 7(R90), pp. 1-15, (2006).

* cited by examiner

VACCINES TARGETING *PSEUDOMONAS AERUGINOSA*

CROSS-REFERENCE TO RELATED APPLICATIONS

In accordance with 37 C.F.R. 1.76, a claim of priority is included in an Application Data Sheet filed concurrently herewith. Accordingly, the present invention claims priority as a divisional of U.S. patent application Ser. No. 16/473, 443, entitled "VACCINES TARGETING *PSEUDOMONAS AERUGINOSA*", filed Jun. 25, 2019, which is a § 371 national stage entry of International Application No. PCT/EP2018/050226, entitled "VACCINES TARGETING *PSEUDOMONAS AERUGINOSA*", filed Jan. 5, 2018, which claims priority to European Patent Application No. 17150419.4, entitled "VACCINES TARGETING *PSEUDOMONAS AERUGINOSA*", filed Jan. 5, 2017, the entire contents of which are incorporated herein by reference.

FIELD OF THE INVENTION

The present invention relates to the field of antimicrobial prophylaxis and therapy. In particular the present invention relates to novel proteins and polynucleotides derived from *Pseudomonas aeruginosa*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

*Pseudomonas aeruginosa* is an opportunistic gram-negative pathogen. It represents a major course of hospital-acquired infections, especially in burnt and other immuno-compromised patients, including transplant or cancer patients. Therefore, it is regarded as a "problem microbe" in human medicine.

Many efforts have been made so far in order to develop a vaccine against *Pseudomonas aeruginosa*. For example, in the EP-0 297 291 the complete amino acid-sequence of the outer membrane protein F, as well as the nucleotide sequence coding for OprF is disclosed. In the EP-0 357 024 the complete amino acid sequence of the outer membrane protein I and, additionally, the nucleotide sequence coding for OprI is shown. Furthermore, with both proteins it was shown that they may be useful for conferring immunoprotection against *Pseudomonas aeruginosa* to an animal or human proband. However, improvement of procedures of vaccination against and treatment of a lethal *Pseudomonas aeruginosa* infection is still an object.

Vaccination is considered to be a very effective method of preventing infectious diseases in human and veterinary health care. Vaccination is the administration of immungenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immuno-protective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

Applicant's international patent application publication WO 2017/005570 (PCT/EP2016/065647) discloses 30 protein vaccine antigens as well as fragments and variants derived from *P. aeruginosa*. This patent application also discloses immunogens/vaccines derived from these and the nucleic acids that encode the 30 protein vaccine antigens and their fragments and variants.

OBJECT OF THE INVENTION

It is an object of embodiments of the invention to provide *Pseudomonas aeruginosa* derived antigenic polypeptides that may serve as constituents in vaccines against *Pseudomonas aeruginosa* infections and in diagnosis of *Pseudomonas aeruginosa* infections. It is also an object to provide nucleic adds, vectors, transformed cells, vaccine compositions, and other useful means for molecular cloning as well as for therapy and diagnosis with relevance for *Pseudomonas aeruginosa*.

SUMMARY OF THE INVENTION

It has been found by the present inventor(s) that *Pseudomonas aeruginosa* expresses a number of hitherto unknown putatively surface exposed proteins which are candidates as vaccine targets as well as candidates as immunizing agents for preparation of antibodies that target *Pseudomonas aeruginosa*.

So, in a first aspect the present invention relates to a polypeptide comprising
- a) an amino acid sequence selected from the group consisting of any one of SEQ ID NOs: 1-14, or
- b) an amino add sequence consisting of at least 5 contiguous amino add residues from any one of SEQ ID NOs: 1-14, or
- c) an amino acid sequence having a sequence identity of at east 60% with the amino acid sequence of a), d) an amino acid sequence having a sequence identity of at least 60% with the amino acid sequence of b), or e) an assembly of amino acids derived from any one of SEQ ID NOs: 1-14 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or ii) a nucleotide sequence consisting of any one of SEQ ID NOs: 31-90.

iii) a nucleotide sequence consisting of at least 10 consecutive nucleotides in any one of SEQ ID NOs: 31-90, iv) a nucleotide sequence having a sequence identity of east 60% with the nucleotide sequence in i) or ii), v) a nucleotide sequence having a sequence identity of at least 60% with the nucleotide sequence in iii), vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic add of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *Pseudomonas aeruginosa* in the animal.

In a seventh and eighth aspect, the invention relates to 1) a polyclonal antibody in which the antibodies specifically bind to at least one polypeptide of the invention, and which is essentially free from antibodies binding specifically to other *Pseudomonas aeruginosa* polypeptides, and to 2) an isolated monoclonal antibody or antibody analogue which binds specifically to a polypeptide of the invention. In a related ninth aspect, the invention relates to a pharmaceutical composition comprising such a polyclonal or monoclona antibody and a pharmaceutically acceptable carrier, vehicle or diluent.

In a $10^{th}$ aspect, the invention relates to a method for prophylaxis, treatment or amelioration of infection with *Pseudomonas aeruginosa*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *Pseudomonas aeruginosa*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *Pseudomonas aeruginosa* in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *Pseudomonas aeruginosa*, in particular the presence of a nucleic acid characteristic of *Pseudomonas aeruginosa*, in a sample, the method comprising contacting the sample with a nucleic acid fragment of the invention and detecting the presence of nucleic acid in the sample that hybridizes to said nucleic add fragment.

In a $14^{th}$ aspect, the invention relates to a method for the preparation of the polypeptide the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a $15^{th}$ aspect, the invention relates to a method for determining whether a substance, such as an antibody, is potentially useful for treating infection with *Pseudomonas aeruginosa*, the method comprising contacting the polypeptide of the invention with the substance and subsequently establishing whether the substance has at least one of the following characteristics:

1) the ability to bind specifically to said polypeptide, 2) the ability to compeed with said polypeptide for specific binding to a ligand/receptor, and 3) the ability to specifically inactivate said polypeptide.

Finally, in a $16^{th}$ aspect, the invention relates to a method for determining whether a substance, such as a nucleic acid, is potentially useful for treating infection with *Pseudomonas aeruginosa*, the method comprising contacting the substance with the nucleic acid fragment of claim of the invention and subsequently establishing whether the substance has either the ability to 1) bind specifically to the nucleic acid fragment, or 2) bind specifically to a nucleic acid that hybridizes specifically with the nucleic acid fragment.

LEGENDS OF THE FIGURES

Figure 1:
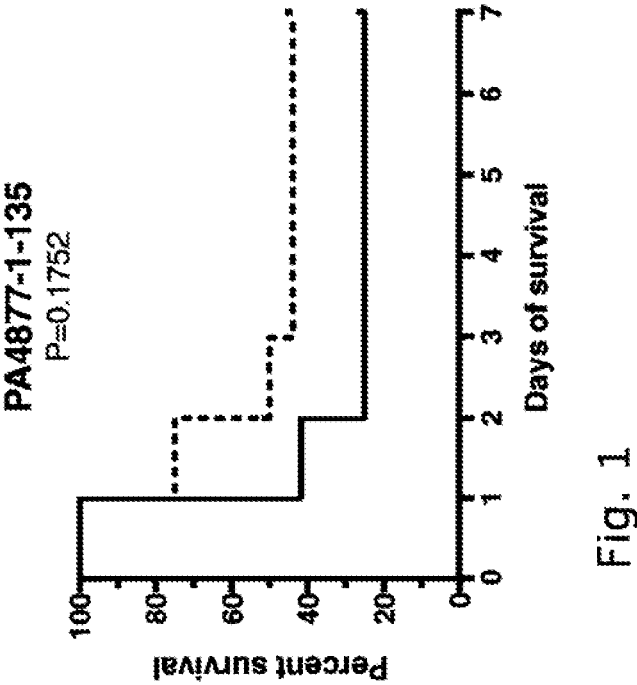
Figure 4:
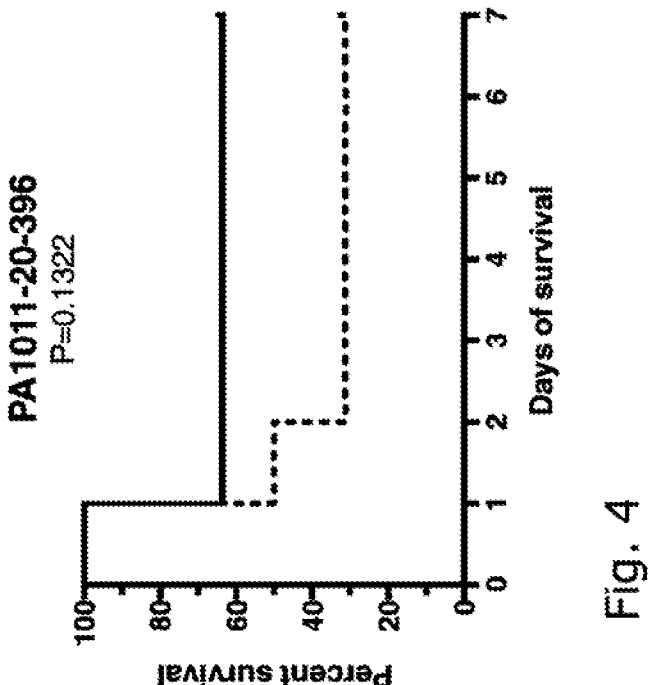
Figure 3:
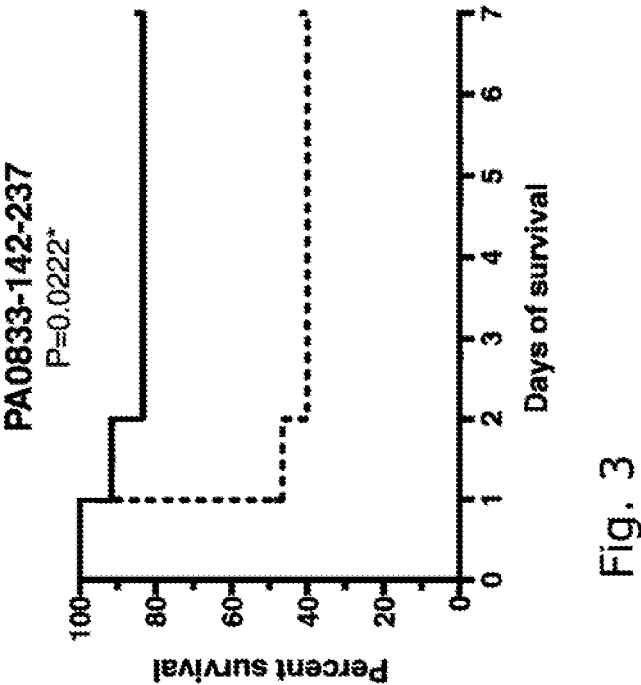
Figure 6:
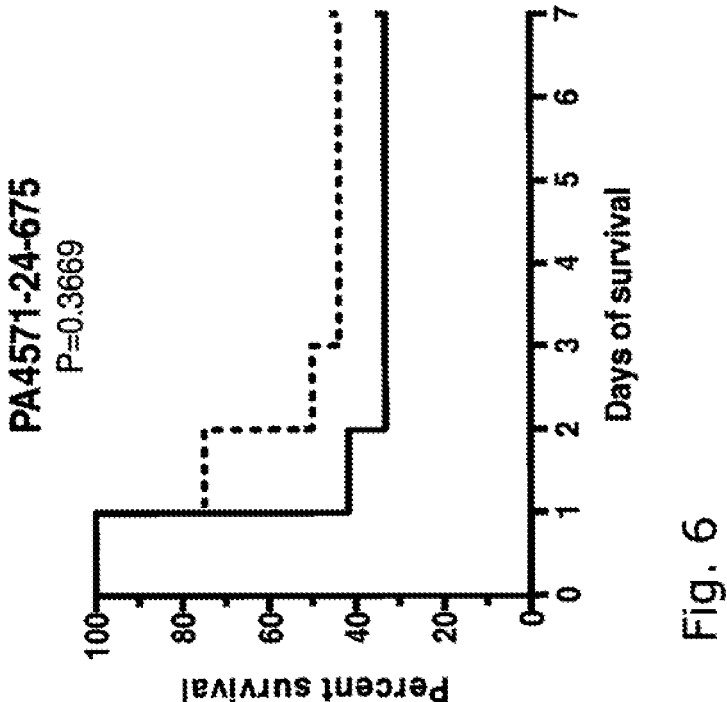
Figure 5:
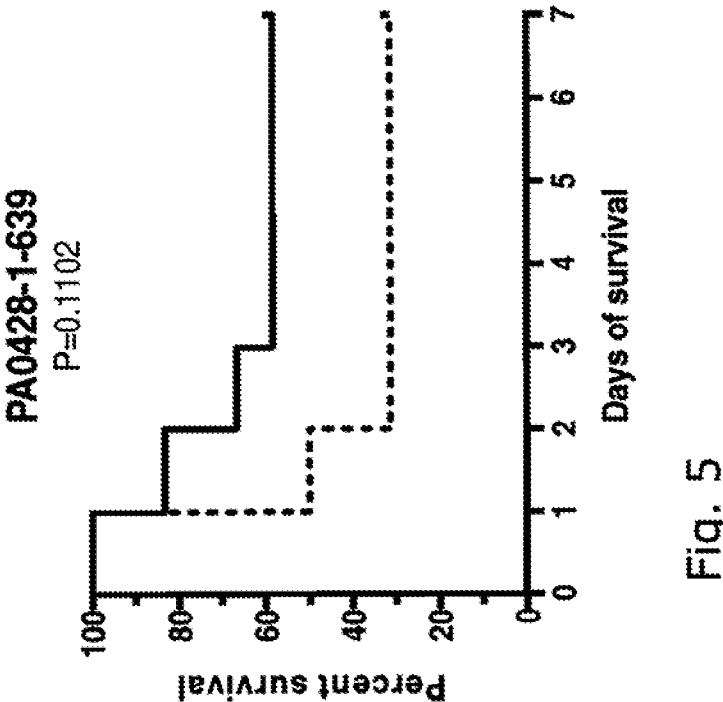
Figure 8:
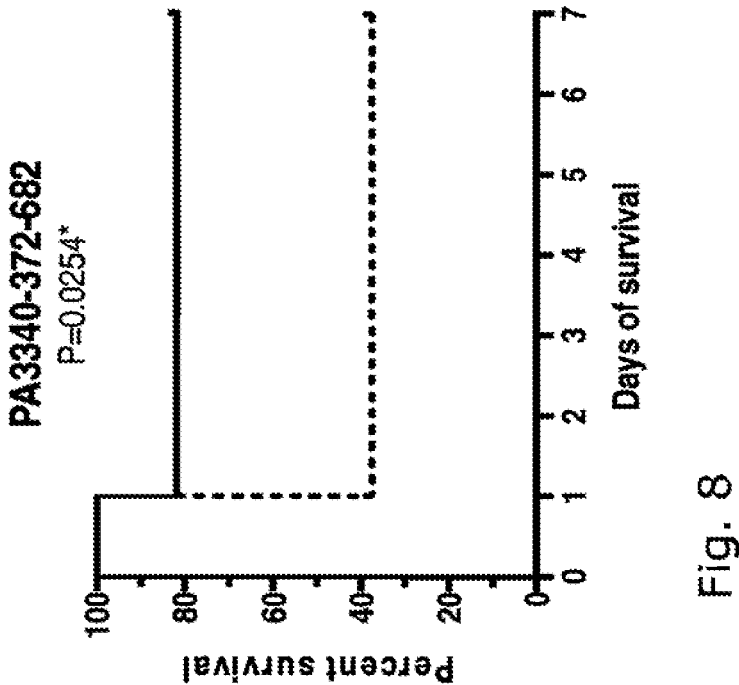
Figure 7:
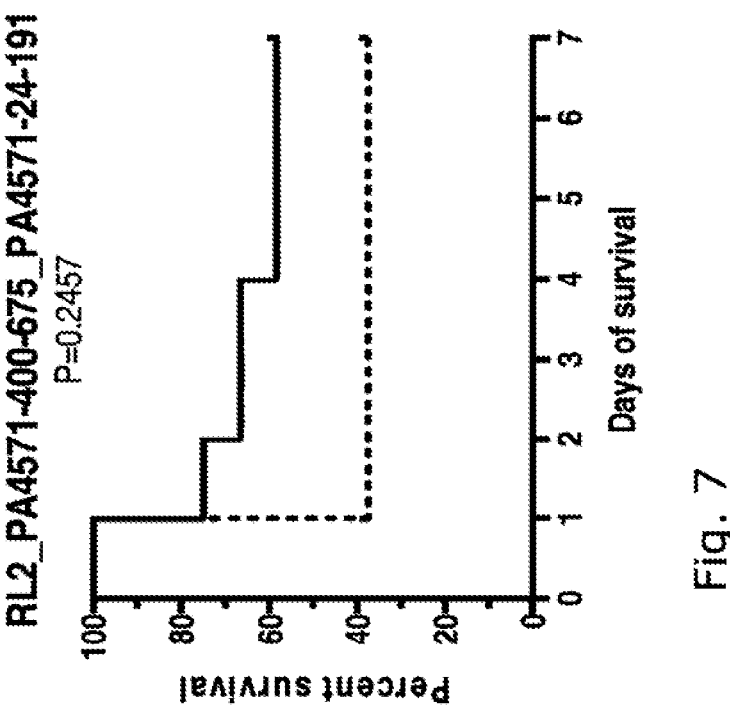
Figure 10:
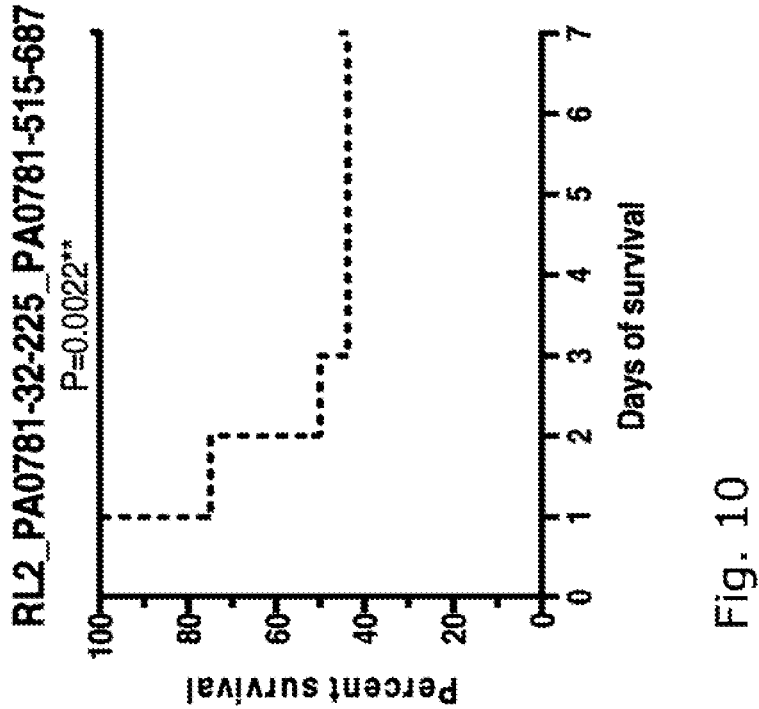
Figure 9:
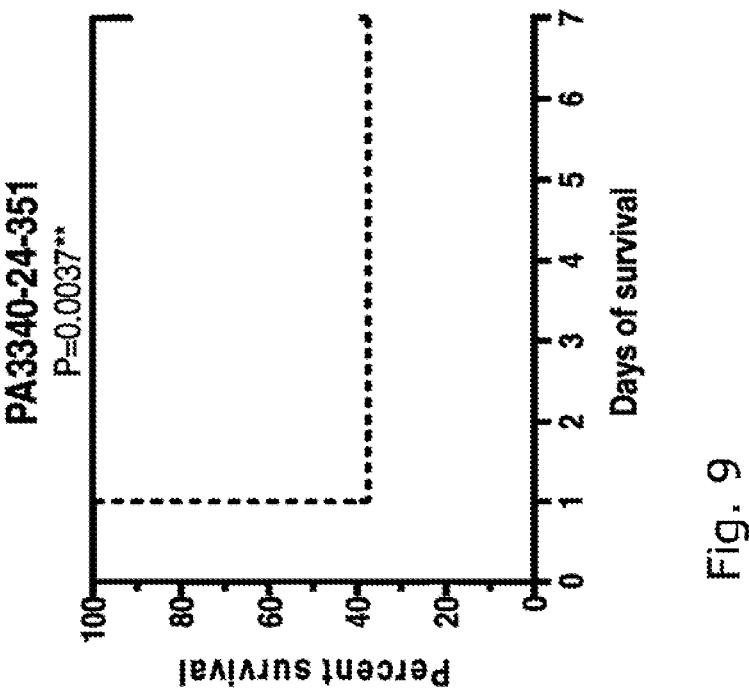
Figure 12:
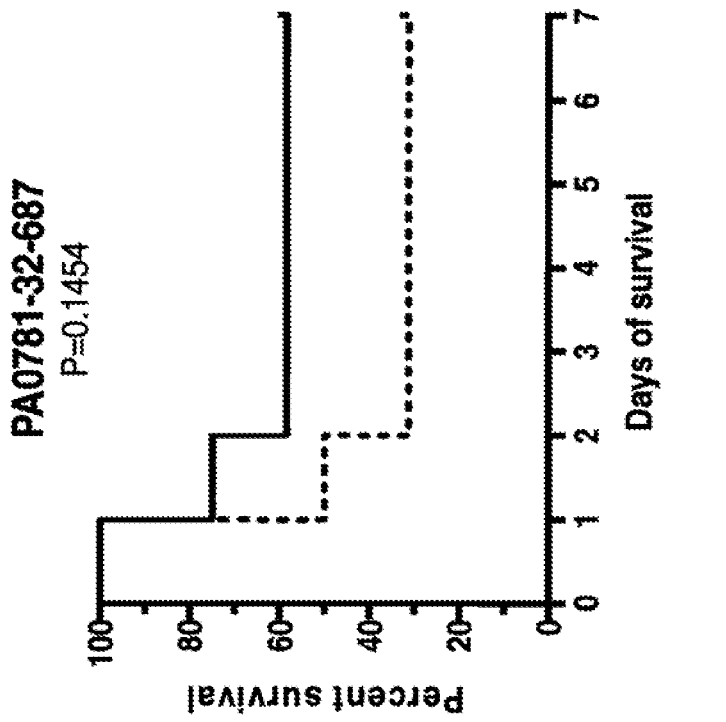
Figure 11:
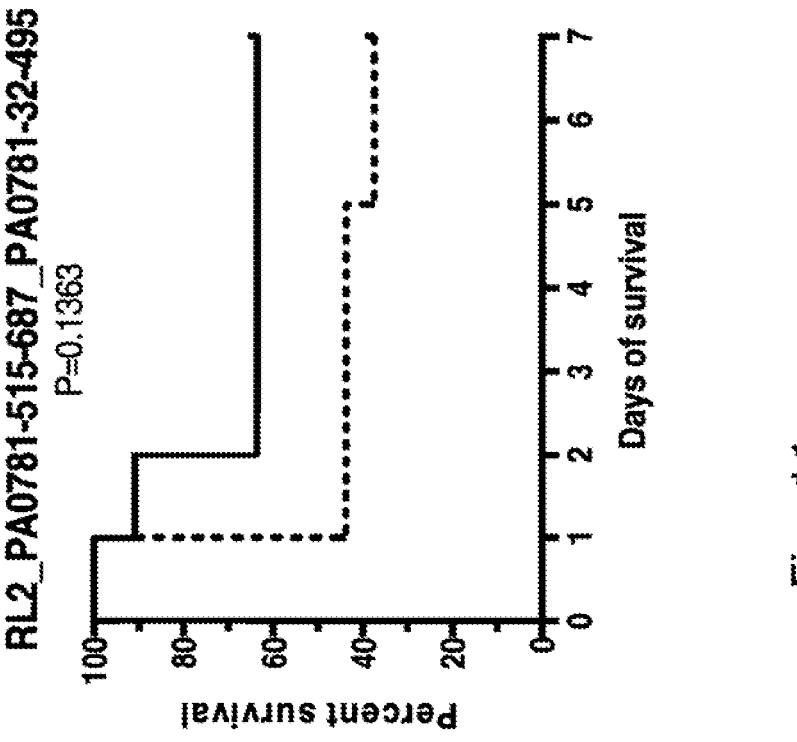
Figure 14:
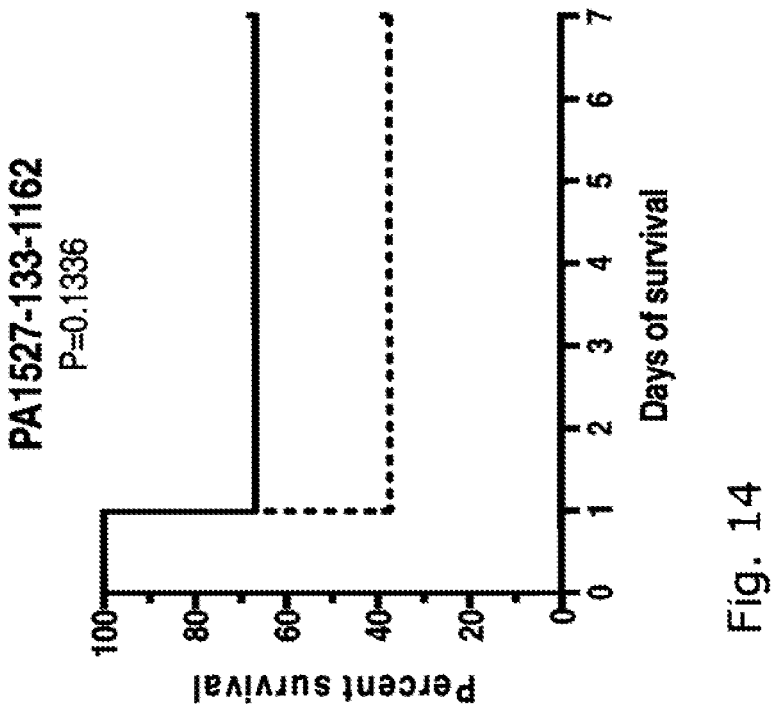
Figure 13:
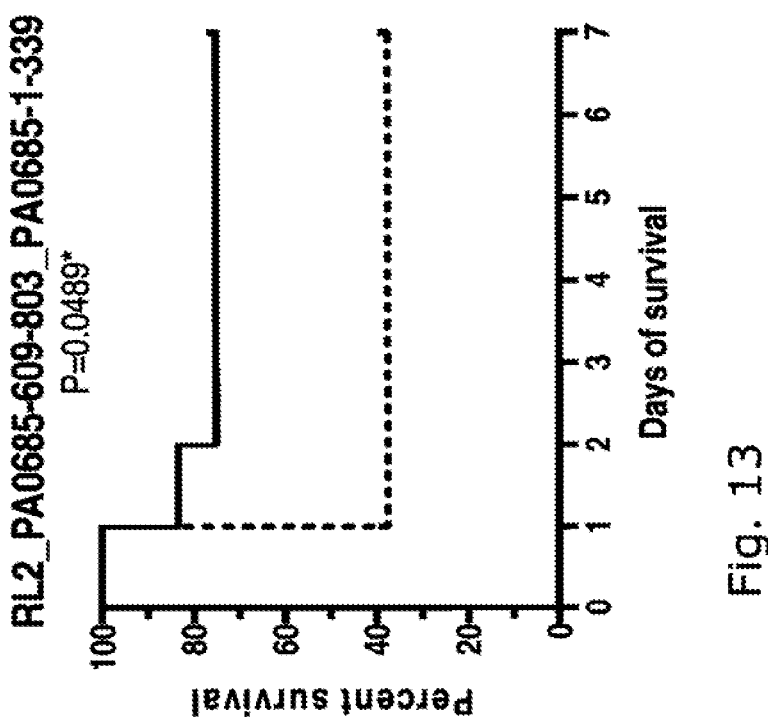
Figure 16:
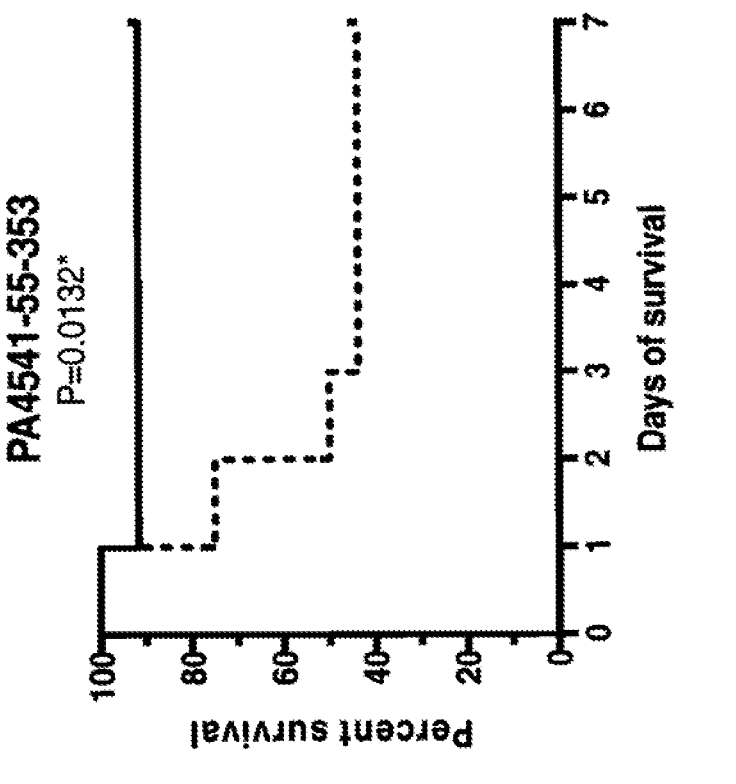
Figure 15:
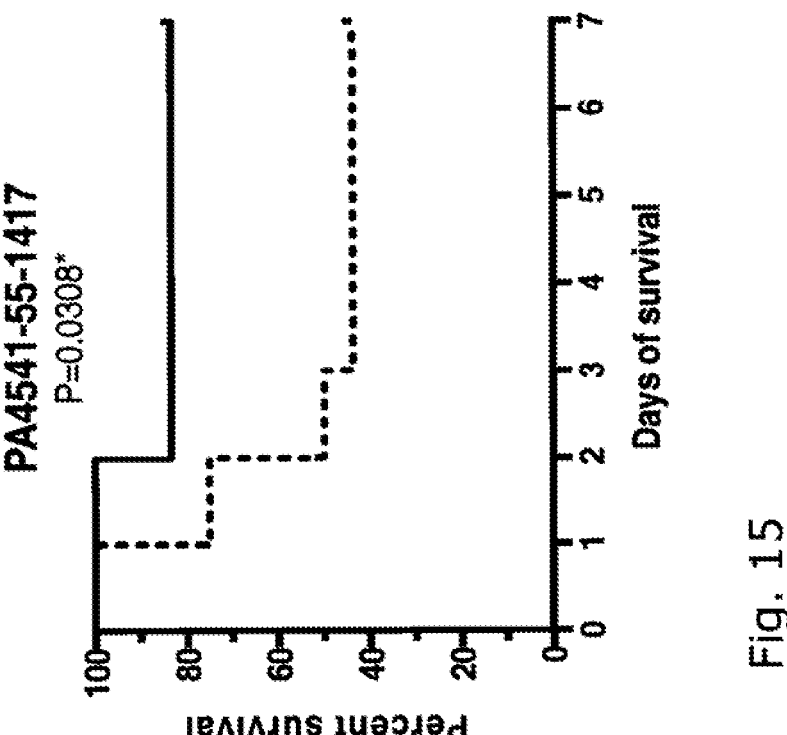
Figure 18:
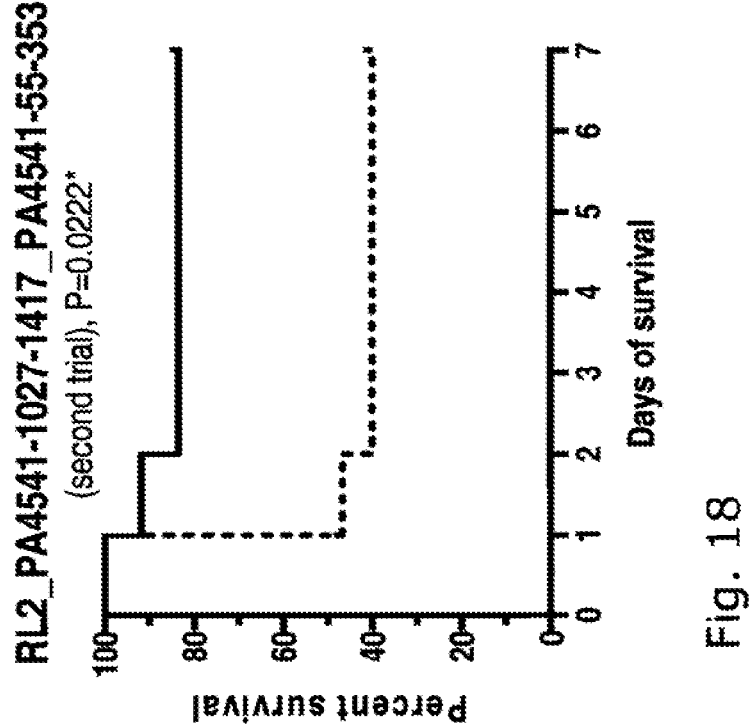
Figure 17:
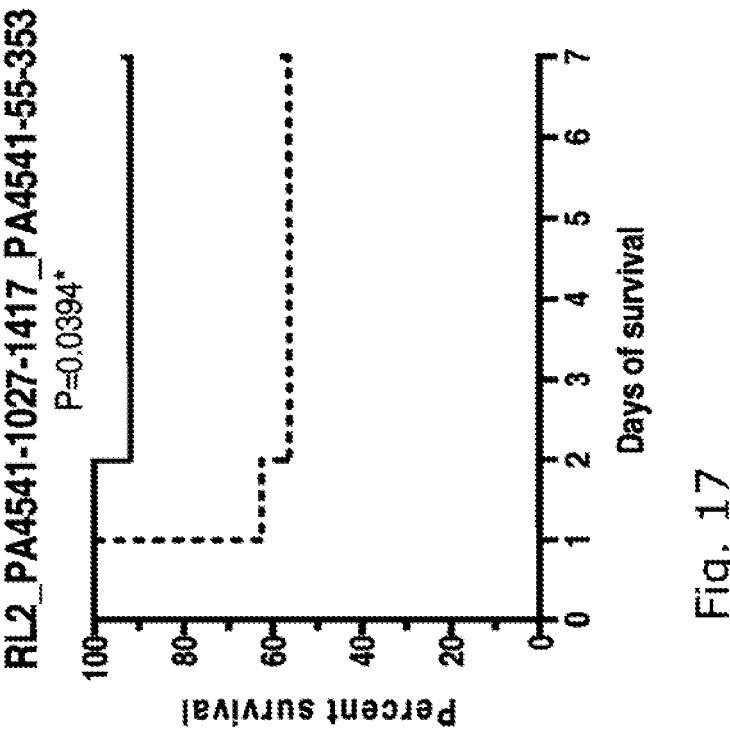

FIGS. 1-18; Effect of immunization with 17 different *P. aeruginosa* proteins on the survival of mice challenged with a lethal dose of *P. aeruginosa* PAO1.

FIGS. 1-18 show the survival curves of the protein-immunized mice (black line) and the control group challenged in parallel (dotted line). Group size 12-16 mice. The data were analyzed using log-rank (Mantel-Cox) test, where $P \leq 0.05$ was regarded as significant. See also data in Table 2.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" s the order in which amino acid residues, connected by peptide bonds, lie in the chain in peptides and proteins.

The term "adjuvant" has its usual meaning in the art of vaccine technology, i.e, a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif})\cdot100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAAC-3' and 5'- ATACGGGAC-3' will provide the sequence identity 77.8% ($N_{ref}=9$ and $N_{dif}=2$). It will be understood that such a sequence identity determination requires that the two aligned sequences are aligned so that there are no overhangs between the two sequences: each amino acid in each sequence will have to be matched with a counterpart in the other sequence.

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immungon by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "linker" is an amino acid sequence, which is introduced between two other amino acid sequences in order to separate them spatially. A linker may be "rigid", meaning that it does substantially not allow the two amino acid sequences that it connects to move freely relative to each other. Likewise, a "flexible" linker allows the two sequences connected via the linker to move substantially freely relative to each other. In the fusion proteins, which are part of the present invention, both types of linkers are useful. However, one particular interesting linker useful in the present invention has the 12 amino acid residuce sequence AEAAAKEAAAKA (SEQ ID NO: 43). Other linkers of interet are listed below.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule prese An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigens determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody"refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody"includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterelogous nucleic acid sequence The term "expression vector" refers to a vector containing a nucleic acid sequence coding for at least part of a gene product capable of being transcribed. In some cases, when the transcription product is an mRNA molecule, this is in trun translated into a protein, polypeptide, or peptide.

Specific Embodiments of the Invention

The Polypeptides of the Invention

In some embodiments the at least 5 contiguous amino acids referred to in option b) in the definition of the first aspect of the invention constitute at least or exactly or at most 6, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least of exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, or at least or exactly or at most 134 contiguous amino add residues.

The number of contiguous amino acids in option b) can be higher, for all of SEQ ID NOs. 2-30. Another way to phrase this is that for each of SEQ ID NOs: 1-14, the number of the contiguous amino acid residues is at least or exactly or at most N−n, where N is the length of the sequence ID in question and n is any integer between 1 and N−5; that is, the at least or exactly 5 contiguous amino adds can be at least any number between 5 and the length of the reference sequence minus one, in increments of one.

Insofar as embodiment b relates to SEQ ID NOs: 2-14, the at least 5 contiguous amino adds referred to in option b) in the definition of the first aspect of the invention may also constitute at least or exactly or at most 135, at least or exactly or at most 136, or at least or exactly or at most 137 contiguous amino acid residues.

Insofar as embodiment b relates to SEQ ID NOs: 3-14, the at least 5 contiguous amino acids referred to in option b) in the definition of the first aspect of the invention may also constitute at least or exactly or at most 138, at least or exactly or at most 139, or at least or exactly or at most 140 contiguous amino acid residues.

Insofar as embodiment b relates to SEQ ID NOs: 4-14, the at least 5 contiguous amino acids referred to in option b) in the definition of the first aspect of the invention may also constitute at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, or at least or exactly or at most 149 contiguous amino acid residues.

Insofar as embodiment b relates to SEQ ID NOs: 5-15, the at least 5 contiguous amino acids referred to in option b) in the definition of the first aspect of the invention may also constitute at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, or at least or exactly or at most 236 contiguous amino acid residues.

Insofar as embodiment b relates to SEQ ID NOs: 6-14, the at least 5 contiguous amino acids referred to in option b) in the definition of the first aspect of the Invention may also constitute at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 315, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 345, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 352, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, or at least or exactly or at most 395 contiguous amino acid residues.

Insofar as embodiment b relates to SEQ ID NOs: 7-14, the at least 5 contiguous amino acids referred to in option b) in the definition of the first aspect of the invention may also constitute at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430 at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, or at least or exactly or at most 542 contiguous amino acid residues.

Insofar as embodiment b relates to SEQ ID NOs: 8-14, the at least 5 contiguous amino acids referred to in option b) in the definition of the first aspect of the invention may also constitute at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576 at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, or at least or exactly or at mast 638 contiguous amino acid residues.

Insofar as embodiment b relates to SEQ ID NOs: 9-14, the at least 5 contiguous amino acids referred to in option b) in the definition of the first aspect of the invention may also constitute at least or exactly or at most 639 , at least or exactly or at most 640, at least or exactly or at most 641, at least or exactly or at most 642, at least or exactly or at most 643, at least or exactly or at most 644, at least or exactly or at mast 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 558, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, or at least or exactly or at most 674 contiguous amino acid residues, Insofar as embodiment b relates to SEQ ID NOs: 10-14, the at least 5 contiguous amino adds referred to in option b) in the definition of the first aspect of the invention may also constitute at least or exactly or at most 675, at least or exactly or at most 676, at least or exactly or at most 677, at least or exactly or at most 678, at least or exactly or at most 679, at least or exactly or at most 680, or at least or exactly or at most 681 contiguous amino acid residues.

Insofar as embodiment b relates to SEQ ID NOs: 11-14, the at least 5 contiguous amino acids referred to in option b) in the definition of the first aspect of the invention may also constitute at least or exactly or at most 682, at least or exactly or at most 683, at least or exactly or at most 684, at least or exactly or at most 685, or at least or exactly or at most 686 contiguous amino acid residues.

Insofar as embodiment b relates to SEQ ID NOs: 12-14, the at least 5 contiguous amino acids referred to in option b) in the definition of the first aspect of the invention may also constitute at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, or at least or exactly or at most 802 contiguous amino acid residues.

Insofar as embodiment b relates to SEQ ID NOs: 13 or 14, the at least 5 contiguous amino acids referred to in option b) in the definition of the first aspect of the invention may also constitute at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1096, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, at least or exactly or at most 1160, or at least or exactly or at most 1161 contiguous amino acid residues.

Insofar as embodiment b relates to SEQ ID NO: 14, the at least 5 contiguous amino acids referred to in option b) in the definition of the first aspect of the invention may also constitute at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, or at least or exactly or at most 1416 contiguous amino acid residues.

In some embodiments, the polypeptide of the invention also has a sequence identity with the amino add sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 95%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, and 131 in any one of SEQ ID NOs: 1-14, if the length of the at least 5 amino acid residues so permits if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 132, 133, and 134 in any on of SEQ ID NOs: 2-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 135, 136, and 137 in any one of SEQ ID NOs: 3-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino adds defined for option b.

In the embodiments defined by option b) above, the polypeptide of the invention is also one that has at least 5 contiguous amino acid residues defined for option b) above and also has its N-terminal amino acid residue corresponding to any one of amino acid residues 138, 139, 140, 141, 142, 143, 144, 145, and 146 in any one of SEQ ID NOs: 4-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, and 233 in any one of SEQ ID NOs: 5-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, and 392 in any one of SEQ ID NOs: 6-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, and 539 in any one of SEQ ID NOs: 7-14, if the length of the at least 5 amino acid residues so permit if—the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino add residue corresponding to any one of amino add residues 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, and 635 in any one of SEQ ID NOs: 8-14, if the length of the at least 5 amino acid residues so permit—if the length of the at least 5 amino acids is higher than 5, the N-terminal first residue will not be higher numbered than N−L+1, where N is the number of amino add residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, and 671 in any one of SEQ ID NOs: 9-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino add residues defined for option b) above and also has its N-terminal amino acid residue corresponding to any one of amino acid residues 672, 673, 674, 675, 676, 677, and 678 in any one of SEQ ID NOs: 10-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 679, 680, 681, 682, and 683 in any one of SEQ ID NOs: 11-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, and 799 in any one of SEQ ID NOs: 12-14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, and 1158 in SEQ ID NO: 13 or 14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, and 1413 in SEQ ID NO: 14, if the length of the at least 5 amino acid residues so permit—if the length of the at least 5 amino acids is higher than 5, the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-14. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra.

In embodiments, the polypeptides defined above may form part of other fusion polypeptides, in particular part of fusion polypeptides that include at least two of the polypeptides of the present invention or polypeptides derived from any one of SEQ ID NOs: 1-30 in WO 2017/005670. In those cases, the polypeptides disclosed herein (i.e. derived from SEQ ID NOs: 1-14) or in WO 2016/005670 (where they have SEQ ID NOs: 1-30) may be fused directly end-to-end or via a peptide linker, such as the linker having SEQ ID NO: 43.

Apart from the linker having SEQ ID NO: 43 (a rigid linker) other specific linkers are also of relevance for the present invention:

| Linker Type | Name | Sequence |
|---|---|---|
| Flexible (short) | FS | GSGGGA (SEQ ID NO: 61) |
| Flexible (long) | FL | GSGGGAGSGGGA (SEQ ID NO: 62) |

-continued

| Linker Type | Name | Sequence |
|---|---|---|
| Flexible (very long) | FV1 | GSGGGAGSGGGAGSGGGA (SEQ ID NO: 63) |
| Flexible (very long) | FV2 | GSGGGAGSGGGAGSGGGAGS GGGA (SEQ ID NO: 64) |
| Flexible (medium long) | FM | GENLYFQSGG (SEQ ID NO: 65) |
| Rigid (long) | RL1 | KPEPKPAPAPKP (SEQ ID NO: 66) |
| Rigid (long) | RL2 | AEAAAKEAAAKA (SEQ ID NO: 43) |
| Rigid (medium long) | RM | SACYCELS (SEQ ID NO: 67) |

However, any peptide linker may in principle be used.

Such fusion polypeptides can include 2, 3, 4, 5, 6, 7, 8, 9, 10 or more distinct polypeptides of the present invention, which may be derived from 1, 2, 3, 4, 5, 6, 7, 8, 9, 10, 11, 12, 13, or 14 of SEQ ID NOs: 1-14

In preferred embodiments, the polypeptide of the invention detailed above is capable of inducing an adaptive immune response against the polypeptide in a mammal, in particular in a human being. Preferably, the adaptive immune response is a protective adaptive immune response against infection with *Pseudomonas aeruginosa*. The polypeptide may in these cases induce a humeral and/or a cellular immune response.

Epitopes

SEQ ID NOs: 1-14 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised agains *Pseudomonas aeruginosa* or *Pseudomonas aeruginosa* derived proteins disclosed herein are tested for binding to overlapping oligomeric peptides derived from any one of SEQ ID NO: 1-14. Thereby, the regions of the *Pseudomonas aeruginosa* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-14 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 15-28) or an RNA fragment (such as SEQ ID NOs 29-42).

The nucleic acid fragment of the invention typically consists of at least 11, such as at least 12, at least 13, at least 14, at least 15, at least 16, at least 17 at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, at least 153, at least 154, at least 155, at least 156, at least 157, at least 158, at least 159, at least 160, at least 171, at least 172, at least 173, at least 174, at least 175, at least 176, at least 177, at least 178, at least 179, at least 180, at least 181, at least 182, at least 183, at least 184, at least 185, at least 186, at least 187, at least 188, at least 189, at least 190, at least 191, at least 192, at least 193, at least 194, at least 195, at least 196, at least 197, at least 198, at least 199, at least 200 and at least 201 consecutive nucleotides in any one of SEQ ID NOs: 15-42. Longer fragments are contemplated, i.e. fragments having at least 200, at least 300 at least 400, at least 500, at least 600, at least 700, at least 800, at least 900, at least 1000, at least 1500, at least 2000, at least 2500, at least 3000, at least 3500, and at least 4000 nucleotides from those of SEQ ID NOs: 15-42 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The Vectors of the Invention

Vectors of the invention fall into several categories discussed infra. One preferred vector of the invention comprises in operable linkage and in the direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of orgin, recombinant production is conveniently effected in bacterial host cells, so here it is preferred that the expression control region drives expression in prokaryotic cell such as a bacterium, e.g. in *E coli*. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

A more detailed discussion of vectors of the invention provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQα and/or DQβ, β-Interferon, Interleukin-2, Interleukin-2 Receptor, MHC Class II 5, MHC Class II HLA-DRα, β-Actin, Muscle Creatine Kinase (MCK), Pre-albumin (Transthyretin), Elastase I, Metallothionein (MTII), Collagenase, Albumin, α-Fetoprotein, γ-Globin, c-fos, c-HA-ras, Insulin, Neural Cell Adhesion Molecule (NCAM), αl-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include MT II—Phorbol Ester (TFA)/Heavy metals; MMTV (mouse mammary tumor virus)—Glucocorticoids; β-Interferon—poly(rl)x/poly(rc); Adenovirus 5 E2—EIA; Collagenase—Phorbol Ester (TPA); Stromelysin—Phorbol Ester (TPA); SV40—Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70—E1A/SV40 Large T Antigen; Proliferin—Phorbol Ester/TPA; Tumor Necrosis Factor—PMA; and Thyroid Stimulating Hormoneα Gene—Thyroid Hormone.

Also contemplated as useful in the present invention are the dectin-1 and dectn-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells.

Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli*.), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

An interesting production system is the use of plants. For instance, proteins can be produced at low cost in plants using an *Agrobacterium* transfection system to genetically modify plants to express genes that encode the protein of interest. One commercially available platform are those provided by iBio CMO LLC (8800 HSC Pkwy, Bryan, TX 77807, USA) and iBio, Inc (9 Innovatoin Way, Suite 100, Newark, DE 19711, USA) and disclosed in e.g. EP 2 853 599, EP 1 769 068, and EP 2 192 172. Hence, in such systems the vector is an *Agrobacterium* vector or other vector suitable for transfection of plants.

As noted above, stably transformed cells are preferred— these i.a. allows that cell lines comprised of transformed cells as defined herein may be established—such cell lines are partilucarly preferred aspects of the invention.

Further details on cells and cell lines are presented in the following:

Suitable cells for recombinant nucleic add expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the

*Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JMI 09, and KCB, as well as a number of commercially available bacterial hosts such as SURE® Competent Cells and SOLOP ACK™ Gold Cells (STPATAGENE®, La Jolla, CA). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic add sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic add delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859), including microinjection (U.S. Pat. No. 5,789,215); by electroporation (U.S. Pat. No. 5,384, 253); by calcium phosphate precipitation; by using DEAE dextran followed by polyethylene glycol; by direct sonic loading; by liposome mediated transfection; by microprojectile bombardment (PCT Application Nos. WO 94/09699 and 95/06128; U.S. Pat. Nos. 5,610,042; 5,322,783 5,563, 055, 5,550,318, 5,538,877 and 5,538,880); by agitation with silicon carbide fibers (U.S. Pat. Nos. 5,302,523 and 5,464, 765); by *Agrobacterium* mediated transformation (U.S. Pat. Nos. 5,591,616 and 5,563,055); or by PEG mediated transformation of protoplasts (U.S. Pat. Nos. 4,684,611 and 4,952,500); by desiccation/inhibition mediated DNA uptake. Through the application of techniques such as these, organelle(s), cell(s), tissue(s) or organism(s) may be stably or transiently transformed.

The Antibodies of the Invention—and Their Production/Isolation

Antibodies directed against the proteins of the invention are useful for affinity chromatography, immunoassays, and for distinguishing/identifying Pseudomonas proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 10-200 µg/injection is typically sufficient. Immunization is generally boosted 2-5 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4° C. for 2-18 hours. The serum is recovered by centrifugation (eg. 1,000 g for 10 minutes), About 20-50 ml per bleed may be obtained from rabbits.

Monoclonal antibodies are prepared using the standard method of Köhler & Milstein [Nature (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and l25I), electron-dense reagents, enzymes, and ligands having specific binding partners. Enzymes are typically detected by their activity. For example, horseradish peroxidase is usually detected by its ability to convert 3,3', 5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 115I may serve as a radioactive label or as an electron-dense reagent. HRP may serve as enzyme or as antigen for a MAb. Further, one may combine various labels for desired effect For example, MAbs and avidin also require labels in the practice of this invention: thus, one might label a MAb with biotin, and detect its presence with avidin labeled with, l25I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an F(ab')$_2$, an scFV; cf. also the definition of the term "antibody" presented above.

Compositions of the Invention: Vaccines

Pharmaceutical compositions, in particular vaccines, according to the invention may either be prophylactic (ie. to prevent infection) or therapeutic (ie, to treat disease after infection).

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is an MVA vector mentioned herein, which encodes and can effect expression of at least 2 nucleic acid fragments of the invention.

An embodiment of a pharmaceutical composition of the invention comprises exactly Y or at least Y distinct (i.e having non-identical primary structure) polypeptides of the invention described herein, where each of said Y or at least Y distinct polypeptides comprises an immunogenic amino acid sequence present in or derived from any one of SEQ ID NOs: 1-14 and wherein said Y or at least Y distinct polypeptides together comprise immunogenic amino acid sequences present in or derived from Y or at least Y of SEQ ID NOs. 1-14, wherein Y is an integer selected from 2, 3, 4, 5, 6, 7, 8, 9, 10, 11, 12, 13, 14.

A related embodiment of a pharmaceutical composition of the invention comprises exactly Y' or at least Y' distinct (i.e. having non-identical primary structure) polypeptides, wherein at least one is a polypeptide including an immunogenic amino acid sequence present in or derived from any one of SEQ ID NOs: 1-14 of the present invention and described herein, and wherein at least one other polypeptide in the composition is disclosed in WO 2017/005670 as being present in or derived from any one of SEQ ID NOs 1-30 in WO 2017/005670, and wherein said Y' or at least Y' distinct polypeptides together comprise immunogenic amino acid sequences present in or derived from Y' or at least Y' of SEQ ID NOs. 1-14 and SEQ ID NOs 1-30 in WO 2017/005670, wherein Y' is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, and 44.

Another embodiment of a pharmaceutical composition of the invention comprises a peptide/polypeptide comprising or consisting of an immunogenic amino acid sequence present in or derived from SEQ ID NO: 1 in combination with at least one *P. aeruginosa* peptide/polypeptide, in particular with at least one peptide/polypeptide comprising or consisting of an immunogenic amino acid sequence present in or derived from any one of SEQ ID NOs: 2-14 or disclosed in WO 2017/005670 as being present in or derived from any one of SEQ ID NOs 1-30 in WO 2017/005670. Another embodiment of a pharmaceutical composition of the Invention comprises a peptide/polypeptide comprising or consisting of an immunogenic amino acid sequence present in or derived from SEQ ID NO: 2 in combination with at least one *P. aeruginosa* peptide/polypeptide, in particular with at least one peptide/polypeptide comprising or consisting of an immunogenic amino acid sequence present in or derived from any one of SEQ ID NOs: 1, and 3-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 3 in combination with at least one *P. aeruginosa* peptide/polypeptide, in particular with at least one peptide/polypeptide comprising or consisting of an immunogenic amino acid sequence present in or derived from any one of SEQ ID NOs: 1, 2, and 4-14 or disclosed in WO 2017/005670 as being present in or derived from any one of SEQ ID NOs 1-30 in WO 2017/005670. Another embodiment of a pharmaceutical composition of the Invention comprises a peptide/polypeptide comprising or consisting of an immunogenic amino acid sequence present in or derived from SEQ ID NO: 4 in combination with at least one *P. aeruginosa* peptide/polypeptide, in particular with at least one peptide/polypeptide comprising or consisting of an immunogenic amino acid sequence present in or derived from any one of SEQ ID NOs: 1-3, and 5-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 5 in combination with at least one *P. aeruginosa* peptide/polypeptide, in particular with at least one peptide/polypeptide comprising or consisting of an immunogenic amino acid sequence present in or derived from any one of SEQ ID NOs: 1-4, and 6-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 6 in combination with at least one *P. aeruginosa* peptide/polypeptide, in particular with at least one peptide/polypeptide comprising or consisting of an immunogenic amino acid sequence present in or derived from any one of SEQ ID NOs: 1-5, and 7-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 7 in combination with at least one *P. aeruginosa* peptide/polypeptide, in particular with at least one peptide/polypeptide comprising or consisting of an immunogenic amino acid sequence present in or derived from any one of SEQ ID NOs: 1-6, and 8-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 8 in combination with at least one *P. aeruginosa* peptide/polypeptide, in particular with at least one peptide/polypeptide comprising or consisting of an immunogenic amino acid sequence present in or derived from any one of SEQ ID NOs: 1-7, and 9-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 9 in combination with at least one *P. aeruginosa* peptide/polypeptide, in particular with at least one peptide/polypeptide comprising or consisting of an immunogenic amino acid sequence present in or derived from any one of SEQ ID NOs: 1-8, and 10-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 10 in combination with at least one *P. aeruginosa* peptide/polypeptide, in particular with at least one peptide/polypeptide comprising or consisting of an immunogenic amino acid sequence present in or derived from any one of SEQ ID NOs: 1-9, and 11-14 or disclosed in WO 2017/005670 as being present in or derived from any one of SEQ ID NOs 1-30 In WO 2017/005670. Another embodiment of a pharmaceutical composition of the invention comprises a peptide/polypeptide comprising or consisting of an immunogenic amino acid sequence present in or derived from SEQ ID NO: 11 in combination with at least one *P. aeruginosa* peptide/polypeptide, in particular with at least one peptide/polypeptide comprising or consisting of an immunogenic amino acid sequence present in or derived from any one of SEQ ID NOs: 1-10, and 12-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 12 in combination with at least one *P. aeruginosa* peptide/polypeptide, in particular with at least one peptide/polypeptide comprising or consisting of an immunogenic amino acid sequence present in or derived from any one of SEQ ID NOs: 1-11, and 13-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 13 in combination with at least one *P. aeruginosa* peptide/polypeptide, in particular with at least one peptide/polypeptide comprising or consisting of an immunogenic amino acid sequence present in or derived from any one of SEQ ID NOs: 1-12, and 14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 14 in combination with at least one *P. aeruginosa* peptide/polypeptide, in particular with at least one peptide/polypeptide comprising or consisting of an immunogenic amino acid sequence present in or derived from any one of SEQ ID NOs: 1-13 or disclosed in WO 2017/005670 as being present in or derived from any one of SEQ ID NOs 1-30 in WO 2017/005670.

These embodiments entail combinations of pepticles/polypepides which are admixed with each other. Alternatively, the same combinations of peptides/polypeptides can be constructed as fusion polypeptides, optionally separated by linkers such as the linker having SEQ ID NO: 43. Another alternative entails compositions where the immunogens are nucleic acids (DNA or RNA) encoding the peptide combinations or, preferably, encoding such fusion polypeptides.

Another embodiment of the pharmaceutical composition of the invention comprises Z or at least Z distinct nucleic acid molecules each encoding a polypeptide of the invention, where each of said Z or at least Z distinct nucleic add molecules encodes an immunogenic amino acid sequence present in or derived from any one of SEQ ID NOs: 1-14, and wherein said at Z or least Z distinct nucleic acid molecules together encode immunogenic amino acid sequences present in or derived from at Z or least Z of SEQ ID NOs. 1-14, wherein Z is an integer selected from 1, 2, 3, 4, 5, 6, 7, 8, 9, 10, 11, 12, 13, and 14. Also, such a pharmaceutical composition may include nucleic acids that encode several immunogenic amino acid sequences disclosed herein, either as separate encoded species or as peptides fused to eachother. So one variation of this embodiment is one single nucleic acid molecule, which encodes one or more of the polypeptides disclosed above or one or more of the combinations of peptides disclosed above.

A related embodiment of the pharmaceutical composition of the invention comprises Z' or at least Z' distinct nucleic acid molecules each encoding a polypeptide of the present invention, where each of said Z' or at least Z' distinct nucleic acid molecules encodes an immunogenic amino acid sequence present in or derived from any one of SEQ ID NOs: 1-14 and wherein the Z' or at least Z' distinct nucleic acids in adddtion encodes at least one protein or polypeptide being present in or derived from any one of SEQ ID NOs 1-30 in WO 2017/005670 and wherein said at Z or least Z distinct nucleic acid molecules together encode immunogenic amino acid sequences present In or derived from Z' or at least Z' of SEQ ID NOs. 1-14 and SEQ ID NOs 1-30 in WO 2017/005670, wherein Z' is an integer selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 3 7 , 38, 39, 40, 41, 42, 43, and 44. Also, such a pharmaceutical composition may include nucleic acids that encode several immunogenic amino acid sequences disclosed herein, either as separate encoded species or as peptides fused to each other. So one variation of this embodiment is one single nucleic acid molecule, which encodes one or more of the polypeptides disclosed above or one or more of the combinations of peptides disclosed above.

Vaccines of the invention typically comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition or targeting the protein/pathogen. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, MA), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, MT) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+ CWS (Detox™); (3) saponin adjuvants such as Stimulon™ (Cambridge Bioscience, Worcester, MA) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, I-6, IL-7, I-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MFS9™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogicaliy effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 μg and 500 mg (however, often not higher than 5,000 μg), and very often in the range between 10 and 200 μg.

The immunogenic compositions are conventionally administered parenterally, eg, by injection, either subcutaneously, intramuscularly, or transdermaliy/transcutaneously (eg. W098/20734). Additional formulations suitable for other modes of administration include oral, pulmonary and nasal formulations, suppositories, and transdermal applications. In the case of nucleic acid vaccination and antibody treatment, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Imlllunol 9: 271-283; Donnelly et al. (1997) Avnu Rev Innnunol 15 : 617-648; later herein].

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 μg of the polypeptide of the invention per administration.

In preferred embodiments of the sixth aspect, the immuniation scheme includes that the animal (e.g. the human) receives a priming administration and one or more booster administrations.

Preferred embodimentms of the $6^{th}$ aspect of the invention comprise that the administration is for the purpose of inducing protective immunity against *Pseudomonas aeruginosa*. In this embodiment it is particularly preferred that the protective immunity is effective in reducing the risk of attracting infection with *Pseudomonas aeruginosa* or is effective in treating or ameliorating infection with *Pseudomonas aeruginosa*.

As mentioned herein, the preferred vaccines of the invention induce humoral immunity, so it is preferred that the administration is for the purpose of inducing antibodies specific for *Pseudomonas aeruginosa* and wherein said antibodies or B-lymphocytes producing said antibodies are subsequently recovered from the animal.

But, as also mentioned the method of the 6' aspect may also be useful in antibody production, so in other embodiments the administration is for the purpose of inducing antibodies specific for *Pseudomonas aeruginosa* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claim, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with *Pseudomonas aeruginosa;*

US 12,606,597 B2

45 the nucleic acid fragment of the invention or the vector of
the invention is for use as a pharmaceutical, in particu-
lar for use as a pharmaceutical in the treatment, pro-
phylaxis or amelioration of infection with *Pseudomo-
nas aeruginosa;* the transformed cell of the invention is for use as a
pharmaceutical, in particular for use as a pharmaceu-
tical in the treatment, prophylaxis or amelioration of
infection with *Pseudomonas aeruginosa,* the antibody, antibody fragment or antibody analogue of
the invention is for use as a pharmaceutical, in particu-
lar for use as a pharmaceutical in the treatment, pro-
phylaxis or amelioration of infection with *Pseudomo-
nas aeruginosa.*

Biologic Sequence Information

The full-length, native polypeptides of the invention have
the following designations used herein:

| Sequence number | Polypeptide designation |
|---|---|
| SEQ ID NO: 1: | PA4877 |
| SEQ ID NO: 2: | PA4874 |
| SEQ ID NO: 3: | PA1870 |
| SEQ ID NO: 4: | PA4697 |
| SEQ ID NO: 5: | PA0833 |
| SEQ ID NO: 6: | PA1011 |
| SEQ ID NO: 7: | PA3075 |
| SEQ ID NO: 8: | PA0428 |
| SEQ ID NO: 9: | PA4571 |
| SEQ ID NO: 10: | PA3340 |
| SEQ ID NO: 11: | PA0781 |
| SEQ ID NO: 12: | PA0685 |

46

-continued

| Sequence number | Polypeptide designation |
|---|---|
| SEQ ID NO: 13: | PA1527 |
| SEQ ID NO: 14: | PA4541 |

A number of the polypeptides of the invention are frag-
ments of the full-length, native polypeptides. Such frag-
ments are named as follows: PAXXXX_Y-Z or PAXXXX-
Y-Z, where XXXX is the number in the polypeptide
designation, X is the number of the N-terminal amino acid
residue in the fragment and Z is the number of the C-ter-
minal amino acid residue. For instance, PA1011_100-880
would be the polypeptide having the amino acid sequence
SEQ ID NO: 6, residues 100-880.

Furthermore, some constructs of the invention are fusion
polypeptides constituted by more than one of the above
polypeptides. The will typically have the designation
PP1_PP2, where each of PP1 and PP2 are polypeptides
designated as above. An example would be PA1011_100-
880_PA0685_600-700, which would be the polypeptide
having the amino acid sequence SEQ ID NO: 6, residues
100-880, fused at its C-terminus to the polypeptide having
SEQ ID NO: 12, residues 600-700.

Finally, som constructs have the amino acid sequence
AEAAAKEAAAKA (SEQ ID NO: 43) inserted between
two fusion partners. Such constructs are named as above, but
prefixed with "RL2". An example would be
RL2_PA1011_100-880_PA0685_600-700, which would be
the polypeptide having the amino acid sequence SEQ ID
NO: 6, residues 100-880, fused C-terminally to SEQ ID NO:
43, which in turn is fused C-terminally to the polypeptide
having SEQ ID NO: 12, residues 600-700.

The polypeptides of the present invention have the fol-
lowing amino acid sequences:

```
                                          SEQ ID NO: 1
MPRGDKSKYSDKQQRKAEHIEESYKAKGVSESEAEARAWATVNKQSGGGERKGGSGRAKSETAKRAD

RKDSAHRAAQARSGRPANRGSASRGKRQGSTSVSEMTREELMQLARKRDIRGRSTMRKAELIEALSRA

SEQ ID NO: 2
MNILRIPMFVLAMAVSAHGFAATAQQEKMTACNAEATTKALKGDERKAFMSGCLKAGAPAGGKATAQQE

KMKSCNADASAKSLKGDERKAFMSSCLKAGGSAKAATQQEKMKTCNADATAKALKGDERKAFMSTCLK

K

SEQ ID NO: 3
MATRRKTTPQEIDDIQDRMGSMRELDFDERRQARKARIGDERPEAEVEAEFSSRRVREAGHAGGQPDED

DGYQDNVGMDDLAPETLIDESGARSPAERGGESPADKRLRVVHGNEIGAGHGLDEAELARRDPLDGSS

DEER

SEQ ID NO: 4
MRRMILPASLLLALSSFAMAAPIYKWVDAEGVTHFGAQPPQGAQATTVNTQTAPPPDNFPLPPSTPAPTIQ

QKPADPEQKAIDDKVKQQVAKEEAERKQFCEETRNNLAQLKNNPRVRVDEGKGELRRLGEEERQERIAK

AEKAIQENCR

SEQ ID NO: 5
MFTSRCLPLAAAVTALALLAGCANNNPYDTQSQSQGGMSKTAKYGGLGALAGAVAGAAIDHNNRGKGAL

IGAAVAGAAAAGYGYYADKQEAELRRQMEGTGVEVQRQGDDIKLIMPGNITFATDSANIAPSFYAPLNNL

ANSFKQYNQNTIEIVGYTDSTGSRQHNMDLSQRRAQSVAGYLTAQGVDGTRLSTRGMGPDQPIASNST

ADGRAQNRRVEVNLRPVPGAQGPAQTQPQY
```

-continued

SEQ ID NO: 6

MKRLAGLTALALVIGNTSGCGWLWGPEGYFRDRGDDYLGARETPPMQLPEGVHSKPLDPLLPIPLNVATT

HEKEGEYEVPRPQPLANAGDISDYSLQRSGDSRWVVAQRPPAEVWPVARQFFEENGFRIADERPQTGEF

SSDWQSLSQLSAPLARRLSSRVSGVEPDGQARVRVRIEPGVQSNTSEVYVLSQTRAAGDTSSPSWPSKS

VAPSLDAALLDEMVASMARSAEQGGSVSLLAANSIYDTPGTFELSKDGSGNPVLTLQSDFDRSWVSVGR

ALDNADIRVDDLNRSLGVYYVNIAEGAKKPDEDKPGFFSRLFGGGEKTKEEEDAKAQRYQVRLTTVSDAV

QVTVDKDINTSAPADVAQNVLEKLQESMRNAVRGSGQRKPGQFGLGEQF

SEQ ID NO: 7

MIRLFCSLLLALLCVSAHASFSASVDRARLTEGESVELTLESDDPTLFGKPDLSPLDALFEVLGTRQVNRLA

TQNGRAQATTRWIVTLLPKQSGYVAIPPISLGASSTQPIRLHVLEARDRAKSSKLAPVFIDASVDQETVYV

QAQAILTLRIYHSVSLYDDSSLTPLAMNDAKVEQLGEARTYEKEINGIRHGVIEVRYAIFPQKSGTLEIPAQ

AFSATLVDRGSDDYNPFGPRPGRQMRVTSPSIPLQVRPKPADYPADAPWMPARALSISESWSPQPEQAQ

VGESLTRNVLLKVEGLSGTQLPPLPLPDVQGLRRYPDQPQLADQSTDQGLIGSREEREALVPEQAGRIELP

ALEVVWWNTREDRLERTSLPPRTLEVAAAPQAEAEPPAAALPLGERLEPTLWPWQLATAVLALTTLLGFGL

WWRARQLPAVIRAAANGPSSRSLLDELRRACLANDPQATRQALDAWARQQPDTLADMAARFVPLSDAL

DGLNGALYSESGHSWQGEDLWRAIRALPTTEQAPAGAVDNGGLPPLYPR

SEQ ID NO: 8

MSFSSLGLSEALARAVEAAGYSQPTPVQQRAIPAVLQGRDLMVAAQTGTGKTGGFALPVLERLFPAGHPD

REHRHGPRQARVLVLTPTRELAAQVHDSFKVYARDLPLNSTCIFGGVGMNPQIQALAKGVDVLVACPGRL

LDLAGQNKVDLSHVEILVLDEADRMLDMGFIHDVKKVLAKLPPKRQNLLFSATFSKDIVDLANKLLHNPER

IEVTPPNTTVERIEQRVFRLPAPQKRALLAHLVTVGAWEQVLVFTRTKHGANRLAEYLTKHGLPAAAIHGN

KSQNARTKALADFKANDVRILVATDIAARGLDIDQLPHVVNYELPNVEEDYVHRIGRTGRAGRSGEAISLV

APDEEKLLKAIEKMTRQRIPDGDAQGFDPEAVLPEVAQPEPREAPQKQPRRDKERRSSRERKPKDAQASN

PDSNVAAAQDGTEKPAGKRRRRGGKNKENREAGQAQQPRQSREARPAKPNRPPEVDGNRDPEEFLDDD

FDNFGNRADYVSPYQGQENKGRGRRGGQQKPQGGTGQQGRGQGQGQARGKSQGAAQGGARGQGA

GQGKAKKPRAGKPRGQGRENASRMSDAPLREPSEYGTGKQPSRQPVVINKRDLVRMDRFPTAEQLDELE

PRRKGERPALLTRNR

SEQ ID NO: 9

MPASFPRLGLLGALCSIVPLLHASEPTTDAALIEKGRYVAQLGDCIACHTGPQGAPMAGGLELKTPMGTIY

STNITPDRETGIGRYSFEEFDRAMRKGVTAEGVNLYPAMPYPSYAKISEEDMRALYAYLMHGVQPVTQAN

TPSAMSWPFNQRWGLSLWNWAFLDDAPFTPSSDADPVINRGAYLVQGLGHCGACHTPRGIAFQEKAMS

EAGRSGQFYLAGETVEQWQALSLRNLWTVEDTVQLLKTGQNRFATVSGSMTDVIHHSTQHFSDDDLLAI

ASYLKSLPAGKDDLPMPDSERPLAAPVDLYSSRGGLGYAQFCSDCHRKDGSGVPGMFPPLAGNPTVASA

NPSTLLHITLTGWKTAQTATHSRVYTMPGFAQLEDREIAEILSFVRSSWGNQGSSIDAGQVKKLRQRIEA

GNGPATTFVSPRLADMLAAPNAEQVVRGMRLHLETRELLPANVGNQLHCTSCHLNAGTVADGSPFVGVS

AFFPSYAPRAGKVIGLEERINGCFRRSMNGKPLPPDSADMQAMVAYFDWMKNNTRPQDKVAGRGVGKV

DPALKPDPENGRKVYARQCVVCHGENGEGLRNSAGEMLFPPLWGDESFNIGAGMARTFTAAAFVKHNM

PIGFQERFPLGQGGLSDQDAVDVAEYFSHQPRPDFPDKIKDWPKDKRPLDARY

SEQ ID NO: 10

MPGKALRVMLCAWSCLLAGQASALGVGDIILHSALNQPLDADIELLDVGDLGADEIEVRLAGADVFAAAG

VERLQFLNELRFSPVLQGRGGNRIHVSSIRPVQEPYLNFLVEVARPNGRIVREFTVLLDPLGYTPRMLPAAR

SGIEPQRQSSTPVPAPRSAAVVVDPALLEPGDEYLARPSDNLWAISGRLRGAGNADRAQLMEALYQLNPQ

AFVNADRHRLKAGARLRLPAGYQPERGAPGAVKEAAVEVLPPADAAVVENAPAALVEAQRQADAEAEALA

-continued

RQREELSQRMDDLQRQLQALQEQLQQRDHQVAELQQQLARRQAVRPAAPPPAAAAPSVAQPVETPTDS

QYWRWMIVLLLVLALLGVLLLRRRREEAPVPAVEPKRRVALNLPLRRAPRPPAAAPAPAKVEEQARPPVAAP

SSPPPSPPPAPAAAPRAAMAAADKLDGADIYIAYGRYGQARDLLRQVLAEQPQRLSARMKLLLVLAELGDA

AGFDALAEETLASGGNPEAIDELRGRYPALLQMPATETPAATTKDDDWSDLPLAESPVLQQPDATSGADG

FGDLNLDLDLDWGALENPLDNPDLPRRAAAGKAEPAEEPLAFESNLHELPDVAEYEHLELDQPEPATVPPE

EASASLDRARACIDSGDLDQASRILRLVVAHGDPWQKAEARELLALIA

SEQ ID NO: 11

MSSSGLFPSRPLWPLTPLALACLIVSGETLGADGRPSELPSQVITANPLGNESPATPSSVLEGDELTLRQKG

SLGETLNGLPGVSSTYFGPGASRPVIRGMDGDRIRLLRNGVGALDASSLSYDHAVPEDPNSVERLEVVRG

PAALLYGGNAIGGVVNSFDNRIPSEPVDGIHGSGELRYGGADTTRSRSGALEAGDGNFALHVDAASREFN

DVRIPGYAHSSRQRQIDGDTGKHRVQNSDGRQDGGAVGGSYHWEHGYAGLSYSGYDSNYGSPAEDDV

RLKMQQDRYAFASEIRDLEGPFTSLKLDAAYTKYEHKEIEDGETGTTFKNEGYEGRIEARHRPLGPLNGVV

GAQFANSRFSALGEEAFVPHTETDSAALFALEEWKLSDRLDLSFGARLEHTRVDPDAKGNERFAENDGSQ

SFTTGSLSTGAVYKLTPIWSLAATLSYTERAPTFYELYANGPHAATGTYEVGDADADKEKAVSTDLALRFD

NGVHKGSVGVFYSRFSNYIGLLASGRHRNEEGEVVAAGDDEALPEYLYSGVRADFYGVEAQDRIHLLESP

YGNFDLELSGDYTRAKNKDTGEPLPRIAPLRLNTALIWELQQWQARVDVEHAASQHRVPEEELSTDGYTT

LGASLGYNFDLGESRWLAFVKGTNLTNQTVRYASSILRDRVPAAGRGIEAGVKVAF

SEQ ID NO: 12

MRQSAFHHARRRWPVLGVALGALLVAACSETPKVPGVPPADEEVGRPLSSVRSGAPLRSADVRERPQAE

QARRALSAGRGVARSGGVAPVSATAAELGEQPVSLNFVDTEVEAVVRALSRATGRQFLVDPRVKGKLTLV

SEGQVPARTAYRMLTSALRMQGFSVVDVDGVSQVVPEADAKLLGGPVYGADRPAANGMVTRTFRLRYEN

AVNLIPVLRPIVAQNNPINAYPGNNTVVVTDYAENLDRVAGIIASIDIPSASDTDVVPIQNGIAVDIASTVS

ELLDSQGSGGAEQGQKTVVLADPRSNSIVIRSPSPERTQLARDLIGKLDSVQSNPGNLHVVYLRNAQATR

LAQALRGLITGDSGGEGNEGDQQRARLSGGGMLGGGNSGTGSQGLGSSGNTTGSGSSGLGGSNRSG

GAYGAMGSGQGGAGPGAMGEENSAFSAGGVTVQADATTNTLLISAPEPLYRNLREVIDLLDQRRAQVVI

ESLIVEVSEDDSSEFGIQWQAGNLGGNGVFGGVNFGQSALNTAGKNTIDVLPKGLNIGLVDGTVDIPGIG

KILDLKVLARALKSRGGTNVLSTPNLLTLDNESASIMVGQTIPFVSGQYVTDGGGTSNNPFQTIQREDVGL

KLNIRPQISEGGTVKLDVYQEVSSVDERASTAAGVVTNKRAIDTSILLDDGQIMVLGGLLQDNVQQNTDG

VPGLSSLPGVGSLFRYQKRSRTKTNLMVFLRPYIVRDAAAGRSITLNRYDFIRRAQQRVQPRHDWSVGDM

QAPVLPPAQQGIPQAAYDLRPSPRPLRAVPLGEAAPL

SEQ ID NO: 13

MRLKSIKLAGFKSFVDPTTVNFPSNMAAVVGPNGCGKSNIIDAVRWVMGESSAKNLRGESMTDVIFNGS

NTRKPVSQASIELIFDNAETTLVGEYAQYAEISIRRRVSRDGQNTYFLNGTKCRRRDITDIFLGTGLGPRSY

SIIEQGMISKLIEARPEDLRNFIEEAAGISKYKERRRETESRIRRTQENLARLTDLREELGRQLERLHRQAQ

SAEKYQEHKAEERQLKAQLGAVRWRDLNEQVGQRERVIGDQEIAFEALVAEQRGADAGIERLRDGHHEL

SERFNQVQARFYSVGGDIARVEQSIQHGQQRQRQLQDDLREAERTRQETESHLGHDRTLLATLAEEMAM

LAPEQELSAAAAEEAGIALEQAEQGMQAWQQQWDAFNQQSAEPRRQAEVQQSRIQHLEQSLERLQDRE

RRLQEERGQLAADPEDAAILELNEQVAIAELALEELQLQEQGQAERLEQLRQELQQLAAEQHQAQGELQR

LNGRIASLEALQQAALDPGQGALEWLREQGLEQRPRLAEGLRVEPGWELAVETVLGADLQAVLLDGFDGL

ALAGFGKGELRLLSPARGAATAAGSLLDKVRADADLSPWLARVKPVETLEQALAQRGALDDGESLISRDG

YWVGRHFLRVRRSDEAQGGMLARAQELEALQERREALETRVAEGEERLAAARDEQRELEGAREQVRRQV

QEEGRRHGELKAQLSAQQAKVEQLVLRRRRLDEEVAELAEQRALEQEQLSEARLTLQEALDSMALDTERR

-continued

ESLLAERDALRERLDRIRQDARTHKDHAHQLAVRVGSLKAQHNSTQQALERLDQQSARLNERCEQLNLN

LEEGAAPLEELRMKLEELLERRMAVEDELKQARLALEDADRELREVEKRRGQAEQQSQLLRGQLEQQRLE

WQGLVVRRKALQEQLAEDGYDLHTVLANLPLDASERDWEERLESLAARIQRLGPINLAAIEEYQQQSERK

RYLDSQNDDLAEALETLENVIRKIDRETRNRFKETFDQINAGLQALFPKVFGGGTAYLELTGEDLLDTGVAI

MARPPGKKNSTIHLLSGGEKALTALALVFAIFQLNPAPFCMLDEVDAPLDDANVGRYARLVKEMSEKVQFI

YITHNKIAMEMADQLMGVTMHEPGCSRLVAVDVEEAVALAEA

SEQ ID NO: 14
MNKSYTLVWNQATGCWNVASEGTRRRSKSGRGKALVVAGASLLGLFCQAPAFALPSGATVVSGDAGFQ

TSTDGRHMVIDQQSHKLITNWNEFSVRADERVSFHQPGQDAVALNRVIGRNGSDIQGRIDANGKVFLV

NPNGVVFGKSAQVNVGGLVASTLDLADRDFLAGNYQFSGDSGATVSNAGSLQASEGGSIALLGARVSN

DGLIQAQLGDVALGAGQGINLNFDGDGLLNLQVDKGSVDALAHNGGLIRADGGQVLMSARSADSLLKT

VVNNQGTLEARTLRSAEGRIVLDGGEQGTVRVAGKQDASAIGGGNGGLVLNQGANVEIQRTAQVDTHA

DQGATGTWRILSHEVSVAAVGQANAAGDGSGQVHVAQGPAGANASDSNGVTIVQQQPAVDLAAGANG

TSAVQSQSGANIGSGANGISVVQSQNSPNIGSGANGISVVQSQNGANIGAGASGISVVQSQNSPNIGS

GVNGVTVVQSQNGANIGSGASGITVVQSQNGANIGSGASGISVVQSQSGPSIGSGVNGVTIVQSQSGA

NIGPGVSGIDVVQTQTLPNLSPGANGSSIVQVQTLPDIAADAGNVHVVQVQTGGNKVFGNSATNVRSRT

VQARSNENVGSGLANPSSAGKGSTLHADTLARNLSTSNVEVVATRGNAHVGAPLSWDSGNGLTLTAER

GDLRINGALTAQGENASLTLNAGQRPLRIDDSLSLTGQGARVEFNSDKGYALAEGTRITLSGKNAGFRAN

GRDYSVIQDLQQLRGIDRDLGGSYVLGNRIAGGNSSFLSIGNASAFGGTFDGLGNTIDNLAVYGTGAYSG

LFSVNRGTLRNLNLERISADGAQATHYNVQVGSLAAVNLGRIDNVNASDIRIAAASKLNSLGGLVALNLG

SIDNASASGTLVGNRHTYALGGLAAENISTARGVASISNSRADFAISGQLKDHASHYGAGGLVGRNRGG

WIRSSGSQGTLSLSGHGMNLGGLVGYSSAGGLADVSASVDVSGNGQRGLYGGLIGLNVNSGIAHATAS

GKVRGTDAEALGGLIGRNLNAAINNASAHGDVSLQAGRYLGGLIGHNQAGNLANVSTSGNLSGGSLLQA

GGLIGLNANASLVNASAKGNVATRGAEAVGGLLGENLYGSVINGSASGEVTDGSGKTLGGLIGSNLGGN

HSNLKASGWVNAGANSDVGGLIGHNRGGNHSTLAASGNVTGGKGSRVGGLVGYNDAASLTNVSASGN

VSASGSRAIGGLIGSDLRGSLMLASSHGIVNDKTSHNLGGLVGRGENTSIRSAKASGAVSGGAGIRAGG

LVGSLEGWQALILGASAGGDVTAGYDSYIGGLVGFSTATISGASASGKVGGSGLLGGLVAWNQGNVMG

SSASGRLEPQIPNQIHGGLIGINFGWQSWNSVYGAAATVPMIGRHYNL

SEQ ID NO: 43
AEAAAKEAAAKA

The corresponding nucleic acid sequences (DNA in SEQ ID NOs. 15-28 and RNA in SEQ ID NOs: 29-42) to SEQ ID NOs: 1-42 are set forth in the electronic sequence listing that forms part of the present application. SEQ ID NOs: 44-60 set forth the sequences of specific constructs tested in the examples, cf. below, and SEQ ID NOs: 61-67 lists the sequences of a number of peptide linkers.

EXAMPLE 1

Introduction

The purpose of the studies described in the following was to assess the protective effect of 17 recombinant protein constructs in a murine model of *Pseudomonas aeruginosa*-induced peritonitis. The proteins tested were PA4877-1-135 (SEQ ID NO: 1, residues 1-135; also shown in SEQ ID NO: 44)

PA1670-2-141 (SEQ ID NO: 3, residues 2-141; also shown in SEQ ID NO: 45)

PA0833-142-237 (SEQ ID NO: 5, residues 142-237; also shown in SEQ ID NO: 46)

PA1011-20-396 (SEQ ID NO: 6, residues 20-396; also shown in. SEQ ID NO: 47)

PA0428-1-639 (SEQ ID NO: 8, residues 1-639; also shown in SEQ ID NO: 48)

PA4571-24-675 (SEQ ID NO: 9, residues 24-675; also shown in SEQ ID NO: 49)

RL2_PA4571-400-675_PA4571-24-191 (fusion between SEQ ID NO: 43, SEQ ID NO: 9, residues 400-675, and SEQ ID NO: 9, residues 24-191; also shown in SEQ ID NO: 50)

PA3340-372-682 (SEQ ID NO: 15, residues 372-682; also shown in SEQ ID NO: 51)

PA3340-24-351 (SEQ ID NO: 10, residues 24-351; also shown in SEQ ID NO: 52)

RL2_PA0781-32-225_PA0781-515-687 (fusion between SEQ ID NO: 43, SEQ ID NO: 11, residues 32-225, and SEQ ID NO: 11, residues 515-687; also shown in SEQ ID NO: 53)

RL2_PA0781-515-687_PA0781-32-495 (fusion between SEQ ID NO: 43, SEQ ID NO: 11, residues 515-687, and SEQ ID NO: 11, residues 32-495; also shown in SEQ ID NO: 54)

PA0781-32-687 (SEQ ID NO: 11, residues 32-687; also shown in SEQ ID NO: 55)

RL2_PA0685-609-803_PA0685-1-339 (fusion between SEQ ID NO: 43, SEQ ID NO: 12, residues 609-803, and SEQ ID NO. 12, residues 1-339; also shown in SEQ ID NO: 56)

PA1527-133-1162 (SEQ ID NO: 13, residues 133-1162; also shown in SEQ ID NO: 57)

PA4541-55-1417 (SEQ ID NO: 14, residues 55-1417; also shown in SEQ ID NO: 58)

PA4541-55-353 (SEQ ID NO: 14, residues 55-353; also shown in SEQ ID NO: 59)

RL2_PA4541-1027-1417_PA4541-55-353 (fusion between SEQ ID NO: 43, SEQ ID NO: 14, residues 1027-1414, and SEQ ID NO: 14, residues 55-353; also shown in SEQ ID NO: 60).

The survival of the immunized mice was compared to the survival of mice receiving immunological adjuvant only.

Materials

NMRI mice, female (Taconic, Denmark)

*Pseudomonas aeruginosa*, PAO1 (Iglewski batch #2 and #3.1)

Aluminum hydroxide (Alhydrogel 2.0%, 21645-51-2, Brenntag)

Freund's incomplete adjuvant (F5506-10X10ML, Sigma)

PA4877-1-135 (CBCBMJL07031401-11-75, Creative Biomart)

PA1870-2-141 (CB_CBMJL07031401-11-135, Creative Biomart)

PA0833-142-237 (CB_CBMJL07031401-11-145, Creative Biomart)

PA1011-20-396 (CBCBMJL07031401-11-84, Creative Biomart)

PA0428-1-639 (CB_CBMJL07031401-11-133, Creative Biomart)

PA4571-24-675 (CBCBMJL07031401-11-87, Creative Biomart)

RL2_PA4571-400-675_PA4571-24-191 (CB_CBMJL07031401-11-154, Creative Biomart)

PA3340-372-682 (CBCBMJL07031401-11-76, Creative Biomart)

PA3340-24-351 (CBCBMJL07031401-11-92, Creative Biomart)

RL2_PA0781-32-225_PA0781-515-687 (CB_CBMJL07031401-11-142, Creative Biomart)

RL2_PA0781-515-687_PA0781-32-495 (CB_CBMJL07031401-11-150, Creative Biomart)

PA0781-32-687 (CBCBMJL07031401-11-88, Creative Biomart)

RL2_PA0685-609-803_PA0685-1-339 (CB_CBMJL07031401-11-149, Creative Biomart)

PA1527-133-1162 (CB_CBMJL07031401-11-155, Creative Biomart)

PA4541-55-1417 (CBCBMJL07031401-11-86, Creative Biomart)

PA4541-55-353 (CB_CBMJL07031401-11-141, Creative Biomart)

RL2_PA4541-1027-1417_PA4541-55-353 (CB_CBMJL07031401-11-153, Creative Biomart)

Immunization Protocol

Female NMRI mice were immunized with the recombinant proteins listed above in combination with adjuvant. In every challenge setup, one group of 16 mice were immunized with adjuvant alone, making up the negative control group. The amount of adjuvant used for immunization of the control group was the same as the amount used when immunizing the protein-treated groups. Each mouse was immunized subcutaneously three times at approximately two week intervals. At all three immunizations, the mice in the protein-treated groups received 15 μg protein. For the first immunization, the proteins were mixed with aluminum hydroxide ($Al(OH)_3$) and Freund's incomplete adjuvant (IFA), whereas only $Al(OH)_3$ was used for the subsequent booster immunizations.

Preparation of Bacterial Inoculum

The bacteria used in the animal model of peritonitis were prepared in advance and frozen at −80° C. in aliquots; bacterial matter was streaked out on a Luria broth (LB) agar plate and incubated at 37° C. overnight. A single colony of *P. aeruginosa* was used for the inoculation of 50 mL of LB media. The culture was incubated at 37° C., with continuous shaking, overnight.

The following day 1 l of LB media was inoculated with 10 ml of the overnight culture, and incubated at 37° C. and continuous shaking for 6 hours. The bacterial suspension was centrifuged at 3,000×g for 10 minutes, and the pellet washed twice in 400 ml sterile PBS. After each wash the bacterial suspension was centrifuged at 3,000×g for 10 minutes. The bacterial pellet was resuspended in 10-15 ml PBS, and glycerol was added to a final concentration of 16%. The suspension was thoroughly mixed, aliquoted into 1 ml aliquots and stored at −80° C. The number of colony forming units (CFU) per ml was determined for the frozen stock, as aliquots were thawed on ice and serially diluted in sterile saline. The dilutions were plated on LB agar plates, and incubated at 37° C., overnight. The number of CFU per ml was established the following day. The procedure was carried out in duplicate, i.e. for two aliquots, to verify that the aliquots were homogenous.

Immediately prior to inoculation aliquots were thawed and diluted in sterile saline to the desired inoculum size, i.e. number of CFU per inoculum volume. After each inoculation, the inoculum size was confirmed by plating on LB agar plates.

Challenge Setup

The mice were housed at the Biomedical Laboratory at the University of Southern Denmark. The animals were kept in an environment characterized by a 12 hours light-dark cycle and temperature and humidity control. They had access to food and water ad libitum. The experimental procedures were carried out in accordance with the guidelines of the Danish National Animal Ethics Committee (license number 2015-15-0201-00680).

The experiments were performed in class 2 certified facilities at the Biomedical Laboratory. Two weeks after the third immunization the mice were inoculated intraperitoneally with a dose of *P. aeruginosa* PAO1 (Iglewski, batch #2 or 3.1) previously found to cause a 90% mortality of naïve mice. Following challenge, the mice were assessed daily to register symptoms and development of disease over the course of the 7 days. To ensure a consistent evaluation of all animals each animal was scored individually following the scale for clinical symptoms given in table 1.

TABLE 1

Scale of clinical symptoms.

| Score | Symptoms |
|---|---|
| 0 | No symptoms |
| 1 | Decreased spontaneous activity, slightly ruffled fur, weight loss maximum 10% |
| 2 | Decreased provoked activity, ruffled fur, weight loss maximum 15% |
| 3 | Symptoms like 1 or 2 and/or semi-closed eyes, decreased food and water uptake, weight loss maximum 20% |
| 4 | No activity when provoked, cold to the touch, no uptake of food and water, weight loss maximum 20% |

The mice were individually assessed on their physical appearance and behavior, noting the presence or absence of the given characteristics.

Humane Endpoints

Apart from the registration of clinical symptoms, body weight and temperature of each animal were registered daily following challenge. The weight loss was calculated as a percentage of the body weight registered prior to inoculation. Animals were euthanized if either of the following humane endpoints were reached: a body temperature below 25° C. (when measured with an infrared laser) or a weight loss above 20% of the initial body weight. Additionally, mice scored 3 over three successive days, without signs of improvements such as weight gain, or 4 once were euthanized.

Results

Survival Following Lethal Challenge

The survival of mice immunized with a protein in combination with the adjuvants Al(OH)$_3$ and IFA was compared to the survival of mice in the negative control group. FIGS. 1-18 show the survival curves for the different groups. The survival is also summarized in Table 2 below. The results derive from a total of 7 different studies. Only one protein, RL2_PA4541-1027-1417_PA4541-55-353, was tested in two independent trials.

TABLE 2

Survival of protein-immunized mice after a lethal challenge with *P. aeruginosa* PAO1.

| Protein ID | Survival control group | Survival protein-treated group | P-value |
|---|---|---|---|
| PA4877-1-135 | 7 of 16 | 3 of 12 (25%) | 0.1752 |
| PA1870-2-141 | 8 of 16 | 10 of 12 (83.3%) | 0.0788 |
| PA0833-142-237 | 6 of 15 | 10 of 12 (83.3%) | 0.0222 |
| PA1011-20-396 | 5 of 16 | 7 of 11 (63.6%) | 0.1322 |
| PA0428-1-639 | 5 of 16 | 7 of 12 (58.3%) | 0.1102 |
| PA4571-24-675 | 7 of 16 | 4 of 12 (23.3%) | 0.3669 |
| RL2_PA4571-400-675_PA4571-24-191 | 6 of 16 | 7 of 12 (58.3%) | 0.2457 |
| PA3340-372-682 | 6 of 16 | 9 of 11 (81.8%) | 0.0254 |
| PA3340-24-351 | 6 of 16 | 11 of 12 (91.7%) | 0.0037 |
| RL2_PA0781-32-225_PA0781-515-687 | 7 of 16 | 12 of 12 (100%) | 0.0022 |
| RL2_PA0781-515-687_PA0781-32-495 | 6 of 16 | 7 of 11 (63.6%) | 0.1363 |
| PA0781-32-687 | 5 of 16 | 7 of 12 (58.3%) | 0.1454 |
| RL2_PA0685-609-803_PA0685-1-339 | 6 of 16 | 9 of 12 (75.0%) | 0.0489 |
| PA1527-133-1162 | 6 of 16 | 8 of 12 (66.7%) | 0.1336 |
| PA4541-55-1417 | 7 of 16 | 10 of 12 (83.3%) | 0.0308 |
| PA4541-55-353 | 7 of 16 | 11 of 12 (91.7%) | 0.0132 |
| RL2_PA4541-1027_1417_PA4541-55-353 (first trial) | 9 of 16 | 11 of 12 (91.7%) | 0.0394 |
| RL2_PA4541-1027_1417_PA4541-55-353 (second trial) | 6 of 15 | 10 of 12 (83.3%) | 0.0222 |

The survival of the protein-treated mice was compared to the survival of mice in the negative control group, and log-rank (Mantel-Cox) was used to analyze the data.

Conclusions

Of the 17 proteins tested, 8 induced significant protection against a lethal *P. aeruginosa* infection. The protective candidates were PA0833-142-237, PA3340-372-682, PA3340-24-351, RL2_PA0781-32-225_PA0781-515-687, RL2_PA0685-609-803_PA0685-1-339, PA4541-55-1417, PA4541-55-353 and RL2_PA4541-1027-1417_PA4541-55-353.

SEQUENCE LISTING

```
Sequence total quantity: 67
SEQ ID NO: 1            moltype = AA  length = 135
FEATURE                 Location/Qualifiers
source                  1..135
                        mol_type = protein
                        organism = Pseudomonas aeruginosa
SEQUENCE: 1
MPRGDKSKYS DKQQRKAEHI EESYKAKGVS ESEAEARAWA TVNKQSGGGE RKGGSGRAKS   60
ETAKRADRKD SAHRAAQARS GRPANRGSAS RGKRQGSTSV SEMTREELMQ LARKRDIRGR  120
STMRKAELIE ALSRA                                                  135

SEQ ID NO: 2            moltype = AA  length = 138
FEATURE                 Location/Qualifiers
source                  1..138
                        mol_type = protein
                        organism = Pseudomonas aeruginosa
SEQUENCE: 2
MNILRIPMFV LAMAVSAHGF AATAQQEKMT ACNAEATTKA LKGDERKAFM SGCLKAGAPA   60
```

```
GGKATAQQEK MKSCNADASA KSLKGDERKA FMSSCLKAGG SAKAATQQEK MKTCNADATA    120
KALKGDERKA FMSTCLKK                                                 138

SEQ ID NO: 3              moltype = AA   length = 141
FEATURE                   Location/Qualifiers
source                    1..141
                          mol_type = protein
                          organism = Pseudomonas aeruginosa
SEQUENCE: 3
MATRRKTTPQ EIDDIQDRMG SMRELDFDER RQARKARIGD ERPEAEVEAE FSSRRVREAG    60
HAGGQPDEDD GYQDNVGMDD LAPETLIDES GARSPAERGG ESPADKRLRV VHGNEIGAGH    120
GLDEAELARR DPLDGSSDEE R                                             141

SEQ ID NO: 4              moltype = AA   length = 150
FEATURE                   Location/Qualifiers
source                    1..150
                          mol_type = protein
                          organism = Pseudomonas aeruginosa
SEQUENCE: 4
MRRMILPASL LLALSSFAMA APIYKWVDAE GVTHFGAQPP QGAQATTVNT QTAPPPDNFP    60
LPPSTPAPTI QQKPADPEQK AIDDVKQQV AKEEAERKQF CEETRNNLAQ LKNNPRVRVD     120
EGKGELRRLG EEERQERIAK AEKAIQENCR                                    150

SEQ ID NO: 5              moltype = AA   length = 237
FEATURE                   Location/Qualifiers
source                    1..237
                          mol_type = protein
                          organism = Pseudomonas aeruginosa
SEQUENCE: 5
MFTSRCLPLA AAVTALALLA GCANNNPYDT QSQSQGGMSK TAKYGGLGAL AGAVAGAAID    60
HNNRGKGALI GAAVAGAAAA GYGYYADKQE AELRRQMEGT GVEVQRQGDD IKLIMPGNIT    120
FATDSANIAP SFYAPLNNLA NSFKQYNQNT IEIVGYTDST GSRQHNMDLS QRRAQSVAGY    180
LTAQGVDGTR LSTRGMGPDQ PIASNSTADG RAQNRRVEVN LRPVPGAQGP AQTQPQY      237

SEQ ID NO: 6              moltype = AA   length = 396
FEATURE                   Location/Qualifiers
source                    1..396
                          mol_type = protein
                          organism = Pseudomonas aeruginosa
SEQUENCE: 6
MKRLAGLTAL ALVIGNTSGC GWLWGPEGYF RDRGDDYLGA RETPPMQLPE GVHSKPLDPL    60
LPIPLNVATT HEKEGEYEVP RPQPLANAGD ISDYSLQRSG DSRWVVAQRP PAEVWPVARQ    120
FFEENGFRIA DERPQTGEFS SDWQSLSQLS APLARRLSSR VSGVEPDGQA RVRVRIEPGV    180
QSNTSEVYVL SQTRAAGDTS SPSWPSKSVA PSLDAALLDE MVASMARSAE QGGSVSLLAA    240
NSIYDTPGTF ELSKDGSGNP VLTLQSDFDR SWVSVGRALD NADIRVDDLN RSLGVYYVNI    300
AEGAKKPDED KPGFFSRLFG GGEKTKEEED AKAQRYQVRL TTVSDAVQVT VDKDINTSAP    360
ADVAQNVLEK LQESMRNAVR GSGQRKPGQF GLGEQF                             396

SEQ ID NO: 7              moltype = AA   length = 543
FEATURE                   Location/Qualifiers
source                    1..543
                          mol_type = protein
                          organism = Pseudomonas aeruginosa
SEQUENCE: 7
MIRLFCSLLL ALLCVSAHAS FSASVDRARL TEGESVELTL ESDDPTLFGK PDLSPLDALF    60
EVLGTRQVNR LATQNGRAQA TTRWIVTLLP KQSGYVAIPP ISLGASSTQP IRLHVLEARD    120
RAKSSKLAPV FIDASVDQET VYVQAQAILT LRIYHSVSLY DDSSLTPLAM NDAKVEQLGE    180
ARTYEKEING IRHGVIEVRY AIFPQKSGTL EIPAQAFSAT LVDRGSDDYN PFGPRPGRQM    240
RVTSPSIPLQ VRPKPADYPA DAPWMPARAL SISESWSPQP EQAQVGESLT RNVLLKVEGL    300
SGTQLPPLPL PDVQGLRRYP DQPQLADQST DQGLIGSREE REALVPEQAG RIELPALEVV    360
WWNTREDRLE RTSLPPRTLE VAAAPQAEAE PPAAALPLGE RLEPTLWPWQ LATAVLALTT    420
LLGFGLWWRA RQLPAVIRAA ANGPSSRSLL DELRRACLAN DPQATRQALD AWARQQPDTL    480
ADMAARFVPL SDALDGLNGA LYSESGHSWQ GEDLWRAIRA LPTTEQAPAG AVDNGGLPPL    540
YPR                                                                543

SEQ ID NO: 8              moltype = AA   length = 639
FEATURE                   Location/Qualifiers
source                    1..639
                          mol_type = protein
                          organism = Pseudomonas aeruginosa
SEQUENCE: 8
MSFSSLGLSE ALARAVEAAG YSQPTPVQQR AIPAVLQGRD LMVAAQTGTG KTGGFALPVL    60
ERLFPAGHPD REHRHGPRQA RVLVLTPTRE LAAQVHDSFK VYARDLPLNS TCIFGGVGMN    120
PQIQALAKGV DVLVACPGRL LDLAGQNKVD LSHVEILVLD EADRMLDMGF IHDVKKVLAK    180
LPPKRQNLLF SATFSKDIVD LANKLLHNPE RIEVTPPNTT VERIEQRVFR LPAPQKRALL    240
AHLVTVGAWE QVLVFTRTKH GANRLAEYLT KHGLPAAAIH GNKSQNARTK ALADFKANDV    300
RILVATDIAA RGLDIDQLPH VVNYELPNVE EDYVHRIGRT GRAGRSGEAI SLVAPDEEKL    360
LKAIEKMTRQ RIPDGDAQGF DPEAVLPEVA QPEPREAPQK QPRRDKERRS SRERKPKDAQ    420
ASNPDSNVAA AQDGTEKPAG KRRRRGGKNK ENREAGQAQQ PRQSREARPA KPNRPPEVDG    480
```

```
NRDPEEFLDD DFDNFGNRAD YVSPYQGQEN KGRGRRGGQQ KPQGGTGQQG RGQGQGQARG    540
KSQGAAQGGA RGQGAGQGKA KKPRAGKPRG QGRENASRMS DAPLREPSEY GTGKQPSRQP    600
VVINKRDLVR MDRFPTAEQL DELEPRRKGE RPALLTRNR                          639

SEQ ID NO: 9             moltype = AA   length = 675
FEATURE                  Location/Qualifiers
source                   1..675
                         mol_type = protein
                         organism = Pseudomonas aeruginosa
SEQUENCE: 9
MPASFPRLGL LGALCSIVPL LHASEPTTDA ALIEKGRYVA QLGDCIACHT GPQGAPMAGG    60
LELKTPMGTI YSTNITPDRE TGIGRYSFEE FDRAMRKGVT AEGVNLYPAM PYPSYAKISE    120
EDMRALYAYL MHGVQPVTQA NTPSAMSWPF NQRWGLSLWN WAFLDDAPFT PSSDADPVIN    180
RGAYLVQGLG HCGACHTPRG IAFQEKAMSE AGRSGQFYLA GETVEQWQAL SLRNLWTVED    240
TVQLLKTGQN RFATVSGSMT DVIHHSTQHF SDDDLLAIAS YLKSLPAGKD DLPMPDSERP    300
LAAPVDLYSS RGGLGYAQFC SDCHRKDGSG VPGMFPPLAG NPTVASANPS TLLHITLTGW    360
KTAQTATHSR VYTMPGFAQL EDREIAEILS FVRSSWGNQG SSIDAGQVKK LRQRIEAGNG    420
PATTFVSPRL ADMLAAPNAE QVVRGMRLHL ETRELLPANV GNQLHCTSCH LNAGTVADGS    480
PFVGVSAFFP SYAPRAGKVI GLEERINGCF RRSMNGKPLP PDSADMQAMV AYFDWMKNNT    540
RPQDKVAGRG VGKVDPALKP DPENGRKVYA RQCVVCHGEN GEGLRNSAGE MLFPPLWGDE    600
SFNIGAGMAR TFTAAAFVKH NMPIGFQERF PLGQGGLSDQ DAVDVAEYFS HQPRPDFPDK    660
IKDWPKDKRP LDARY                                                    675

SEQ ID NO: 10            moltype = AA   length = 682
FEATURE                  Location/Qualifiers
source                   1..682
                         mol_type = protein
                         organism = Pseudomonas aeruginosa
SEQUENCE: 10
MPGKALRVML CAWSCLLAGQ ASALGVGDII LHSALNQPLD ADIELLDVGD LGADEIEVRL    60
AGADVFAAAG VERLQFLNEL RFSPVLQGRG GNRIHVSSIR PVQEPYLNFL VEVARPNGRI    120
VREFTVLLDP LGYTPRMLPA ARSGIEPQRQ SSTPVPAPRS AAVVVDPALL EPGDEYLARP    180
SDNLWAISGR LRGAGNADRA QLMEALYQLN PQAFVNADRH RLKAGARLRL PAGYQPERGA    240
PGAVKEAAVE VLPPADAAVV ENAPAALVEA QRQADAEAEA LARQREELSQ RMDDLQRQLQ    300
ALQEQLQQRD HQVAELQQQL ARRQAVRPAA PPPAAAAPSV AQPVETPTDS QYWRWMIVLL    360
LVLALLGVLL LRRRREEAPV PAVEPKRRVA LNLPLRRAPR PPAAAPAPAK VEEQARPPVA    420
APSSPPPSPP PAPAAAPRAA MAAADKLDGA DIYIAYGRYG QARDLLRQVL AEQPQRLSAR    480
MKLLLVLAEL GDAAGFDALA EETLASGGNP EAIDELRGRY PALLQMPATE TPAATTKDDD    540
WSDLPLAESP VLQQPDATSG ADGFGDLNLD LDLDWGALEN PLDNPDLRRR AAAGKAEPAE    600
EPLAFESNLH ELPDVAEYEH LELDQPEPAT VPPEEASASL DRARACIDSG DLDQASRILR    660
LVVAHGDPWQ KAEARELLAL IA                                            682

SEQ ID NO: 11            moltype = AA   length = 687
FEATURE                  Location/Qualifiers
source                   1..687
                         mol_type = protein
                         organism = Pseudomonas aeruginosa
SEQUENCE: 11
MSSSGLFPSR PLWPLTPLAL ACLIVSGETL GADGRPSELP SQVITANPLG NESPATPSSV    60
LEGDELTLRQ KGSLGETLNG LPGVSSTYFG PGASRPVIRG MDGDRIRLLR NGVGALDASS    120
LSYDHAVPED PNSVERLEVV RGPAALLYGG NAIGGVVNSF DNRIPSEPVD GIHGSGELRY    180
GGADTTRSRS GALEAGDGNF ALHVDAASRE FNDVRIPGYA HSSRQRQIDG DTGKHRVQNS    240
DGRQDGGAVG GSYHWEHGYA GLSYSGYDSN YGSPAEDDVR LKMQQDRYAF ASEIRDLEGP    300
FTSLKLDAAY TKYEHKEIED GETGTTFKNE GYEGRIEARH RPLGPLNGVV GAQFANSRFS    360
ALGEEAFVPH TETDSAALFA LEEWKLSDRL DLSFGARLEH TRVDPDAKGN ERFAENDGSQ    420
SFTTGSLSTG AVYKLTPIWS LAATLSYTER APTFYELYAN GPHAATGTYE VGDADADKEK    480
AVSTDLALRF DNGVHKGSVG VFYSRFSNYI GLLASGRHRN EEGEVVAAGD DEALPEYLYS    540
GVRADFGYGE AQDRIHLLES PYGNFDLELS GDYTRAKNKD TGEPLPRIAP LRLNTALIWE    600
LQQWQARVDV EHAASQHRVP EEELSTDGYT TLGASLGYNF DLGESRWLAF VKGTNLTNQT    660
VRYASSILRD RVPAAGRGIE AGVKVAF                                       687

SEQ ID NO: 12            moltype = AA   length = 803
FEATURE                  Location/Qualifiers
source                   1..803
                         mol_type = protein
                         organism = Pseudomonas aeruginosa
SEQUENCE: 12
MRQSAPHHAR RRWPVLGVAL GALLVAACSE TPKVPGVPPA DEEVGRPLSS VRSGAPLRSA    60
DVRERPQAEQ ARRALSAGRG VARSGGVAPV SATAAELGEQ PVSLNFVDTE VEAVVRALSR    120
ATGRQFLVDP RVKGKLTLVS EGQVPARTAY RMLTSALRMQ GFSVVDVDGV SQVVPEADAK    180
LLGGPVYGAD RPAANGMVTR TFRLRYENAV NLIPVLRPIV AQNNPINAYP GNNTVVVTDY    240
AENLDRVAGI IASIDIPSAS DTDVVPIQNG IAVDIASTVS ELLDSQGSGG AEQGQKTVVL    300
ADPRSNSIVI RSPSPERTQL ARDLIGKLDS VQSNPGNLHV VYLRNAQATR LAQALRGLIT    360
GDSGGEGNEG DQQRARLSGG GMLGGGNSGD GSQGLGSSGN TTGSGSSGLG GSNRSGGAYG    420
AMGSGQGGAG PGAMGEENSA FSAGGVTVQA DATTNTLLIS APEPLYRNLR EVIDLLDQRR    480
AQVVIESLIV EVSEDDSSEF GIQWQAGNLG GNGVFGGVNF GQSALNTAGK NTIDVLPKGL    540
NIGLVDGTVD IPGIGKILDL KVLARALKSR GGTNVLSTPN LLTLDNESAS IMVGQTIPFV    600
SGQYVTDGGG TSNNPFQTIQ REDVGLKLNI RPQISEGGTV KLDVYQEVSS VDERASTAAG    660
VVTNKRAIDT SILLDDGQIM VLGGLLQDNV QDNTDGVPGL SSLPGVGSLF RYQKRSRTKT    720
```

```
NLMVFLRPYI VRDAAAGRSI TLNRYDFIRR AQQRVQPRHD WSVGDMQAPV LPPAQQGIPQ   780
AAYDLRPSPR PLRAVPLGEA APL                                           803

SEQ ID NO: 13               moltype = AA   length = 1162
FEATURE                     Location/Qualifiers
source                      1..1162
                            mol_type = protein
                            organism = Pseudomonas aeruginosa
SEQUENCE: 13
MRLKSIKLAG FKSFVDPTTV NFPSNMAAVV GPNGCGKSNI IDAVRWVMGE SSAKNLRGES    60
MTDVIFNGSN TRKPVSQASI ELIFDNAETT LVGEYAQYAE ISIRRRVSRD GQNTYFLNGT   120
KCRRRDITDI FLGTGLGPRS YSIIEQGMIS KLIEARPEDL RNFIEEAAGI SKYKERRRET   180
ESRIRRTQEN LARLTDLREE LGRQLERLHR QAQSAEKYQE HKAEERQLKA QLGAVRWRDL   240
NEQVGQRERV IGDQEIAFEA LVAEQRGADA GIERLRDGHH ELSERFNQVQ ARFYSVGGDI   300
ARVEQSIQHG QQRQRQLQDD LREAERTRQE TESHLGHDRT LLATLAEEMA MLAPEQELSA   360
AAAEEAGIAL EQAEQGMQAW QQQWDAFNQQ SAEPRRQAEV QQSRIQHLEQ SLERLQDRER   420
RLQEERGQLA ADPEDAAILE LNEQVAIAEL ALEELQLQEQ GQAERLEQLR QELQQLAAEQ   480
HQAQGELQRL NGRIASLEAL QQAALDPGQG ALEWLREQGL EQRPRLAEGL RVEPGWELAV   540
ETVLGADLQA VLLDGFDGLA LAGFGKGELR LLSPARGAAT AAGSLLDKVR ADADLSPWLA   600
RVKPVETLEQ ALAQRGALDD GESLISRDGY WVGRHFLRVR RSDEAQGGML ARAQELEALQ   660
ERREALETRV AEGEERLAAA RDEQRELEGA REQVRRQVQE EGRRHGELKA QLSAQQAKVE   720
QLVLRRRRLD EEVAELAEQR ALEQEQLSEA RLTLQEALDS MALDTERRES LAAERDALRE   780
RLDRIRQDAR THKDHAHQLA VRVGSLKAQH NSTQQALERL DQQSARLNER CEQLNLNLEE   840
GAAPLEELRM KLEELLERRM AVEDELKQAR LALEDADREL REVEKRRGQA EQQSQLLRGQ   900
LEQQRLEWQG LVVRRKALQE QLAEDGYDLH TVLANLPLDA SERDWEERLE SLAARIQRLG   960
PINLAAIEEY QQQSERKRYL DSQNDDLAEA LETLENVIRK IDRETRNRFK ETFDQINAGL  1020
QALFPKVFGG GTAYLELTGE DLLDTGVAIM ARPPGKKNST IHLLSGGEKA LTALALVFAI  1080
FQLNPAPFCM LDEVDAPLDD ANVGRYARLV KEMSEKVQFI YITHNKIAME MADQLMGVTM  1140
HEPGCSRLVA VDVEEAVALA EA                                           1162

SEQ ID NO: 14               moltype = AA   length = 1417
FEATURE                     Location/Qualifiers
source                      1..1417
                            mol_type = protein
                            organism = Pseudomonas aeruginosa
SEQUENCE: 14
MNKSYTLVWN QATGCWNVAS EGTRRRSKSG RGKALVVAGA SLLGLFCQAP AFALPSGATV    60
VSGDAGFQTS TDGRHMVIDQ QSHKLITNWN EFSVRADERV SPHQPGQDAV ALNRVIGRNG   120
SDIQGRIDAN GKVFLVNPNG VVFGKSAQVN VGGLVASTLD LADRDFLAGN YQFSGDSGAT   180
VSNAGSLQAS EGGSIALLGA RVSNDGLIQA QLGDVALGAG QGINLNFDGD GLLNLQVDKG   240
SVDALAHNGG LIRADGGQVL MSARSADSLL KTVVNNQGTL EARTLRSAEG RIVLDGGEQG   300
TVRVAGKQDA SAIGGGNGGL VLNQGANVEI QRTAQVDTHA DQGATGTWRI LSHEVSVAAV   360
GQANAAGDGS GQVHVAQGPA GANASDSNGV TIVQQQPAVD LAAGANGTSA VQSQSGANIG   420
SGANGISVVQ SQNSPNIGSG ANGISVVQSQ NGANIGAGAS GISVVQSQNS PNIGSGVNGV   480
TVVQSQNGAN IGSGASGITV VQSQNGANIG SGASGISVVQ SQSGPSIGSG VNGVTIVQSQ   540
SGANIGPGVS GIDVVQTQTL PNLSPGANGS SIVQVQTLPD IAADAGNVHV VQVQTGGNKV   600
FGNSATNVRS RTVQARSNEN VGSGLANPSS AGKGSTLHAD TLARNLSTSN VEVVATRGNA   660
HVGAPLSWDS GNGLTLTAER GDLRINGALT AQGENASLTL NAGQRPLRID DSLSLTGQGA   720
RVEFNSDKGY ALAEGTRITL SGKNAGFRAN GRDYSVIQDL QQLRGIDRDL GGSYVLGNRI   780
AGGNSSFLSI GNASAFGGTF DGLGNTIDNL AVYGTGAYSG LFSVNRGTLR NLNLERISAD   840
GAQATHYNVQ VGSLAAVNLG RIDNVNASDI RIAAASKLNS LGGLVALNLG SIDNASASGT   900
LVGNRHTYAL GGLAAENIST ARGVASISNS RADFAISGQL KDHASHYGAG GLVGRNRGGL   960
IRSSGSQGTL SLSGHGMNLG GLVGYSSAGG LADVSASVDV SGNGQRGLYG GLIGLNVNSG  1020
IAHATASGKV RGTDAEALGG LIGRNLNAAI NNASAHGDVS LQAGRYLGGL IGHNQAGNLA  1080
NVSTSGNLSG GSLLQAGGLI GLNANASLVN ASAKGNVATR GAEAVGGLLG ENLYGSVING  1140
SASGEVTDGS GKTLGGLIGS NLGGNHSNLK ASGWVNAGAN SDVGGLIGHN RGGNHSTLAA  1200
SGNVTGGKGS RVGGLVGYND AASLTNVSAS GNVSASGSRA IGGLIGSDLR GSLMLASSHG  1260
IVNDKTSHNL GGLVGRGENT SIRSAKASGA VSGGAGIRAG GLVGSLEGWQ ALILGASAGG  1320
DVTAGYDSYI GGLVGFSTAT ISGASASGKV GGSGLLGGLV AWNQGNVMGS SASGRLEPQI  1380
PNQIHGGLIG INFGWQSWNS VYGAAATVPM IGRHYNL                           1417

SEQ ID NO: 15               moltype = DNA   length = 408
FEATURE                     Location/Qualifiers
source                      1..408
                            mol_type = genomic DNA
                            organism = Pseudomonas aeruginosa
SEQUENCE: 15
atgccccgtg gcgacaagag caagtacagc gacaagcagc agcgcaaggc cgagcacatc    60
gaggagagct acaaggccaa gggtgtgagc gagtcggaag ccgaggcgcg cgcctgggcg   120
acggtgaaca agcagtccgg cggcggcgag cgcaagggcg gttccggccg cgccaagagc   180
gagacggcca agcgcgccga ccgcaaggac tcgcccatc gcgccgccca ggcccgctca    240
gggagaccgg ccaaccgcgg ctcggcgagc cgtggcaaac gtcaaggcag cacctcggtg   300
agcgagatga cccgcgagga attgatgcag ctggcgcgca agcgcgacat ccgcggtcgt   360
tcgacgatgc gcaggccga actgatcgag gccctgtccc gggcctga                 408

SEQ ID NO: 16               moltype = DNA   length = 417
FEATURE                     Location/Qualifiers
source                      1..417
                            mol_type = genomic DNA
```

-continued

```
                              organism = Pseudomonas aeruginosa
SEQUENCE: 16
atgaatatcc tgcgtatccc gatgttcgta ttggccatgg ccgtctcggc ccatggtttc   60
gctgccaccg cgcagcagga gaagatgacc gcctgcaacg ccgaggccac caccaaggcg   120
ctcaagggcg acgaacgcaa ggcgttcatg agcggctgcc tgaaggccgg cgcgcctgcc   180
ggcggcaagg ccaccgccca gcaggagaag atgaagagct gcaacgccga cgccagtgcc   240
aagtcgctca agggcgacga acgcaaggcg ttcatgagca gttgcctgaa ggccggcggc   300
agcgccaagc cggcgaccca gcaggagaag atgaagacct gcaacgccga cgccaccgcc   360
aaggcgctca agggcgacga acgcaaggcg ttcatgagca cctgcctgaa gaagtga      417

SEQ ID NO: 17          moltype = DNA   length = 426
FEATURE                Location/Qualifiers
source                 1..426
                       mol_type = genomic DNA
                       organism = Pseudomonas aeruginosa
SEQUENCE: 17
atggctacac gacggaaaac aacaccccag gaaatcgatg atatccagga ccgcatgggt   60
tcgatgcgcg agctcgattt cgacgagcgc cgccaggcgc gtaaggcgcg gatcggcgac   120
gagcggcccg aggccgaggt ggaggccgaa ttttcctcgc ggcgggtacg cgaggcgggc   180
cacgctggcg ggcagccgga cgaggacgat ggttaccagg ataacgtcgg catggacgat   240
ctggcgccgg aaaccctgat cgacgaaagc ggcgcccgct cgccggccga gcgcggcggc   300
gaatcgcccg cggacaagcg cctgagggtc gtgcatggca acgagatcgg agccggccac   360
ggcctcgacg aggccgagct ggcgcgtcgt gatccgctcg acgttcctc cgacgaggaa   420
cgctga                                                              426

SEQ ID NO: 18          moltype = DNA   length = 453
FEATURE                Location/Qualifiers
source                 1..453
                       mol_type = genomic DNA
                       organism = Pseudomonas aeruginosa
SEQUENCE: 18
atgcgacgca tgatcctccc ggccagcttg ttgctcgccc tctcctcttt cgccatggcc   60
gccccgatct acaaatgggt cgacgccgag ggcgtcaccc acttcggcgc acaaccgccg   120
caaggtgcgc aagcgaccac ggtgaatacc cagaccgccc cgccgccgga caacttcccc   180
ctgccccct cgaccccggc accgaccatc cagcagaaac cggccgatcc cgagcagaag   240
gcgatcgacg acaaggtgaa gcagcaagtg cgcaaggaag aggccgagcg caagcagttc   300
tgcgaagaga cccgcaacaa cctcgcgcaa ctgaagaaca acccgcgcgt aagggtcgac   360
gaaggcaagg gcgaactccg tcgcctcggc gaggaagaac gccaggagcg aatcgccaag   420
gccgaaaagg cgatccagga gaattgccgc tga                                453

SEQ ID NO: 19          moltype = DNA   length = 714
FEATURE                Location/Qualifiers
source                 1..714
                       mol_type = genomic DNA
                       organism = Pseudomonas aeruginosa
SEQUENCE: 19
atgttcacct cccgttgcct gcctctggcc gcagccgtca ccgcactggc gctgctcgcc   60
ggttgtgcca acaacaaccc ctacgacacg caaagccaaa gccagggtgg catgagcaag   120
acggccaagt acggcggact gggtgcgctg gccggcgccg tcgccggcgc tgcgatcgac   180
cacaacaacc gtggcaaggg cgcgctgatc ggcgctgccg ttgccggcgc ggccgccgcg   240
ggttatggct actacgccga caagcaggaa gccgagctgc gtcggcagat ggaaggcaac   300
ggcgtggaag tgcagcgcca aggtgacgac atcaagctga tcatgccggg caacatcacc   360
ttcgccaccg attcggcgaa catcgccccg agcttctacg cgccgctgaa caacctggcg   420
aactcgttca agcagtacaa ccagaacacc atcgagattg tcggttacac cgacagcacc   480
ggcagccgcc agcacaacat ggacctgtcc cagcgtcgtg cgcagagcgt ggccggctac   540
ctgaccgccc agggcgtcga cggccaccgc ctgagcaccc gcggcatggg cccggaccag   600
ccgatcgcga gcaactccac tgccgacggt cgcgcgcaga accggcgcgt cgaggtcaac   660
ctgcgaccg ttccgggcgc ccagggcccg gcgcagaccc agccgcagta ctga          714

SEQ ID NO: 20          moltype = DNA   length = 1191
FEATURE                Location/Qualifiers
source                 1..1191
                       mol_type = genomic DNA
                       organism = Pseudomonas aeruginosa
SEQUENCE: 20
atgaagcgac tggctggact gaccgccctc gccctggtta tcggcaacac ttccggctgc   60
ggctggctgt gggggccgga gggctatttc cgcgaccgcg gtgacgacta cctcggcgcc   120
cgcgaaacgc ctcccatgca attgcccgaa ggggtgcaca gcaagccgct cgatccgctg   180
ctgccgattc cgctgaacgt cgccaccacc cacgaaaaag agggtgagta cgaggttccg   240
cgtccgcagc cgctgccaa cgccggcgac atcagcgact acagcctgca gcgcagcggt   300
gatagccgct gggtcgtggc ccagcgtccg ccggcggaag tctggccggt ggcccggcag   360
ttcttcgagg agaacggttt ccgcatcgcc gacgagcgcc cgcagaccgg cgagttcagt   420
tccgactggc aatcgctgtc gcagctttcc gcgccgctgg cacgccgcct tagcagccgc   480
gtgagcggtg tcgagcaggc cggccaggca cgggttcggg tgctgtatga gcccggcgtg   540
caaagcaata ccagcgaggt ctacgtgctc agccagaccc gcgccgccgg tgacaccagc   600
agcccgagct ggccgagcaa gtcggtggcg ccgagcctcg acgcggcgct gctcgacgag   660
atggtcgcga gcatggcgcg cagcgccgag cagggcggct cggtctccct gctggcagcc   720
aactcgatct acgacacgcc cggcaccttc gagttgagca aggacggcag cggcaacccg   780
gtgctgacct tgcagtccga cttcgaccgc tcctgggtca gcgtcgggcg tgccctggat   840
```

-continued

```
aacgccgata tccgcgtcga cgacctcaac cgcagccttg gcgtgtacta cgtgaacatc   900
gccgaagggg cgaagaagcc cgacgaagac aagcccgggt tcttcagtcg cctgttcggc   960
ggcggcgaga agaccaagga agaggaagac gccaaggcgc agcgctacca ggtccgcctg  1020
accaccgtca gcgacgccgt gcaggtcacc gtcgacaagg acatcaacac ctctgcgccg  1080
gccgatgtcg cgcaaaacgt actggaaaaa ctccaggaga gcatgcgcaa tgcggttcgc  1140
ggttctgggc agcggaagcc ggggcaattc ggccttggtg agcagttctg a           1191

SEQ ID NO: 21          moltype = DNA  length = 1632
FEATURE                Location/Qualifiers
source                 1..1632
                       mol_type = genomic DNA
                       organism = Pseudomonas aeruginosa
SEQUENCE: 21
atgatccgcc tgttctgcag cctgcttctc gcgctcctct gcgtctccgc ccacgccagc    60
ttcagcgcca gcgtcgaccg cgcccgcctg accgaagggg aaagcgtcga actgacgctg   120
gaatcggacg acccgaccct cttcggcaag cccgacctga gcccgctgga cgccctcttc   180
gaggtcctcg gcacgcgcca ggtcaaccgt ctcgccacac agaacggccg ggcccaggcc   240
accaccgct ggatcgtcac cctcctgccg aagcagagcg gctacgtggc gatcccgccg   300
atcagcctcg gcgccagcag cacccagccg atcaggctgc acgtactgga ggcgcgcgac   360
cgcgccaaga gcagcaagct ggcgccggtc ttcatcgatg ccagcgtcga ccaggagacg   420
gtctacgtgc aggcccaggc gatcctcacc ctgcgcatct accactcggt gtcgctatac   480
gacgacagca gcctgacccc gctggcgatg aacgacgcga aggtcgaaca gctcggcgag   540
gcgcgcacct acgagaagga gatcaacggc atccgccacg gcgtgatcga ggtgcgctac   600
gcgatcttcc cgcagaagag cggcaccctg gagattcctg cgcaagcctt cagcgcgacc   660
ctggtcgacc gtggcagtga cgactacaac cccttcggcc cgcgccccgg ccggcagatg   720
cgggtgactt cgccgagcat cccgctgcag gtccggcccg agcctgccga ctatccgcag   780
gacgcgccct ggatgccggc ccgcgcgctg agcatcagcg aaagctggag cccgcagccg   840
gagcaggcgc aggtcggcga atcgctgacg cgcaatgtgc tgctgaaggt cgaggggctt   900
tccggcaccc agcttccgcc gttgccgctg cccgacgtgc aaggcctgcg cgcctaccccg   960
gaccaaccgc agttggccga ccagagcacc gaccagggcc tcatcggcag tcgcgaggaa  1020
cgcgaggcgc tggtgcccga gcaggccggg cgcatcgagt tgccggcgct cgaagtggtc  1080
tggtggaaca cccgcgaaga ccgcctggag cgcaccagce tgccaccgcg caccctggaa  1140
gtggccgccg cgccgcaggc cgaggcggag ccgccggcgg cggcgctgcc gctcggcgaa  1200
cgcctggagc cgacgctctg gccctggcaa ctggctaccg ccgtgctggc cctgaccacc  1260
ctgctcggct tcggcctctg gtgggcgcgcc cgccagctgc ggcggtgat ccgcgccgcg  1320
gccaacggcc cgagcagccg cagcctgctc gacgagctgc gccggcgctg cctgccaac  1380
gatcccagg cgaccgcca ggccctggac gcctgggccc gtcagcaacc cgataccctg  1440
gccgacatgg cggcccgctt cgtaccgctg tccgacgccc tggatggcct caacggcgcg  1500
ctgtacagcg agagcggcca ttcctggcag ggcgaggacc tgtggcgggc gatccgcgcc  1560
ctgcccacca cggaacaagc gccggcggga gcggtcgaca atggcggcct gccaccgctc  1620
tatccgcgct ga                                                       1632

SEQ ID NO: 22          moltype = DNA  length = 1920
FEATURE                Location/Qualifiers
source                 1..1920
                       mol_type = genomic DNA
                       organism = Pseudomonas aeruginosa
SEQUENCE: 22
atgtccttt cttccctcgg actctccgag gcgcttgccc gcgctgtgga ggctgcgggc    60
tacagccagc ccactcccgt gcaacagcgg gcgattcccg ccgtgttgca aggtcgcgac   120
ctgatggttg cggcacagac cggcaccggc aagaccgatg gtttcgccct gccggtactg   180
gagcgcctgt tccccgccgg tcatcccgac cgcgaacacc gccacggccc gcgccaggcg   240
cgcgtgctgg tactgacccc gacccgtgag ctggccgccc aggtgcatga cagcttcaag   300
gtctacgccc gcgacctgcc gctgaacagc acctgcatct tcggtgggt tggcatgaac   360
ccgcagatcc aggccctggc caaggcgtc gacgtactcg tcgcctgccc cggccgcctg   420
ctcgacctgg ccgggcagaa caaggtcgac ctgtcccacg tggaaatcct cgtcctcgac   480
gaagccgacc gcatgctcga catgggcttc atccacgatg tgaagaaggt tctcgccaag   540
ctgccgccca agcgccagaa cctgctgttc tcggcaacct tctcgaaaga catcgtcgac   600
ctcgccaaca agctcctgca caacccgaa cgcatcgagg taacgccgcc gaacaccacg   660
gtcgagcgca tcgagcaacg cgtgttccgc ctgccggctc cgcagaagcg cgccctgctg   720
gcgcacctgg taaccgtcgg cgcctgggaa caggtgctgg tcttcacccg taccaagcac   780
ggcgccaacc gtctcgccga gtacctgacc aagcacggcc tgccggccgc cgcgatccat   840
ggcaacaaga gccagaacgc gcggaccaag gcgctggccg acttcaaggc caacgacgtg   900
cgcatcctgg tggcgaccga catcgccgcc cgcggcctgg atatcgacca gttgccccat   960
gtggtcaact acgagctgcc caacgtcgag gaagactatg tccaccgcat cggccgtacc  1020
ggccgagccg gacgcagcgg cgaggcgatc tcgctggtgg cgccggacga agagaagctg  1080
ctcaaggcca tcgagaagat gaccagacag cgtattcccg atggcgatgc ccaggggttc  1140
gaccccgagg ccgtgctgcc cgaggtggcc cagccggagc cccgcgaagc cgcagaag  1200
cagccgccgc gcgacaagga acggcgcagc agccgcgcag gcaagccgaa agacgcccag  1260
gcgagcaacc ccgacagcaa tgtcgctgcg gcccaggacg gtaccgagaa gccggctgga  1320
aagcgccgcc gtcgcggtgg caagaacaag gaaaaccgcg aggccggcca agcgcagcag  1380
ccgcggcaga gccgcgaagc gcgtccggcc aagcccaatc ggccgccgga gtcgacggt  1440
aatcgcgatc cggaagagtt cctcgacgac gacttcgaca atttcggcaa ccgcgccgac  1500
tacgtcagcc cctaccaggg ccaggaaaac aagggacgcg aggccgggg tggccagac  1560
aaaccccagg cgcgcaccgg ccagcagggt cgtggccaag gccagggcca agctcgcggc  1620
aagagccagg cgcgcgctca aggcggcgct cgcggtcagg gtgccggcca gggcaaggcg  1680
aagaaaccgc gcgccggcaa gccgcgcggc caggtcgcg agaatgcctc gcggatgagc  1740
gacgcgccgc tgcgcgagcc gtccgagtat ggcaccggca agcagccgag ccgccagccg  1800
gtggtgatca acaagcgcga cctggtgcgc atggatcgct tccccaccgc cgagcagctc  1860
```

-continued

```
gacgagctgg aaccgcggcg caagggcgag cgccccgcac tgctgacccg caaccgctaa  1920

SEQ ID NO: 23         moltype = DNA  length = 2028
FEATURE               Location/Qualifiers
source                1..2028
                      mol_type = genomic DNA
                      organism = Pseudomonas aeruginosa
SEQUENCE: 23
atgcctgctt ctttcccgcg cctcggcttg ctcggcgcac tgtgctccat cgttcccctg  60
ctccatgcca gcgaaccgac cacggacgct gcgctcatcg aaaaaggccg ctacgtggcc  120
cagctcggcg actgcatcgc ctgccatacc ggcccgcagg gcgcgccgat ggccggcggc  180
ctggagctga agacgccaat gggtaccatc tactcgacca acatcactcc cgaccgggag  240
accggcatcg gccgctacag cttcgaagag ttcgaccgcg ccatgcgcaa gggggtgacc  300
gccgagggag tgaatctcta tccggcgatg ccctacccgt cctacgccaa gatcagcgaa  360
gaagacatgc gtgcactgta cgcctacctg atgcacggcg tgcaacccgt cacccaggcg  420
aatacgccga gcgcgatgag ctggccgttc aaccagcgct ggggcctgtc gctgtggaac  480
tgggcgttcc tcgacgacgc gccgttcacc ccctccagcg acgcggaccc ggtgatcaac  540
cgcggcgcct acctggtaca ggggctcggc cactgcgggc cctgccatac tccgcgcggc  600
atcgccttcc aggaaaaagc catgagcgaa gccggtcgtt ccgggcagtt ctacctcgcc  660
ggagaaaccg tcgaacaatg gcaagccctg agcctgcgca acctgtggac ggtggaggac  720
accgtgcagt tgctgaagac cgggcagaac cgcttcgcca cggtgtccgg cagcatgacc  780
gatgtcatcc accacagcac ccagcacttc agcgacgacg atctgctggc catcgccagc  840
tacctgaagt ccctgccggc cggcaaggac gacctgccca tgcccgacag cgaacgccca  900
ctggcagcac cggtcgacct gtacagctcg cggggcggtc tcggctacgc gcagttctgc  960
tccgactgcc accgcaagga cggcagcggc gtcccaggca tgttcccgcc gctggccggc  1020
aaccccacgg tcgcttcggc caacccgagc acgctactgc atatcaccct taccggcggc  1080
aaaaccgcgc agaccgcaac ccactcgcgg gtctacacca tgcccggctt cgcccagctg  1140
gaagaccgcg aaatcgccga gatcctcagc ttcgtccgca gcagttgggg caaccagggg  1200
tcgtcgatcg atgccggcca ggtgaagaaa ctgcgccagc ggatcgaggc cggcaacggc  1260
ccggccacga ccttcgtctc tccacgcctg gcggacatgc tcggcgcgcc gaacgccgaa  1320
caggtggtac gcggcatgcg cctgcacctg gagaccgcg agctgctgcc ggcgaacgtc  1380
ggcaaccagt tgcactgcac cagttgccac ctgaacgccg gaaccgtagc cgacggctcg  1440
cccttcgtcg gcgtctcggc gttcttcccc agctacgcgc cccgggcggg caaggtcatc  1500
ggcctggagg aacgcatcaa cggctgcttc cggcgtcga tgaacggtaa gcctctgccg  1560
ccggactctg ccgacatgca ggcgatggtg gcctacttcg actggatgaa gaacaacacc  1620
cggccgcagg acaaggtcgc cggccgcggc gtcggcaagg tcgacccggc gctgaagccc  1680
gacccggaga acggccgcaa ggtctacgcc cgacaatgcg tggtgtgtca tggcgagaat  1740
ggcgagggc tgaggaacag tgccggcgag atgctcttcc caccgctgtg gggcgacgag  1800
tcgttcaata tcggcgcccgg catggcgcgg accttcaccg ctgccgcctt cgtcaagcac  1860
aacatgccga tcggcttcca ggaacgcttc ccgctcaccg agggcggcct cagcgaccag  1920
gacgcagtgg acgtcgcgga gtattttcg caccagccgc gcccggactt cccggacaag  1980
atcaaggact ggccgaagga caagcgtccg ctggatgccc gctactga  2028

SEQ ID NO: 24         moltype = DNA  length = 2049
FEATURE               Location/Qualifiers
source                1..2049
                      mol_type = genomic DNA
                      organism = Pseudomonas aeruginosa
SEQUENCE: 24
atgcccggta aagccttgcg tgtcatgttg tgtgcctggt cgtgcctgtt ggccgggcag  60
gcgagcgccc tgggagtggg agacatcatc ctgcattcgg cgctcaacca gccgctggat  120
gcggatatcg aactgctcga cgtcggcgat ctcggcgcgg acgagatcga ggtccgcctg  180
gcgggcgccg acgtcttcgc cgcggccggg gtggaacgct tgcagttcct caacgagctg  240
cgtttcagtc cggtgctcca ggggcgcggt ggcaatcgca tccatgtgtc ctcgatccga  300
ccggtgcagg agcctacct gaatttcctg gtggaggtgg cccgccccaa cggccgcatc  360
gtccgcgaat tcaccgtact gctcgatccg ctcggttata cgccgcgcat gcttccggcc  420
gcgcgcagcg ggatcgagcc gcagcggcaa tcctcgacgc cggtgcctgc gccgcgtagt  480
gccgcggtcg tcgtagaccc ggcactgctg gagccgggcg acgaataacct ggctcgcccc  540
agcgacaacc tctgggccat cagcggacgc ctgcgtggtg ccggcaacgc cgatcgcgcg  600
caactcatgg aggctctgta ccagctcaat ccgcaggcct tcgtcaatgc cgaccggcac  660
cggctcaagg ccggcgcgcg cctgcgcctg cggccggct accagccgga gcgaggcgcg  720
cccggcgccg tgaaggaggc ggccgtggaa gtcctgccgc cagccgatgc cgccgtggtg  780
gaaaacgctc cggcggctct cgtcgaggcg cagcgccagg cggatgccga ggccgaggcg  840
ttggcccggc aacgggagga actgagccag cggatggacg atctgcaacg ccagttgcag  900
gccttgcagg aacaactgca gcagcgcgat caccaggtcg ccgaactgca acagcaactg  960
gccccggcgcc aggcggtgcg gcccgcggcg ccgccgcctg ccgcggccgc gccttcggtt  1020
gcgcaaccgc ttgaaacgcc gacggactcg cagtactggc gctggatgat cgtcctgctg  1080
ctggtcctcg ctctgctcgg cgtgttgctg ttgcgtcgcc gccgcgaaga ggctcctgtc  1140
ccggcggtcg aaccgaagcg ccgggtcgcc ctgaacctgc tcgtcggccg tggccgcgac  1200
ccccggccg ccgcaccggc gccggcaaag gtcgaagaac aggccaggcc gccggtcgcc  1260
gctccctcca gcccgcgcc gtctcctccg cctgctccgg ccgccgctcc gcgcgccgc  1320
atggctgcgc cggacaagct ggacggcgcc gacatctata tcgcctacgg tcgctacgga  1380
caggcccgcg acctgctgcg tcaggtactc gccgagcagc cgcagcgcct gagcgcgcgg  1440
atgaagctgt tgctggtgct ggctgagctg ggcgatgcgg gcgcgcttga ggcgcttga  1500
gaggaaaccc tggccagtgg cggcaacccg gaggccatcg acgagttgcg cggacgctac  1560
ccggcgctgc tacagatgcc ggcgaccgag acgccggcgg caacaaccaa ggacgacgac  1620
tggagcgacc tgccgctggc cgagtcgccc gttttgcagc aaccggatgc gacctcgggc  1680
gccgacggct cgcgcgacct caacctcgat ctcgatctcg actggggcgc cctggagaat  1740
cccctggaca accccgacct gccgcggccgc gccgctgccg gcaaggcgga accggcggag  1800
```

-continued

```
gagcccctgg cgttcgagag caatctccat gaactgccgg atgtcgccga gtacgaacac    1860
ctcgaactcg accagccaga gccggccacg gtgccgccgg aggaggcctc ggccagcctg    1920
gaccgggccc gcgcctgcat cgacagcggc gatctcgacc aggccagccg catcctgcgc    1980
ctggtggtgg cgcacggcga cccgtggcag aaggccgagg cgcgcgagtt gctggcactg    2040
atcgcctga                                                             2049

SEQ ID NO: 25          moltype = DNA  length = 2064
FEATURE                Location/Qualifiers
source                 1..2064
                       mol_type = genomic DNA
                       organism = Pseudomonas aeruginosa
SEQUENCE: 25
atgtcctctt ccggcctttt cccttcccgt ccgctctggc ctctcacgcc actggcgctg    60
gcctgcctga tcgtttcggg ggaaacgctc ggcgccgacg gccgccccag cgaattgccc    120
tcccaggtga tcaccgccaa cccgctgggc aacgaatctc ccgccacgcc cagcagcgtg    180
ctcgaaggcg acgagctgac cctgcgacag aaaggcagcc tcggcgaaac cctcaacggc    240
ctgcccgggg tgtcctccac ctacttcgga ccgggcgcca gccgaccggt gatccgcggc    300
atggacggtg atcgcatccg cctgctgcgc aacggcgtcg gtgcgctcga cgcctcgtcg    360
ctgtcctacg accacgcggt gccggaagac cccaacagcg tcgagcgcct ggaagtggta    420
cgcggccgg ccgccctgct ctacggcggc aatgccatcg gcggggtggt gaacagcttc     480
gacaaccgca tccccagcga acccgtcgac ggcatccacg gcagcggcga actgcgctac    540
ggcggcgccg acaccacccg tagccgctcc ggcgcactgg aggccggcga cggcaacttc    600
gccctgcacg tggacgccgc cagccgcgag ttcaacgacg tcaggattcc cggctacgcg    660
cattccagcc gccagcggca gatcgacggc gacaccggca agcatcgggt gcagaacagc    720
gacggccgcc aggacggcgg cgccgtcggt ggctcctatc actgggagca cggttacgcc    780
ggcctctcct acagcggcta cgacagcaac tatggctcgc ctgccggcga cgacgtgcgc    840
ctgaagatgc agcaggaccg ctacgccttc gcctccgaga tccgcgacct cgaaggcccg    900
ttcacctcgc tgaagctgga cgccgcctat accaagtacg agcacaagga aatcgaggac    960
ggcgagaccg gcaccacctt caagaacgaa ggctacgaag gccgcatcga ggcccgccac    1020
cgcccgctcg gcccgctgaa cggggtggtc ggcgcgcagt tcgccaacag ccgcttctcc    1080
gccctcggcg aggaagcctt cgtgccgcac acggaaaccg acagcgccgc gctgttcgcc    1140
ctggaggaat ggaagctcag cgaccgcctc gacctcagct tcggcgcccg cctggagcac    1200
acccgcgtgg accccgacgc caagggcaac gagcgcttcg ccgagaacga cggttcgcag    1260
agcttcacca ccggcagcct gtccaccggc gcggtgtaca agctgacgcc gatctggtcg    1320
ctggccgcca ccctcagcta caccgagcgc gccccgacct tctacgagct gtacgccaac    1380
ggtccgcacg ccgccaccgg tacctacgag gtaggcgatg ccgacgcgga caaggaaaag    1440
gcggtctcca ccgacctcgc cctgcgcttc gacaacggcg tgcacaaggg cagcgtcggg    1500
gtgttctaca gccgcttctc caactacatc ggcctgctcg ccagcggtcg ccatcgcaac    1560
gaggaaggcg aagtggtcgc cgccggcgat gacgaggcgc tgccggaata cctctacagc    1620
ggcgttcgcg cggacttcta cggcgtcgag gcgcaggacc gcatccacct gctggaaagc    1680
ccgtacggca acttcgacct ggaactctcc ggggactaca cccgcgccaa gaacaaggac    1740
accggcgaac cgctgccacg catcgccccg ctgcgcctga acaccgcgct gatctgggag    1800
ttgcagcagt ggcaggccgc ggtcgacgtc gaacacgccg cctcgcagca ccgcgtgccg    1860
gaggaagaac tctccaccga cggctacacc accctcggcg ccagcctcgg ctacaacttc    1920
gacctcggcg agagccgctg gctggccttc gtcaagggca ccaacctgac caaccagacc    1980
gtgcgctacg ccagttcgat cctgcgcgac cgggtgccgg cggcgggacg cggcatcgag    2040
gcgggggtga aggtggcgtt ctga                                           2064

SEQ ID NO: 26          moltype = DNA  length = 2412
FEATURE                Location/Qualifiers
source                 1..2412
                       mol_type = genomic DNA
                       organism = Pseudomonas aeruginosa
SEQUENCE: 26
atgaggcaat cagctttcca ccatgcccgg cgtcgttggc ctgtactggg cgtggcgctg    60
ggcgcgctac tggtcgcggc gtgtagcgag acgccgaagg tccccggcgt gcccccggcc    120
gacgaggaag tcggtcggcc gctgagcagt gtccgctccg gtgcgccgtt gcgcagcgcc    180
gacgtccgcg agcggcccca ggccgagcag gcccgccgcg cgctgagtgc cggacgcggc    240
gtggcgcgct ccggtggcgt ggctccggtc tcagcgacag cggccgaact cggcgagcag    300
ccggtcagcc tgaatttcgt cgataccgag gtggaagcgg tggtgcgcgc gctgtcgcgc    360
gccaccggcc ggcagttcct ggtcgacccg cgggtgaagg gcaagctgac cctggtttcc    420
gaaggccagg tgcggcgcg caccgcctac cgcatgctca ccagcgccct gcgcatgcag    480
ggcttcagcg tggtcgacgt cgacggggtc agccaggtgg tgccggaggc cgacgccaag    540
ctgctcggcg ggcggtcta cggcgccgac cggccggacg ccaacggcat ggtcgacccg    600
accttccgcc tgcgctacga gaacgcggtg aacctgatcc cggtactgcg cccgatcgtc    660
gcgcagaaca acccgatcaa tgccttatccg gggaacaaca ccgtggtggt caccgactac    720
gcggaaaacc tcgatcgggt cgccgggatc atcgccagca tcgacatccc cagcgccagc    780
gacaccgacg tggtgccgat ccagaacggt atcgcggtgg acatcgccag caccgtctcc    840
gaactgctcg acagccaggg cagcggcggc gccgagcagg ccagaagac cgtggtgctc    900
gccgacccac gctccaacag catcgtgatc cgctcgccga gccccgagcg cacgcaattg    960
gcgcgcgacc tgatcggcaa gctggacagc gtgcaaagca atcccggcaa cctccatgtg    1020
gtctacttgc gcaacgccca ggcgacccgc ctggcccagg ccctgcgcgg gctgatcacc    1080
ggcgacagcg cggcgagggg caacgagggc gaccagcagc gcgcgcgcct gagcggcggc    1140
ggcatgctcg gtggccgcaa cagcgtgact ggtagccagg cgcaggccaat    1200
accacgggca gcggttccag cggggttgggc ggcagcaacc gcagcggcgg cgcctatggt    1260
gcgatgggca gcgccagggc cggcgccgga cccggtgcga tggcgagga gaactcggcg    1320
ttcttccgccg gcgggtaac cgtacaggcc gacgccacca ccaacaccct gctgatttcc    1380
gcacccgagc cgttgtaccg caacctccgc gaagtcatcg acctgctcga ccagcgccgc    1440
gcccaggtgg tgatcgaaag cctgatcgtc gaggtcagcg aagacgactc cagcgagttc    1500
```

-continued

```
ggcatccagt ggcaggccgg caacctcggc ggcaacggcg tgttcggcgcg ggtcaacttc    1560
ggccagtcgg cgctgaacac ggccggcaag aacaccatcg acgtgttgcc caaggggctc    1620
aacatcggcc tggtggatgg caccgtggac atccccggga tcggcaagat cctcgacctc    1680
aaggtgctcg cccgggcgct gaagagccgc ggcggcacca acgtcctgtc gaccccgaac    1740
ctgctgaccc tggacaacga gtcggcgagc atcatgtcg gccagaccat acccttcgtc    1800
agcggccagt acgtcaccga cggcggcggt accagcaaca acccgttcca gaccatccag    1860
cgcgaggacg tcggcctgaa gctgaacatc cgtccgcaga tctccgaggg aggaacggtc    1920
aagctcgacg tctaccagga ggtcagcagc gtcgacgagc gcgccagcac cgccgccggg    1980
gtggtcacca caagcgcgc gatcgatacc agcatcctcc tcgacgacgg ccagatcatg    2040
gtcctcggcg gcctgttgca ggacaacgtg caggacaaca ccgacggcgt tcccggactc    2100
tccagcctcc ccggcgtcgg ctcgctgttc cgctaccaga agcgctcgcg gaccaagacc    2160
aacctgatgg tcttcctgcg tccctacatc gtccgcgacg ccgccgccgg ccgcagcatc    2220
accctcaacc gctacgactt catccgccgc gcccagcagc gcgtgcagcc gcgccacgac    2280
tggagcgtcg gcgacatgca ggctccggtg ctgccgccgg cgcagcaggg catcccgcag    2340
gccgcctacg acttgcgccc gagcccgcgg ccgctgcgcg cggtaccgtt gggcgaggcg    2400
gcgccgctat ga                                                       2412

SEQ ID NO: 27          moltype = DNA   length = 3489
FEATURE                Location/Qualifiers
source                 1..3489
                       mol_type = genomic DNA
                       organism = Pseudomonas aeruginosa
SEQUENCE: 27
atgcgcctga agagcatcaa gctggcgggg ttcaagtcct tcgtcgatcc gaccacggtg    60
aacttcccca gcaacatggc ggcagtggta gggccgaacg gctgcggcaa gtcgaacatc    120
atcgacgcgg tgcgctgggt gatggacgaa agctcggcga agaacctgcg cggcgagtcg    180
atgaccgatg tcatcttcaa cggctcgaat acccgcaagc cggtgagcga ggcgagcatc    240
gagctgatct tcgacaacgc cgagaccacc ctggtgggcg aatacgccca gtacgccgag    300
atatccattc gccggcggg ctcgcgggat gggcagaaca cctatttcct caacggcacc    360
aagtgccggc ggcgcgacat caccgacatc ttcctcggca ccggcctggg gccgcgcgag    420
tactcgatca tcgaacaggg catgatctcc aagctgatcg aggcgcgtcc ggaagacctg    480
cgcaacttca tcgaggaagc cgcgggcatt tccaagtaca aggagcgccg ccgcgaaacc    540
gaaagccgca tccgtcggac ccaggaaaac ctggcacgcc tcaccgacct gcgcgaagag    600
ctggggcggc aactggaacg cctgcaccgg caggcccagt cggcggaaaa ataccaggaa    660
cacaaggccg aggagcgcca gctcaaggcc cagctgggtg ccgtgcgctg gcgcgacctg    720
aacgagcagg tcggtcagcg cgagcgggtc atcggcgacc aggagatcgc cttcgaggcc    780
ctggtggccg agcagcgtgg tgccgatgcc ggcatcgaac ggctgcgcga cggccatcac    840
gagttgtccg aacgcttcaa ccaggtgcag gcacgcttct attcggtcgg cggcgacatc    900
gcccgggtcg agcagagcat ccagcatggc cagcagcgcc agcgccagtt gcaggacgac    960
ttgcgcgaag ccgaacggac ccgccaggaa accgaatcgc acctcgggca tgaccgtacc    1020
ttgctcgcga ccctggccga ggaaatggcc atgctcgcac cggaacagga actcagcgcg    1080
gccgccgcg aagaagcggg catcgccctg gaacaggccg agcagggcat gcaggcctgg    1140
cagcagcagt gggatgcctt caaccagcag agcgccgaac cccgccgcca ggcgcgaggtg    1200
cagcagtcgc gcatccagca cctggagcag agcctggagc gcctgcagga tcgcgagcgg    1260
cgcctgcagg aggagcgtgg ccagttggcg gccgaccccg aggacgcggc gatcctcgaa    1320
ctcaacgaac aggtggcgat cgccgaactg gccctgaag aactgcaatt gcaggagcag    1380
ggccaagccg agcgactcga acaattgcgc caggaattgc agcagctggc cgccgaacag    1440
caccaggcgc agggcgagtt gcagcgcctg aacgggcgca tcgcttcgct ggaggccctg    1500
cagcaggccg ctctcgatcc cggacagggc gccttggagt ggttgcgcga gcagggcctg    1560
gaacaacgtc cgcgcctcgc cgaaggcttg cgtgtcgagc cgggttggga gctggcggtg    1620
gagaccgtgc tcggcgcgga tctgcaggcg tcttgctgg acggcttcga cgggctcgcc    1680
ctggccggct tcggcaaggg cgagctgcgc ctgctcagcc ccgctcgcgg agccgcgacg    1740
gcggccggtt cgctgctgga caaggtccgc gccgacgccg acctgagtcc ctggttggcc    1800
cgggtgaaac cggtggagac cctggaacag gcgctcgccc agcgcggcgc cctggacgac    1860
ggcgagagcc tgatcagtcg cgatggctac tgggtcggcg ggcacttcct gcgggtccgg    1920
cgcagcgacg aggcccaggg cggcatgctc gcccgcgccc aggaactgga ggcgttgcag    1980
gagcggcggg aggccctgga aaccgtgtc gccgaaggcg aggagcgtct ggctgcggcc    2040
cgcgacgagc agcgcgagct ggaaggcgcg cgggagcagg tgcggcgcca ggtccaggag    2100
gaggggcgcc ggcacggcga gctgaaggcg cagttgtccg cgcacgcagc caaggtcgag    2160
caactggtac tgcgtcgccg ccgtctcgac gaagaagtgg cggaactggc cgagcagcgc    2220
gcgctggaac aggagcaact gagcgaggcg cgcctgaccc tgcaggaagc gctggatagc    2280
atggcgctgg acaccgagcg ccgggaatcc ctgctggcgg agcgtgacgc cctgcgcgaa    2340
cggctcgacc ggattcgcca ggatgcccgc acccacaagg accatgcgca ccagttggcg    2400
gtgcgggtcg gctcgctgaa ggcgcagcac aattccaccc acgaggccct ggacgacatc    2460
gaccagcagt cggcgcgcct caacgagcgt tgcgaacagc tcaacctcaa tctgtgaggag    2520
ggggcggcac cgctggaaga gctgcgcatg aagctcgagg agttgctgga gcggcggatg    2580
gccgtcgagg acgaactcaa gcaggcgcgg ctggccctgg aagacgccga tcgcgaactg    2640
cgcgaggtgg agaagcgccg cggccaggcc gagcagcaat cgcaactgct gcgtggccag    2700
ctggagcagc agcgcctgga gtggcagggg ctggtggtcg gtgcgcaaagc cttgcaggag    2760
cagctcgccg aagacggcta cgacctgcat acggtactgg ccaacctgcc cctggatgcc    2820
agcgaacgcg attgggagga gcgtctcgag agtctcgcgg cgcgcatcca gcgtctgggg    2880
ccgatcaacc tggcggcgat cgaggagtac cagcagcagt ccgagcgcaa gcgctacctg    2940
gactcgcaga acgacgacct ggccgaagcg ctggagacgc tggaaaacgt catccgcaag    3000
atcgaccggg aaacccgcaa tcgtttcaag gaaaccttcg accagatcaa tgctggccctt    3060
caggcattgt tcccgaaggt attcggcggc ggtacggcat atctggaact taccggcgaa    3120
gatctactcg ataccggtgt ggcgatcatg gcgcgcccgc cggcaagaa gaacagcacc    3180
atccacttgt tgtccggcgg ggaaaaggcg ctgaccgcgc tggcgctggt attcgccatc    3240
ttccagttga acccggcgcc gttctgcatg ctcgacgaag tcgatgcgcc attggacgat    3300
gccaacgtcg gacgttatgc gcgattggtg aaggagatgt cggaaaaggt gcagttcatc    3360
```

```
tatatcacccc acaacaagat cgccatggaa atggccgatc agttgatggg cgtgaccatg   3420
catgagccgg gctgttcacg gcttgttgca gttgacgtgg aagaggcggt cgcattggct   3480
gaagcctga                                                          3489

SEQ ID NO: 28           moltype = DNA   length = 4254
FEATURE                 Location/Qualifiers
source                  1..4254
                        mol_type = genomic DNA
                        organism = Pseudomonas aeruginosa
SEQUENCE: 28
atgaacaaga gctatacgct ggtctggaac caggccacag gctgttggaa cgtcgcaagc   60
gaaggtaccc gtcggcgcag caagagcgga cgcggcaagg cgctcgtagt cgccggagcg   120
tcactgctcg gcctgttctg ccaggccccc gccttcgccc tgcccagcgg cgccacggtc   180
gtttcaggcg atgccggatt ccagacatcc accgatggcc ggcatatggt catcgaccag   240
cagagccaca agctgatcac caattggaac gagttcagcg tccgtgccga tgagcgggtc   300
agcttccacc agccgggcca ggacgccgtc gccctgaacc gggtgatcgg ccgcaacggc   360
agcgatatcc aggggcggat agatgccaac ggcaaggtct tcctggtcaa tcccaacggc   420
gtggtcttcg gcaagtccgc ccaggtcaac gtaggcggct tggtggcttc caccctggac   480
ctggccgaca gggacttcct cgccggcaac taccagttct ccggcgactc cggcgcaacc   540
gtaagcaatg ccggcagcct gcaagccagc gaaggcggca gcatcgccct gctgggcgcc   600
cgggtcagca acgacggctt gatccaggcg caactcggcg acgtggccct gggcgcaggc   660
cagggcatca acctcaattt cgacggcgac ggcctgctca acctgcaggt ggacaagggc   720
tcggtcgacg ctctcgcaca caacggcggc ctcatccgcg ccgatggcgg ccaggtgctg   780
atgagcgccc gcagcgccga cagcctgctc aagaccgtcg tcaacaacca gggcactctc   840
gaggccagga cgctacgcag cgcggaagga cgcatcgtcc tcgacggcgg cgaacagggt   900
accgtcgggg tggccggcaa gcaggacgcc agcgccatcg gcggaggcaa tggcggcctg   960
gtgctgaacc agggcgcgaa cgtcgagata cagcgaaccg cgcaggtgga cacccatgcc   1020
gaccagggcg caaccggcac ctggaggatt ctctcgcacg aggtcagcgt agccgctgtc   1080
ggccaggcaa acgctgccgg tgatggttcc ggccaggtcc atgtagcgca gggcccagcc   1140
ggggccaatg cgtccgatag caacggcgtg accatcgttc agcagcagcc ggccgtcgac   1200
ctcgccgccg gcgccaacgg tacctccgca gtgcagagcc agagcggcgc caacatcggc   1260
tcgggcgcca atggcatcag cgtcgtgcaa agccagaaca gccccaatat cggctcgggc   1320
gccaatggca tcagcgtcgt gcaaagccag aatggcgcca atatcggcgc cggcgcgagt   1380
ggcatcagcg tcgtgcagag ccagaacagc cccaacatcg gctcgggcgt caatggcgtg   1440
actgtcgtgc agagccagaa cggtgccaat atcggttcgg gcgcaagtgg catcaccgtt   1500
gtgcaaagcc agaatggcgc aaatatcggt tcaggcgcga gtggcatcag cgtcgtgcag   1560
agccagagcg gccccagcat cggctcgggc gtcaatggcg tcacaatcgt gcagagccag   1620
agcggtgcca acatcggccc cggcgtcagc ggaatcgatg tcgtccagac ccagactctc   1680
cccaacctga gcccaggcgc caatggctcc agcatcgtcc aggtccagac gctacccgat   1740
atcgccgccg acgccggcaa tgtgcatgtc gtgcaggtcc agaccggcgg taacaaggtc   1800
ttcggcaact ccgccaccaa cgtcaggtca cgtaccgttc aggcccggag caacgagaat   1860
gtcggttccg gcctggcgaa tccaagcagc gcgggaaaag gctcgacgtt gcatgccgat   1920
accctcgccc gcaacctttc cacaagcaac gtcgaagtgg tcgccacccg gggcaacgcg   1980
catgtcggcg cgccgctgtc ctgggacagc ggcaacggcc tgacgctaac cgccgagcgc   2040
ggggacctca ggatcaatgg cgcgctgacg gcccagggg aaaacgccag ccttactctc   2100
aatgccgggc agcgccctct ccgtatcgac gacagcctct ctctcactgg ccagggagcc   2160
cgggtcgaat tcaattcgga caagggttat gccctgcccg aaggcacccg gatcaccctg   2220
tccggcaaga acgcaggatt ccgcgccaat gggcgggact acagcgtgat ccaggacctg   2280
cagcagttgc gcggcatcga tagggacctg ggcggcagct atgtcctcgg caatcgaatc   2340
gcaggcggca actccagctt cctgtcgata ggcaacgcga gcgccttcgg cggtaccttc   2400
gacggcctgg gcaacaccat cgataatctc gccgtctacg gcaccggcgc ctactccgat   2460
ctgttcagcg tcaaccgggg caccctccgc aacctgaacc tggaacgcat ttccgccgat   2520
ggagcacagg ccacccacta caatgtccag gtcggtagcc tggccgccgt caacctcggt   2580
cgcatcgaca atgtgaacgc cagcgacatc cgtatcgccg cggcctcgaa gctgaacagc   2640
ctcggcgggc tggtcgcact gaacctgggt agtatcgaca acgccagcgc cagcggcacg   2700
ctggtcggca accgccacac ctatgctctg ggcggactcg cagccgaaaa catcagcaca   2760
gccaggggcg tggccagcat ctccaacagc cgggccgatt ttgccatctc cggccagttg   2820
aaggaccatg ccagccacta cggcgcgggg ggcctggtag gcaggaaccg cggcggcctc   2880
atccgcagca gcggcagtca gggaacgctg tcgctgagcg gtcacggaat gaacctggga   2940
ggactggtcg gatacagttc cgccggcgga ctggcggacg tttccgcctc cgtcgacgtc   3000
tcaggcaacg gacagcgcgg cctgtacggt gggctcatcg gcctcaacgt aaacagtggt   3060
attgcccacg ccacggccag cggcaaggtc cggggcacag acgcggaagc actgggcggg   3120
ctgatcggcc ggaacctgaa cgcggccatc aacaacgcca gcgccatgg cgatgtcagc   3180
ctgcaagccg gtcgctacct gggaggcctg atcggccaca accggccacg caacctgagc   3240
aacgtcagta ccagcggcaa cctgagtggt gggtcgctgc tccaggccgg cggcctgatc   3300
ggtctcaacg ccaatgcctc gctggtcaat gcctccgcca agggcaatgt cgctacccgc   3360
ggagcagaag cggttggcgg tctgctcgga gaaaacctgt acggctccgt catcaacggt   3420
tccgccagtg gcgaagtcac cgacggcagc ggcaaaaccc tgggtggcct gatagggtcc   3480
aacctcggcg gcaatcattc caacctgaag gcctccgggt gggtaaacgc aggggcgaac   3540
agtgacgtgg gagggctgat cggccacaac cgggagcggca accacagcac cctggcggca   3600
tccggcaatg tcaccggggg caagggcagt cgcgtcggcg gactcgtcgg ctataacgat   3660
gccgcctcgc tgacgaacgt ctcggcttcg ggcaacgtca cgccagtggt tccagggcc   3720
atcggcgggt tgatcggcag tgacctgcga ggttcgctga tgctcgccag cagtcatgga   3780
atcgtgaacg acaagaccag ccacaacctg ggagggttcg gggctgaaaacgct  3840
tcgatccgct ccgccaaggc cagcggtgcg gtgagcggag gcgccgggat cagggccggc   3900
ggactggtcg gctccctgga gggctggcag gctctcatcc tggggctc gccggcggc   3960
gatgtgacgc cgggctacga tagctatatt ggcgggctgg tgggcttcag caccgccacc   4020
atcagcggc cttccgcttc cggcaaggtc ggaggctcgg tctgctgggg cggcctggtc   4080
gcctggaacc aggggaatgt catgggttct tcggccagcg gcaggctgga gccacaaatc   4140
```

-continued

```
cccaaccaga tccatggcgg actgatcggc atcaattttg gctggcagtc ctggaactcg   4200
gtatacgggg ctgcggcgac cgttccaatg ataggtcgcc actacaacct gtga          4254

SEQ ID NO: 29         moltype = RNA  length = 408
FEATURE               Location/Qualifiers
source                1..408
                      mol_type = transcribed RNA
                      organism = Pseudomonas aeruginosa
SEQUENCE: 29
atgccccgtg gcgacaagag caagtacagc gacaagcagc agcgcaaggc cgagcacatc     60
gaggagagct acaaggccaa gggtgtgagc gagtcggaag ccgaggcgcg cgcctgggcg    120
acggtgaaca agcagtccgg cggcggcgag cgcaagggcg gttccggccg cgccaagagc    180
gagacggcca agcgcgccga ccgcaaggac tcggcccatc gcgccgccca ggcccgctca    240
gggagaccgg ccaaccgcgg ctcggcgagc cgtggcaaac gtcaaggcag cacctcggtg    300
agcgagatga cccgcgagga attgatgcag ctggcgcgca agcgcgacat ccgcggtcgt    360
tcgacgatgc gcaaggccga actgatcgag gccctgtccc gggcctga               408

SEQ ID NO: 30         moltype = RNA  length = 417
FEATURE               Location/Qualifiers
source                1..417
                      mol_type = transcribed RNA
                      organism = Pseudomonas aeruginosa
SEQUENCE: 30
atgaatatcc tgcgtatccc gatgttcgta ttggccatgg ccgtctcggc ccatggtttc     60
gctgccaccg cgcagcagga gaagatgacc gcctgcaacg ccgaggccac caccaaggcg    120
ctcaagggcg acgaacgcaa ggcgttcatg agcggctgcc tgaaggccgg cgcgcctgcg    180
ggcggcaagg ccaccgccca gcaggagaag atgaagagct gcaacgccga cgccagtgcc    240
aagtcgctca agggcgacga acgcaaggcg ttcatgagca gttgcctgaa ggccggcggc    300
agcgccaagg cggcgaccca gcaggagaag atgaagacct gcaacgccga cgccaccgcc    360
aaggcgctca agggcgacga acgcaaggcg ttcatgagca cctgcctgaa gaagtga      417

SEQ ID NO: 31         moltype = RNA  length = 426
FEATURE               Location/Qualifiers
source                1..426
                      mol_type = transcribed RNA
                      organism = Pseudomonas aeruginosa
SEQUENCE: 31
atggctacac gacggaaaac aacaccccag gaaatcgatg atatccagga ccgcatgggt     60
tcgatgcgcg agctcgattt cgacgagcgc cgccaggcgc gtaaggcgcg gatcggcgac    120
gagcggcccg aggccgaggt ggaggccgaa ttttcctcgc ggcgggtacg cgaggcgggc    180
cacgctggcg ggcagccgga cgaggacgat ggttaccagg ataacgtcgg catggacgat    240
ctggcgccg aaaccctgat cgacgaaagc ggcgcccgct cgccggccga gcgcggcggc    300
gaatcgccg cggacaagcg cctgagggtc gtgcatggca acgagatcgg agccggccac    360
ggcctcgacg aggccgagct ggcgcgtcgt gatccgctcg acgttcctc cgacgaggaa    420
cgctga                                                             426

SEQ ID NO: 32         moltype = RNA  length = 453
FEATURE               Location/Qualifiers
source                1..453
                      mol_type = transcribed RNA
                      organism = Pseudomonas aeruginosa
SEQUENCE: 32
atgcgacgca tgatcctccc ggccagcttg ttgctcgccc tctcctcttt cgccatggcc     60
gccccgatct acaaatgggt cgacgccgag ggcgtcaccc acttcggcgc acaaccgccg    120
caaggtgcgc aagcgaccac ggtgaatacc cagaccgccc cgccgccgga caacttcccc    180
ctgcccccct cgacccccgg c accgaccatc cagcagaaac cggccgatcc cgagcagaag    240
gcgatcgacg acaaggtgaa gcagcaagtg cgcaaggaag aggccgagcg caagcagttc    300
tgcgaagaga cccgcaacaa cctcgcgcaa ctgaagaaca acccgcgcgt aagggtcgac    360
gaaggcaagg gcgaactccg tcgcctcggc gaggaagaac gccaggagcg aatcgccaag    420
gccgaaaagg cgatccagga gaattgccgc tga                               453

SEQ ID NO: 33         moltype = RNA  length = 714
FEATURE               Location/Qualifiers
source                1..714
                      mol_type = transcribed RNA
                      organism = Pseudomonas aeruginosa
SEQUENCE: 33
atgttcacct cccgttgcct gcctctggcc gcagccgtca ccgcactggc gctgctcgcc     60
ggttgtgcca acaacaaccc ctacgacacg caaagccaaa gccagggtgg catgagcaag    120
acggccaagt acggcggact gggtgcgctg gccggcgccg tcgccggcgc tgcgatcgac    180
cacaacaacc gtggcaaggg cgcgctgatc ggcgctgccg ttgccggcgc ggccgccgcg    240
ggttatggct actacgccga caagcaggaa gccgagctgc gtcggcagat ggaaggcacc    300
ggcgtggaag tgcagcgcca aggtgacgac atcaagctga tcatgccggg caacatcacc    360
ttcgccaccg attcggcgaa catcgccccg agcttctacg cgccgctgaa caacctggcg    420
aactcgttca gcagtacaa ccagaacacc atcgagattg tcggttacac cgacagcacc    480
ggcagccgcc agcacaacat ggacctgtcc cagcgtcgtg cgcagagcgt ggccggctac    540
ctgaccgccc agggcgtcga cggcacccgc ctgagcaccc gcggcatggg cccggaccag    600
ccgatcgcga gcaactccac tgccgacggt cgcgcgcaga accggcgcgt cgaggtcaac    660
ctgcgaccgg ttccgggcgc ccaggggcccg gcgcagaccc agccgcagta ctga        714
```

-continued

```
SEQ ID NO: 34            moltype = RNA   length = 1191
FEATURE                  Location/Qualifiers
source                   1..1191
                         mol_type = transcribed RNA
                         organism = Pseudomonas aeruginosa
SEQUENCE: 34
atgaagcgac tggctggact gaccgccctc gccctggtta tcggcaacac ttccggctgc   60
ggctggctgt gggggccgga gggctatttc cgcgaccgcg gtgacgacta cctcggcgcc   120
cgcgaaacgc ctcccatgca attgcccgaa ggggtgcaca gcaagccgct cgatccgctg   180
ctgccgattc cgctgaacgt cgccaccacc cacgaaaaag agggtgagta cgaggttccg   240
cgtccgcagc cgctggccaa cgccggcgac atcagcgact acagcctgca gcgcagcggt   300
gatagccgct gggtcgtggc ccagcgtccg ccggcgaaag tctggccggt ggcccggcag   360
ttcttcgagg agaacggttt ccgcatcgcc gacgagcgcg cgagttcagt   420
tccgactggc aatcgctgtc gcagctttcc gcgccgctgg cacgccgcct tagcagccgc   480
gtgagcggtg tcgagccgga cggccaggca cgggttcggg tgcgtatcga gcccggcgtg   540
caaagcaata ccagcgaggt ctacgtgctc agccagaccc gcgccgccgg tgacaccagc   600
agcccgagct ggccgagcaa gtcggtggcg ccgagcctcg acgcggcgct gctcgacgag   660
atggtcgcga gcatggcgcg cagcgccgag cagggcggct cggtctccct gctggcagcc   720
aactcgatct acgacacgcc cggcaccttc gagttgagca aggacggcag cggcaacccg   780
gtgctgacct tgcagtccga cttcgaccgc tcctgggtca gcgtcgggcg tgccctggat   840
aacgccgata tccgcgtcga cgacctcaac cgcagccttg ggtgtacta cgtgaacatc   900
gccgaagggg cgaagaagcc cgacgaagac aagcccgggt tcttcagtcg cctgttcggc   960
ggcggcgaga agaccaagga agaggaagac gccaaggcgc agcgctacca ggtccgcctg   1020
accaccgtca gcgacgccgt gcaggtcacc gtcgacaagg acatcaacac ctctgcgccg   1080
gccgatgtcg cgcaaaacgt actggaaaaa ctccaggaga gcatgcgcaa tgcggttcgc   1140
ggttctgggc agcggaagcc ggggcaattc ggccttggtg agcagttctg a              1191

SEQ ID NO: 35            moltype = RNA   length = 1632
FEATURE                  Location/Qualifiers
source                   1..1632
                         mol_type = transcribed RNA
                         organism = Pseudomonas aeruginosa
SEQUENCE: 35
atgatccgcc tgttctgcag cctgcttctc gcgctcctct gcgtctccgc ccacgccagc   60
ttcagcgcca gcgtcgaccg cgcccgcctg accgaagggg aaagcgtcga actgacgctg   120
gaatcggacg acccgaccct cttcggcaag cccgacctga gcccgctgga cgccctcttc   180
gaggtcctcg gcacgcgcca ggtcaaccgt ctcgccacac agaacggccg ggcccaggcc   240
accaccgct ggatcgtcac cctcctgccg aagcagagcg gctacgtggc gatcccgccg   300
atcagcctcg gcgccagcag cacccagccg atcaggctgc acgtactgga ggcgcgcgac   360
cgcgccaaga gcagcaagct ggcgccggtc ttcatcgatg ccagcgtcga ccaggagacg   420
gtctacgtgc aggcccaggc gatcctcacc ctgcgcatct accactcggt gtcgctatac   480
gacgacagca gcctgacccc gctggcgatg aacgacgcga aggtcgaaca gctcggcgag   540
gcgcgcacct acgagaagga gatcaacggc atccgccacg gcgtgatcga ggtgcgctac   600
gcgatcttcc gcagaagag cggcaccctg gagattcctg cgcaagcctt cagcgcgacc   660
ctggtcgacc gtgtgcagtga cgactacaac cccttcggcc cgcgccccgg ccggcagatg   720
cgggtgactt cgccgagcat cccgctgcag gtccggccca agctgccga ctatccggcc   780
gacgcgccct ggatgccggc ccgcgcgctg agcatcagcg aaagctggag cccgcagccg   840
gagcaggcgc aggtcggcga atcgctgacg cgcaatgtgc tgctgaaggt cgaggggctt   900
tccggcaccc agcttccgcc gttgccgctg cccgacgtgc aaggcctgcg cgcgctacccg   960
gaccaaccgc agttggccga ccagaacacc gaccagggcc tcatcggcag tcgcgaggaa   1020
cgcgaggcgc tggtgcccga gcaggccggg cgcatcgagt tgccggcgct cgaagtggtc   1080
tggtggaaca cccgcgaaga ccgcctggag cgcaccagcc tgccaccgcg caccctggaa   1140
gtggccgccg cgccgcaggc cgaggcggag ccgccggcgg cggcgctgcc gctcggcgaa   1200
cgcctggagc cgacgctctg gccctggcaa ctggctaccg ccgtgctggc cctgaccacc   1260
ctgctcggct tcggcctctgt gtggcgcgcc cgccagctgc cggcggtgat ccgcgccgcg   1320
gccaacggcc cgagcagccg cagcctgctc gacgagctgc gccgcgcctg cctggccaac   1380
gatccccagg cgaccgccca ggccctggac gcctgggccc gtcagcaacc cgataccctg   1440
gccgacatgg cggcccgctt cgtaccgctg tccgacgccc tggatggcct caacggcgcg   1500
ctgtacagcg agagcggcca ttcctggcag ggcgaggacc tgtggcgggc gatccgctcg   1560
ctgcccacca cggaacaagc gccggcggga gcggtcgaca atggcggcct gccaccgctc   1620
tatccgcgct ga                                                         1632

SEQ ID NO: 36            moltype = RNA   length = 1920
FEATURE                  Location/Qualifiers
source                   1..1920
                         mol_type = transcribed RNA
                         organism = Pseudomonas aeruginosa
SEQUENCE: 36
atgtcctttt cttccctcgg actctccgag gcgcttgccc gcgctgtgga ggctgcgggc   60
tacagccagc ccactcccgt gcaacagcgg gcgattcccg ccgtgttgca aggtcgcgac   120
ctgatggttc cggcacagac cggcaccggc aagaccggtg gtttcgccct gccggtactg   180
gagcgcctgt tccccgccgg tcatcccgac cgcgaacacc gccacggccc cgcgccaggcg   240
cgcgtgctgg tactgacccc gacccgtgag ctggccgacg aggtgcatga cagcttcaag   300
gtctacgccc gcgacctgcc gctgaacagc acctgcatct tcggtgggt tggcatgaac   360
ccgcagatcc aggccctggc caagggcgtg gacgtactcg tcgcctgccc cggccgcctg   420
ctcgacctgg ccgggcagaa caaggtcgac ctgtcccacg tggaaatcct cgtcctcgac   480
gaagccgacc gcatgctcga catgggcttc atccacgatg tgaagaaggt tctcgccaag   540
ctgccgccca agcgccagaa cctgctgttc tcggcaacct tctcgaaaga catcgtcgac   600
```

```
ctcgccaaca agctcctgca caacccggaa cgcatcgagg taacgccgcc gaacaccacg   660
gtcgagcgca tcgagcaacg cgtgttccgc ctgccggctc cgcagaagcg cgccctgctg   720
gcgcacctgg taaccgtcgg cgcctgggaa caggtgctgg tcttcacccg taccaagcac   780
ggcgccaacc gtctcgccga gtacctgacc aagcacggcc tgccggccgc cgcgatccat   840
ggcaacaaga gccagaacgc gcggaccaag gcgctgaccg acttcaaggc caacgacgtg   900
cgcatcctgg tggcgaccga catcgccgcc cgcggcctgg atatcgacca gttgcccat    960
gtggtcaact acgagctgcc caacgtcgag gaagactatg tccaccgcat cggccgtacc  1020
ggccgagccg gacgcagcgg cgaggcgatc tcgctggtgg cgccggacga agagaagctg  1080
ctcaaggcca tcgagaagat gaccagacag cgtattcccg atggcgatgc ccagggtttc  1140
gaccccgagg ccgtgctgcc cgaggtggcc cagccggagc cccgcgaagc gccgcagaag  1200
cagccgcgcc gcgacaagga acggcgcagc agccgcgagc gcaagccgaa agacgcccag  1260
gcgagcaacc ccgacagcaa tgtcgctgcg gcccaggacg gtaccgagaa gccggctgga  1320
aagcgccgcc gtcgcggtgg caagaacaag gaaaaccgcg aggccggcca agcgcagcag  1380
ccgcggcaga gccgcgaagc gcgtccggcc aagcccaatc ggccgccgga agtcgacggt  1440
aatcgcgatc cggaagagtt cctcgacgac gacttcgaca atttcggcaa ccgcgccgac  1500
tacgcgtcagc cctaccaggg ccaggaaaac aagggacgcg gacgccgcgg tggccagcag  1560
aaaccccagg gcggcaccgg ccagcagggt cgtggccaag gccagggcca agctcgcggc  1620
aagagccagg gcgccgctca aggcggcgct cgcggtcagg gtgccggcca gggcaaggcg  1680
aagaaaccgc gcgccggcaa gccgcgcggc cagggtcgcg agaatgcctc gcggatgagc  1740
gacgcgccgc tgcgcgagcc gtccgagtat ggcaccggca agcagccgag ccgccagccg  1800
gtggtgatca acaagcgcga cctggtgcgc atggatcgct tccccaccgc cgagcagctc  1860
gacgagctgg aaccgcggcg caagggcgag cgccccgcac tgctgacccg caaccgctaa  1920
```

SEQ ID NO: 37              moltype = RNA   length = 2028
FEATURE                    Location/Qualifiers
source                     1..2028
                           mol_type = transcribed RNA
                           organism = Pseudomonas aeruginosa

SEQUENCE: 37

```
atgcctgctt ctttcccgcg cctcggcttg ctcggcgcac tgtgctccat cgttcccctg    60
ctccatgcca gcgaaccgac cacggacgct gcgctcatcg aaaaaggccg ctacgtggcc   120
cagctcggcg actgcatcgc ctgccatacc ggcccgcagg gcgcgccgat ggccggcggc   180
ctggagctga agacgccaat gggtaccatc tactcgacca acatcactcc cgaccgggag   240
accggcatcg gccgctacag cttcgaagag ttcgaccgcg ccatgcgcaa gggggtgacc   300
gccgaggggac tgaatctcta tccggcgatg ccctacccgt cctacgccaa gatcagcgaa   360
gaagacatgc gtgcactgta cgcctacctg atgcacggcg tgcaacccgt cacccaggcg   420
aatacgccga gcgcgatgag ctggccgttc aaccagcgct ggggcctgtc gctgtggaac   480
tgggcgttcc tcgacgacgc gccgttcacc ccctccagcg acgcggaccc ggtgatcaac   540
cgcggcgcct acctggtaca ggggctcggc cactgcgggc cctgccatac tccgcgacgt   600
atcgccttcc aggaaaaagc catgagcgaa gccggtcgtt ccgggcagtt ctacctcgcg   660
ggagaaaccg tcgaacaatg gcaagccctg agcctgcgca acctgtggac ggtggaggac   720
accgtgcagt tgctgaagac cggcgagaac cgcttcgcca cggtgtccgg cagcatgacc   780
gatgtcatcc accacagcac ccagcacttc agcgacgagc atctgctggc catcgccagc   840
tacctgaagt ccctgccggc cggcaaggac gacctgccca tgcccgacag cgaacgccca   900
ctggcagcac cggtcgacct gtacagctcg cggggcggtc tcggctacgc gcagttctgc   960
tccgactgcc accgcaagga cggcagcggc gtcccaggca tgttcccgcc gctggccggc  1020
aaccccacgg tcgcttcggc caacccgagc acgctactgc atatcaccct taccggctgg  1080
aaaaccgcgc agaccgcaac ccactcgcgg gtctacacca tgcccggctt cgcccagctg  1140
gaagaccgcg aaatcgccga gatcctcagc ttcgtccgca gcagttgggg caaccagggg  1200
tcgtcgatcg atgccggcca ggtgaagaaa ctgcgccagc ggatcgaggc cggcaacggc  1260
ccggccacga ccttcgtctc tccacgcctg gcggacatgc tcgcggccgc gaacgccgaa  1320
caggtggtac gcggcatgcg cctgcacctg gagaccgcg agctgctgcc ggcgaacgtc  1380
ggcaaccagt tgcactgcac cagttgccac ctgaacgccg gaaccgtagc cgacggctcg  1440
cccttcgtcg cgctctcggc gttcttcccc agctacgcgc cccgggcggg caaggtcatc  1500
ggcctgaagg aacgcatcaa cggctgcttc cggcgctcga tgaacggtaa gcctctgccg  1560
ccggactctg ccgacatgca ggcgatggtg gcctacttcg actggatgaa gaacaacacc  1620
cggccgcagg acaaggtcgc cggccgcggc gtcggcaagg tcgacccggc gctgaagccc  1680
gacccggaga acggccgcaa ggtctacgcc cgacaatgcg tggtgtgtca tggcgagaat  1740
ggcgaggggc tgaggaacag tgccggcgag atgctcttcc caccgctgtg gggcgacgag  1800
tcgttcaata tcggcgccgg catggcgcgg accttcaccg ctgccgcctt cgtcaagcac  1860
aacatgccga tcggcttcca ggaacgcttc ccgctcggcc agggcggcct cagcgaccag  1920
gacgcagtgg acgtcgcgga gtattttttcg caccagccgc gcccggactt cccggacaag  1980
atcaaggact ggccgaagga caagcgtccg ctggatgccg ctactga                2028
```

SEQ ID NO: 38              moltype = RNA   length = 2049
FEATURE                    Location/Qualifiers
source                     1..2049
                           mol_type = transcribed RNA
                           organism = Pseudomonas aeruginosa

SEQUENCE: 38

```
atgcccggta aagccttgcg tgtcatgttg tgtgcctggt cgtgcctgtt ggccgggcag    60
gcgagcgccc tgggagtggg agacatcatc ctgcattcgg cgctcaacca gccgctggat   120
gcggatatcg aactgctcga cgtcggcgat ctcgcgcgcg acgagatcga ggtccgcctg   180
gcgggcgccg acgtcttcgc cgcggccggg gtggaacgct tgcagttcct caacgagctg   240
cgtttcagtc cggtgctcca ggggcgcggt ggcaatcgca tccatgtgtc ctcgatccga   300
ccggtgcagg agccctacct gaatttcctg tgtggaggtgg cccgccccaa cggccggcatc   360
gtccgcgaat tcaccgtact gctcgatccg ctcggttata cgccgcgcat gcttccggcc   420
gcgcgcagcg ggatcgagcc gcagcggcaa tcctcgacgc cggtgcctgc gccgcgtagt   480
gccgcggtcg tcgtagaccc ggcactgctg gagccgggcg acgaatacct ggctcgcccc   540
```

-continued

```
agcgacaacc tctgggccat cagcggacgc ctgcgtggtg ccggcaacgc cgatcgcgcg      600
caactcatgg aggctctgta ccagctcaat ccgcaggcct tcgtcaatgc cgaccggcac      660
cggctcaagg ccggcgcgcg cctgcgcctg ccggccggct accagccgga gcgaggcgcg      720
cccggcgccg tgaaggaggc ggccgtggaa gtcctgccgc cagccgatgc cgccgtggtg      780
gaaaacgctc cggcggctct cgtcgaggcg cagcgccgga cgatgccga ggccgaggcg      840
ttggcccggc aacgggagga actgagccag cggatggacg atctgcaacg ccagttgcag      900
gccttgcagg aacaactgca gcagcgcgat caccaggtcg ccgaactgca acagcaactg      960
gccccggcgcc aggcggtgcg gcccgcggcg ccgccgcctg ccgcggccgc gccttcggtt     1020
gcgcaaccgg ttgaaacgcc gacggactcg cagtactggc gctggatgat cgtcctgctg     1080
ctggtcctcg ctctgctcgg cgtgttgctg ttgcgtcgcc gccgcgaaga ggctcctgtc     1140
ccggcggtcg aaccgaagcg ccgggtcgcc ctgaacctgc cgctgcggcg tgcgccgcgc     1200
cccccggcgg ccgcaccggc gccggcaaag gtcgaagaac aggccaggcc gccggtcgcc     1260
gctccctcca gcccgcgcc gtctcctccg cctgctccgg ccgccgctcc gcgcgccgcc     1320
atggctgcg cggacaagct ggacggcgcc gacatctata tcgcctacgg tcgctacgga     1380
caggcccgcg acctgctgcg tcaggtactc gccgagcagc cgcagcgcct gagcgcgcgg     1440
atgaagctgt tgctggtgct ggctgagctg ggcgatgcgg ccggcttcga cgcgctggcc     1500
gaggaaaccc tggccagtgg cggcaacccg gaggccatcg acgagttgcg cggacgctac     1560
ccggcgctgc tacagatgcc ggcgaccgag acgccggcgg caacaaccaa ggacgacgac     1620
tggagcgacc tgccgctggc cgagtcgccc gttttgcagc aaccggatgc gacctcgggc     1680
gccgacggct tcggcgacct caacctcgat ttcgatctcg actgggcgc cctgagaat      1740
cccctggaca accccgacct gccgcgccgc gccgctgccg gcaaggcgga accggcggag     1800
gagccctgg cgttcgagag caatctccat gaactgccgg atgtcgccga gtacgaacac     1860
ctcgaactcg accagccaga gccggccacg gtgccgccgg aggaggcctc ggccagcctg     1920
gaccgggccc gcgcctgcat cgacagcggc gatctcgacc aggccagccg catcctgcgc     1980
ctggtggtgg cgcacggcga cccgtggcag aaggccgagg cgcgcgagtt gctggcactg     2040
atcgcctga                                                            2049
```

```
SEQ ID NO: 39          moltype = RNA  length = 2064
FEATURE                Location/Qualifiers
source                 1..2064
                       mol_type = transcribed RNA
                       organism = Pseudomonas aeruginosa
```

```
SEQUENCE: 39
atgtcctctt ccggcctttt cccttcccgt ccgctctggc ctctcacgcc actggcgctg      60
gcctgcctga tcgtttcggg ggaaacgctc ggcgccgacg gccgcccag cgaattgccc      120
tcccaggtga tcaccgccaa cccgctgggc aacgaatctc ccgccacgcc cagcagcgtg      180
ctcgaaggcg acgagctgac cctgcgacag aaaggcagcc tcggcgaaac cctcaacggc      240
ctgcccgggg tgtcctccac ctacttcgga ccgggcgcca gccgaccggt gatccgcggc      300
atggacggtg atcgcatccg cctgctgcgc aacggcgtcg gtgcgctcga cgcctcgtcg      360
ctgtcctacg accacgcggt gccggaagac cccaacagcg tcgagcgcct ggaagtggta      420
cgcggccgg ccgccctgct ctacggcggc aatgccatcg gcggggtggt gaacagcttc      480
gacaaccgca tccccagcga acccgtcgac ggcatccacg gcagcggcga actgcgctac      540
ggcggcgctgc acaccacccg tagccgctcc ggcgcactgg aggccggcga cggcaacttc     600
gccctgcacg tggacgccgc cagccgcgag ttcaacgacg tcaggattcc cggctacgcc      660
cattccagcc gccagcggca gatcgacggc gacaccggca agcatcgggt gcagaacagc      720
gacggccgcc aggacggcgg cgccgtcggt ggctcctatc actgggagca cggttacgcc      780
ggcctctcct acagcggcta cgacagcaac tatggctcgc cggccgcgg cgacgtgcgc      840
ctgaagatgc agcaggaccg ctacgccttc gcctccgaga tccgcgacct cgaaggcccg      900
ttcacctcgc tgaagctgga cgccgcctat accaagtacg agcacaagga aatcgaggac      960
ggcgagaccg gcaccacctt caagaacgaa ggctacgaag gccgcatcga ggcccgccac     1020
cgcccgctcg gcccgctgaa cggggtggtc ggcgcgcagt tcgccaacag ccgcttctcc     1080
gccctcggcg aggaagcctt cgtgccgcac acggaaaccg acagcgccgc gctgttcgcc     1140
ctggaggaat ggaagctcag cgaccgcctc gacctcagct tcggcgcccg cctggagcac     1200
acccgcgtgg accccgacgc caagggcaac gagcgcttcg ccgagaacga cggttcgcag     1260
agcttcacca ccggcagcct gtccaccggc gcggtgtaca agctgacgcc gatctggtcg     1320
ctggccgcca ccctcagcta caccgagcgc gccccgacct tctacgagct gtacgccaac     1380
ggtccgcacg ccgccaccgg tacctacgag gtaggcgatg ccgacgcgga caaggaaaag     1440
gcggtctcca ccgacctcgc cctgcgcttc gacaacggcg tgcacaaggg cagcgtcggg     1500
gtgttctaca gccgcttctc caactacatc ggcctgctcg ccacggtcg ccatcgcaac     1560
gaggaaggcg aagtggtcgc cgccggcgat gacgaggcgc tgccggaata cctctacagc     1620
ggcgttcgcg cggacttcta cggcgtcgag gcgcaggacc gcatccacct gctgaaagc     1680
ccgtacggca acttcgacct ggaactctcc ggggactaca cccgcgccaa gaacaaggac     1740
accggcgaac cgctgccacg catcgccccg ctgcgcctga acaccgcgct gatctgggag     1800
ttgcacgagt ggcaggcgcg ggtcgacgtc gaacacgccg cctcgcagca ccgcgtgccg     1860
gaggaagaac tctccaccga cggctacacc accctcggcg ccagcctcgg ctacaacttc     1920
gacctcggcg agagccgctg gctggccttc gtcaagggca ccaacctgac caaccagacc     1980
gtgcgctacg ccagttcgat cctgcgcgac cgggtgccgg cggcgggacg cggcatcgag     2040
gcgggggtga aggtggcgtt ctga                                           2064
```

```
SEQ ID NO: 40          moltype = RNA  length = 2412
FEATURE                Location/Qualifiers
source                 1..2412
                       mol_type = transcribed RNA
                       organism = Pseudomonas aeruginosa
```

```
SEQUENCE: 40
atgaggcaat cagctttcca ccatgcccgg cgtcgttggc ctgtactggg cgtggcgctg      60
ggcgcgctac tggtcgcggc gtgtagcgag acgccgaagg tccccggcgt gcccccggcc      120
gacgaggaag tcggtcggcc gctgagcagt gtccgctccg gtgcgccgtt gcgcagcgcc      180
gacgtccgcg agcggcccca ggccgagcag gcccgccgcg cgctgagtgc cggacgcggc      240
```

-continued

```
gtggcgcgct ccggtggcgt ggctccggtc tcagcgacag cggccgaact cggcgagcag   300
ccggtcagcc tgaatttcgt cgataccgag gtggaagcgg tggtgcgcgc gctgtcgcgc   360
gccaccggcc ggcagttcct ggtcgacccg cgggtgaagg gcaagctgac cctggtttcc   420
gaaggccagg tgccggcgcg caccgcctac cgcatgctca ccagcgccct gcgcatgcag   480
ggcttcagcg tggtcgacgt cgacggggtc agccaggtgg tgccggaggc tgccggccaag   540
ctgctcggcg ggccggtcta cggcgccgac cggccggcgg ccaacggcat ggtcacgcgg   600
accttccgcc tgcgctacga gaacgcggtg aacctgatcc cggtactgcg cccgatcgtc   660
gcgcagaaca acccgatcaa tgcctatccg gggaacaaca ccgtggtggt caccgactac   720
gcgcgaaaacc tcgatcgggt cgccgggatc atcgccagca tcgacatccc cagcgccagc   780
gacaccgacg tggtgccgat ccagaacggt atcgcggtgg acatcgccag caccgtctcc   840
gaactgctcg acagccaggg cagcggccggc gccgagcagg gccagaagac cgtggtgctc   900
gccgacccac gctccaacag catcgtgatc cgctcgccga gccccgagcg cacgcaattg   960
gcgcgcgacc tgatcggcaa gctggacagc gtgcaaagca atcccggcaa cctccatgtg   1020
gtctacttgc gcaacgccca ggcgacccgc ctggccaggg ccctgcgcgg gctgatcacc   1080
ggcgacagcg gcggcgaggg caacgagggc gaccagcagc gcgcgcgcct gagcggcggc   1140
ggcatgctcg gtggcggcaa cagcggtact ggtagccagg gcctggggag cagcggcaat   1200
accacgggca gcggttccag cgggttgggc ggcagcaacc gcagcggcgg cgcctatggt   1260
gcgatgggca gcggccaggg cggcgccgga cccggtcgga tgggcgagga gaactcggcg   1320
ttctccgccg gcgggggtaac cgtacaggcc gacgccacca ccaacaccct gctgatttcc   1380
gcacccgagc cgttgtaccg caacctccgc gaagtcatcg acctgctcga ccagcgccgc   1440
gcccaggtgg tgatcgaaag cctgatcgtc gaggtcagcg aagacgactc cagcgagttc   1500
ggcatccagt ggcaggccgg caacctcggc ggcaacgtcg tgttcggcgg ggtcaacttc   1560
ggccagtcgg cgctgaacac ggccggcaag aacaccatcg acgtgttgcc caaggggctc   1620
aacatcggcc tggtggatgg caccgtggac atccccggga tcggcaagat cctcgacctc   1680
aaggtgctcg cccgggcgct gaagagccgc ggcggcacca acgtcctgtc gaccccgaac   1740
ctgctgaccc tggacaacga gtcggcgagc atcatggcg gccagaccat accttcgtc   1800
agcggccagt acgtcaccga cggcggcggt accagcaaca acccgttcca gaccatccag   1860
cgcgaggacg tcggcctgaa gctgaacatc cgtccgcaga tctccgaggg aggaacggtc   1920
aagctcgacg tctaccagga ggtcagcagc gtcgacgagc gcgccagcac cgccgccggg   1980
gtggtcacca acaagcgcgc gatcgatacc agcatcctcc tcgacgacgg ccagatcatg   2040
gtcctcggcg gcctgttgca ggacaacgtg caggacaaca ccgacggcgt tcccggactc   2100
tccagcctcc ccggcgtcgg ctcgctgttc cgctaccaga agcgctcgcg gaccaagacc   2160
aacctgatgg tcttcctgcg tccctacatc gtccgcgacg ccgccgccgg ccgcagcatc   2220
accctcaacc gctacgactt catccgccgc gcccagcagc gcgtgcagcc gcgccacgac   2280
tggagcgtcg gcgacatgca ggctccggtg ctgccgccgg cgcagcaggg catcccgcag   2340
gccgcctacg acttgcgccc gagcccgcgg ccgctgcgcg cggtaccgtt gggcgaggcg   2400
gcgccgctat ga                                                        2412
```

```
SEQ ID NO: 41          moltype = RNA   length = 3489
FEATURE                Location/Qualifiers
source                 1..3489
                       mol_type = transcribed RNA
                       organism = Pseudomonas aeruginosa
SEQUENCE: 41
atgcgcctga agagcatcaa gctggcgggg ttcaagtcct tcgtcgatcc gaccacggtg   60
aacttcccca gcaacatggc ggcagtggta gggccgaacg gctgcggcaa gtcgaacatc   120
atcgacgcgg tgcgctgggt gatgggcgaa agctcggcga agaacctgcg cggcgagtcg   180
atgaccgatg tcatcttcaa cggctcgaat acccgcaagc cggtgagcca ggcgagcatc   240
gagctgatct tcgacaacgc cgagaccacc ctggtgggcg aatacgccca gtacgccgag   300
atatccattc gccggcgggt ctcgcgggat gggcagaaca cctatttcct caacggcacc   360
aagtgccggc ggcgcgacat caccgacatc ttcctcggca ccggcctggg gccgcgcaag   420
tactcgatca tcgaacaggg catgatcctc aagctgatcg aggcgcgtcc ggaagacctg   480
cgcaacttca tcgaggaagc cgcgggcatt tccaagtaca aggagcgccg ccgcgaaacc   540
gaaagccgca tccgtcggac ccaggaaaac ctggcacgcc tcaccgacct gcgcgaagag   600
ctggggcggc aactggaacg cctgcaccgg caggcccagt cggcggaaaa ataccaggaa   660
cacaaggccg aggagcgcca gctcaaggcc cagctggggtg ccgtgcgctg gcgcgcacctg   720
aacgagcagg tcggtcagcg cgagcgggtc atcggcgacc aggagatcgc cttcgaggcc   780
ctggtggccg agcagcgtgg tgccgatgcc ggcatcgaac ggctgcgcga cggccatcac   840
gagttgtccg aacgcttcaa ccaggtgcag gcacgcttct attcggtcgg cggcgacatc   900
gcccgggtcg agcagagcat ccagcatggc cagcagcgcc agcgccagtt gcaggacgac   960
ttgcgcgaag ccgaacggac ccgccaggaa accgaatcgc acctcgggca tgaccgtacc   1020
ttgctcgcga ccctggccga ggaaatggcc atgctcgcac cggaacagga actcagcgcg   1080
gccgccgcgc aagaagcggg catcgccctg gaacaggccg agcagggcat gcaggcctgg   1140
cagcagcagt gggatgcctt caaccagcag agcgccgaac cccgccgcca ggcagggcat   1200
cagcagtcgc gcatccagca cctggagcag agcctggagc gcctgcagga tcgcgagcgg   1260
cgcctgcagg aggagcgtgg ccagttggcg gccgaccccg aggacgcggc gatcctcgaa   1320
ctcaacgaac aggtggcgat cgccgaactg gccctgaag aactgcaatt gcaggagcag   1380
ggccaagccg agcgactcga acaattgcgc caggaattgc agcagctggc cgcgaacag   1440
caccaggccg agggcgagtt gcagcgcctg aacgggcgca tcgcttcgct ggaggccctg   1500
cagcaggccg ctctcgatcc cggacagggc gccttggagt ggttgcgcga caggccctg   1560
gaacaacgtc cgcgcctcgc cgaaggcttg cgtgtcgagc cgggttggga gctggcggtg   1620
gagaccgtgc tcgcgcgcgga tctgcaggcg gtcttgctgg acggcttcga cgggctcgcc   1680
ctggccggct tcggcaaggg cgagctgcgc ctgctcagcc ccgctcgcgg agccgcgacg   1740
gcggcggtt cgctgctgga caaggtccgc gccgacccg acctgagtcc ctggttggcc   1800
cgggtgaaac cggtggagac cctggaacag cgcgcacgccc agcgcggcgc cctgacgac   1860
ggcgagagc tgatcagtcg cgatggctac tgggtcggcg ggcacttcct gcgggtccgg   1920
cgcagcgacg aggcccaggg cggcatgctc gcccgcgccc aggaactgga ggcgttgcag   1980
gagcggcggg aggccctgga aacccgtgtc gccgaaggcg aggagcgtct ggctgcggcc   2040
cgcgacgagc agcgcgagct ggaaggcgcg cgggagcagg tgcggcgcca ggtccaggag   2100
```

```
gaggggcgcc ggcacggcga gctgaaggcg cagttgtccg cgcagcaggc caaggtcgag  2160
caactggtac tgcgtcgccg ccgtctcgac gaagaagtgg cggaactggc cgagcagcgc  2220
gcgctggaac aggagcaact gagcgaggcg cgcctgaccc tgcaggaagc gctggatagc  2280
atggcgctgg acaccgagcg ccgggaatcc ctgctggcgg agcgtgacgc cctgcgcgaa  2340
cggctcgacc ggattcgcca ggatgcccgc acccacaagg accatgcgca ccagttggcg  2400
gtgcgggtcg gctcgctgaa ggcgcagcac aattccaccc agcaggccct ggagcgcctc  2460
gaccagcagt cggcgcgcct caacgagcgt tgcgaacagc tcaacctcaa tctggaggag  2520
ggggcggcac cgctggaaga gctgcgcatg aagctcgagg agttgctgga gcggcggatg  2580
gccgtcgagg acgaactcaa gcaggcgcgg ctggccctga aagacgccga tcgcgaactg  2640
cgcgaggtgg agaagcgccg cggccaggcc gagcagcaat cgcaactgct gcgtggccag  2700
ctggagcagc agcgcctgga gtggcagggg ctggtggtgc ggcgcaaagc cttgcaggag  2760
cagctcgccg aagacggcta cgacctgcat acggtactgg ccaacctgcc cctggatgcc  2820
agcgaacgcg attgggagga gcgtctcgag agtctcgcgg cgcgcatcca gcgtctgggg  2880
ccgatcaacc tggcggcgat cgaggagtac cagcagcagt ccgagcgcaa gcgctacctg  2940
gactcgcaga acgacgacct ggccgaagcg ctggagacgc tggaaaacgt catccgcaag  3000
atcgaccggg aaacccgcaa tcgtttcaag gaaaccttcg accagatcaa tgctggcctt  3060
caggcattgt tcccgaaggt attcggcggc ggtacggcat atctggaact taccggcgaa  3120
gatctactcg ataccggtgt ggcgatcatg gcgcgcccgc cgggcaagaa gaacagcacc  3180
atccacttgt tgtccggcgg ggaaaaggcc ctgaccgcgc tggcgctggt attcgccatc  3240
ttccagttga acccggcgcc gttctgcatg ctcgacgaag tcgatgcgcc attggacgat  3300
gccaacgtcg gacgttatgc gcgattggtg aaggagatgt cggaaaaggt gcagttcatc  3360
tatatcaccc acaacaagat cgccatggaa atggccgatc agttgatggg cgtgaccatg  3420
catgagccgg gctgttcacg gcttgttgca gttgacgtgg aagaggcggt cgcattggct  3480
gaagcctga                                                          3489
```

```
SEQ ID NO: 42          moltype = RNA  length = 4254
FEATURE                Location/Qualifiers
source                 1..4254
                       mol_type = transcribed RNA
                       organism = Pseudomonas aeruginosa
SEQUENCE: 42
atgaacaaga gctatacgct ggtctggaac caggccacag gctgttggaa cgtcgcaagc    60
gaaggtaccc gtcggcgcag caagagcgga cgcggcaagg cgctcgtagt cgccggagcg   120
tcactgctcg gcctgttctg ccaggccccc gccttcgccc tgcccagcgg cgccacggtc   180
gtttcaggcg atgccggatt ccagacatcc accgatggcc ggcatatggt catcgaccag   240
cagagccaca agctgatcac caattggaac gagttcagcg tccgtgccga tgagcgggtc   300
agcttccacc agccggggcca ggacgccgtc gccctgaacc gggtgatcgg ccgcaacggc   360
agcgatatcc aggggcggat agatgccaac ggcaaggtct tcctggtcaa tcccaacggc   420
gtggtcttcg gcaagtccgc ccaggtcaac gtaggcggcc tggtggcttc caccctggac   480
ctggccgaca gggacttcct cgccggcaac taccagttcc ccggcgactc cggcgcaacc   540
gtaagcaatg ccggcagcct gcaagccagc gaaggcggca gcatcgccct gctgggcgcc   600
cgggtcagca acgacggctt gatccaggcg caactcggcg acgtggccct gggcgcaggc   660
cagggcatca acctcaattt cgacggcgac ggcctgctca acctgcaggt ggacaaggcc   720
tcggtcgacg ctctcgcaca caacggcggc ctcatccgcg ccgatggcgg ccaggtgctg   780
atgagcgccc gcagcgccga cagcctgctc aagaccgtcg tcaacaacca gggcactctc   840
gaggccagga cgctacgcag cgcggaagga cgcatcgtcc tcgacggcgg cgaacagggt   900
accgtcggca tggccggcaa gcaggacgcc agcgccatcg gcggaggcaa tggcggcctg   960
gtgctgaacc agggcgcgaa cgtcgagata cagcgaaccg cgcaggtgga cacccatgcc  1020
gaccagggcg caaccggcac ctggaggatt ctctcgcacg aggtcagcgt agccgctgtc  1080
ggccaggcaa acgctgccgg tgatggttcc ggccaggtcc atgtagcgca gggcccagcc  1140
ggggccaatg cgtccgatag caacggcgtg accatcgttc agcagcagcc ggccgtcgaa  1200
ctcgccgccg cgccaacggg tacctccgca gtgcagagcc agagcggcgc caacatcggc  1260
tcgggcgcca atggcatcag cgtcgtgcaa agccagaaca gcccaatat cggctcgggc   1320
gccaatggca tcagcgtcgt gcaaagccag aatggcgcca atatcggcgc cggcgcgagt  1380
ggcatcagcg tcgtgcagag ccagaacagc cccaacatcg gctcgggcgt caatggcgcg  1440
actgtcgtgc agagccagaa cggtgccaat atcggttcgg cgcaagtgg catcaccgtt   1500
gtgcaaagcc agaatggcgc aaatatcggt tcaggcgcga gtggcatcag cgtcgtgcag  1560
agccagagcg ccccagcat cggctcgggc gtcaatggcg tcacaatcgt gcagagccag    1620
agcggtgcca acatcggccc cggcgtcagc ggaatcgatg tcgtccagac ccagactctc  1680
cccaacctga gcccaggccgc caatggctcc agcatcgtcc aggtccagac gctaccgat   1740
atcgccgccg acgccggcaa tgtgcatgtc gtgcaggtcc agaccggcgg taacaaggtc  1800
ttcggcaact ccgccaccaa cgtcaggtca cgtaccgttc aggcccggag caacgagaat  1860
gtcggttccg gcctggcgaa tccaagcagc gcgggaaaag gctcgacgtt gcatgccgat  1920
accctggccc gcaaccttc cacaagcaac gtcgaagtgg tcgccacccg gggcaacgcc   1980
catgtcggcg cgccgctgtc ctgggacagc ggcaacggcc tgacgctaac cgccgagcgc  2040
ggggacctca ggatcaatgg cgcgctgacg gcccagggg aaaacgccag ccttactctc    2100
aatgccgggc agcgccctct ccgtatcgac gacagcctct ctctcactgg ccagggagcc  2160
cgggtcgaat tcaattcgga caagggttat gccctggccg aaggcacccg gatcaccctg  2220
tccggcaaga acgcaggatt ccgcgccaat gggcgggact acagcgtgat ccaggacctg  2280
cagcagttgc gcggcatcga tagggacctg ggcggcagct atgtcctcgg caatcgaatc  2340
gcaggcggca actccagctt cctgtcgata ggcaacgcga cgcgccttcgg cggtaccttc  2400
gacggcctgg gcaacaccat cgataatctc gccgtctacg gcaccggcgc ctactccggc  2460
ctgttcagcg tcaaccgggg cacccctccgc aacctgaacc tggaacgcat ttcgccgat   2520
ggagcacagg ccacccacta caatgtccag gtcggtagcg tccgtggccgt caacctcggt  2580
cgcatcgaca atgtgaacgc cagcgacatc cgtatcgccg cggcctcgaa gctgaacagc  2640
ctcggcgggc tggtcgcact gaacctgggt agtatcgaca acgccagcgc cagcggcacg  2700
ctggtcggca accgccacac ctatgctctg gcggactcg cagccgaaaa catcagcaca    2760
gccaggggc tggccagcat ctccaacagc cgggccgatt ttgccatctc cggccagttg    2820
aaggaccatg ccagccacta cggcgcgggg ggcctggtag gcaggaaccg cggcggcctc  2880
```

```
atccgcagca gcggcagtca gggaacgctg tcgctgagcg gtcacggaat gaacctggga    2940
ggactggtcg gatacagttc cgccggcgga ctggcggacg tttccgcctc cgtcgacgtc    3000
tcaggcaacg gacagcgcgg cctgtacggt gggctcatcg gcctcaacgt aaacagtggt    3060
attgcccacg ccacggccag cggcaaggtc cggggcacag acgcggaagc actgggcggg    3120
ctgatcggcc ggaacctgaa cgcggccatc aacaacgaca gcgcccatgg cgatgtcagc    3180
ctgcaagccg gtcgctacct gggaggcctg atcggccaca accaggcagg caacctggcc    3240
aacgtcagta ccagcggcaa cctgagtggt gggtcgctgc tccaggccgg cggcctgatc    3300
ggtctcaacg ccaatgcctc gctggtcaat gcctccgcca agggcaatgt cgctacccgc    3360
ggagcagaag cggttggcgg tctgctcgga gaaaacctgt acggctccgt catcaacggt    3420
tccgccagtg gcgaagtcac cgacggcagc ggcaaaacct gggtggcct gatagggtcc    3480
aacctcggcg gcaatcattc caacctgaag gcctccgggt gggtaaacgc aggggcgaac    3540
agtgacgtgg gagggctgat cggccacaac cggggcggca accacagcac cctggcggca    3600
tccggcaatg tcaccggggg caagggcagt cgcgtcggcg gactcgtcgg ctataacgat    3660
gccgcctcgc tgacgaacgt ctcggcttcg ggcaacgtca gcgccagtgg ttccagggcc    3720
atcggcgggt tgatcggcag tgacctgcga ggtcgctgaa tgctcgccag cagtcatgga    3780
atcgtgaacg acaagaccag ccacaacctg ggagggttgg tcggccgcgg tgaaaacacc    3840
tcgatccgct ccgccaaggc cagcggtgcg gtgagcggag gcgccgggat cagggccggc    3900
ggactggtcg gctccctgga gggctggcag gctctcatcc tgggggcctc ggccggcggc    3960
gatgtgacgg cgggctacga tagctatatt ggcgggctgg tgggcttcag caccgccacc    4020
atcagcggcg cttccgcttc cggcaaggtc ggaggctcgg tcgtctgggg cggcctggtc    4080
gcctggaacc aggggaatgt catgggttct tcggccagcg gcaggctgga gccacaaatc    4140
cccaaccaga tccatggcgg actgatcggc atcaattttg gctggcagtc ctggaactcg    4200
gtatacgggg ctgcggcgac cgttccaatg ataggtcgca actacaacct gtga          4254
```

```
SEQ ID NO: 43                  moltype = AA   length = 12
FEATURE                        Location/Qualifiers
REGION                         1..12
                               note = Rigid linker sequence
source                         1..12
                               mol_type = protein
                               organism = synthetic construct
SEQUENCE: 43
AEAAAKEAAA KA                                                              12

SEQ ID NO: 44                  moltype = AA   length = 135
FEATURE                        Location/Qualifiers
source                         1..135
                               mol_type = protein
                               organism = Pseudomonas aeruginosa
SEQUENCE: 44
MPRGDKSKYS DKQQRKAEHI EESYKAKGVS ESEAEARAWA TVNKQSGGGE RKGGSGRAKS        60
ETAKRADRKD SAHRAAQARS GRPANRGSAS RGKRQGSTSV SEMTREELMQ LARKRDIRGR        120
STMRKAELIE ALSRA                                                          135

SEQ ID NO: 45                  moltype = AA   length = 140
FEATURE                        Location/Qualifiers
source                         1..140
                               mol_type = protein
                               organism = Pseudomonas aeruginosa
SEQUENCE: 45
ATRRKTTPQE IDDIQDRMGS MRELDFDERR QARKARIGDE RPEAEVEAEF SSRRVREAGH        60
AGGQPDEDDG YQDNVGMDDL APETLIDESG ARSPAERGGE SPADKRLRVV HGNEIGAGHG        120
LDEAELARRD PLDGSSDEER                                                     140

SEQ ID NO: 46                  moltype = AA   length = 96
FEATURE                        Location/Qualifiers
source                         1..96
                               mol_type = protein
                               organism = Pseudomonas aeruginosa
SEQUENCE: 46
SFKQYNQNTI EIVGYTDSTG SRQHNMDLSQ RRAQSVAGYL TAQGVDGTRL STRGMGPDQP        60
IASNSTADGR AQNRRVEVNL RPVPGAQGPA QTQPQY                                   96

SEQ ID NO: 47                  moltype = AA   length = 377
FEATURE                        Location/Qualifiers
source                         1..377
                               mol_type = protein
                               organism = Pseudomonas aeruginosa
SEQUENCE: 47
CGWLWGPEGY FRDRGDDYLG ARETPPMQLP EGVHSKPLDP LLPIPLNVAT THEKEGEYEV        60
PRPQPLANAG DISDYSLQRS GDSRWVVAQR PPAEVWPVAR QFFEENGFRI ADERPQTGEF        120
SSDWQSLSQL SAPLARRLSS RVSGVEPDGQ ARVRVRIEPG VQSNTSEVYV LSQTRAAGDT        180
SSPSWPSKSV APSLDAALLD EMVASMARSA EQGGSVSLLA ANSIYDTPGT FELSKDGSGN        240
PVLTLQSDFD RSWVSVGRAL DNADIRVDDL NRSLGVYYVN IAEGAKKPDE DKPGFFSRLF        300
GGGEKTKEEE DAKAQRYQVR LTTVSDAVQV TVDKDINTSA PADVAQNVLE KLQESMRNAV        360
RGSGQRKPGQ FGLGEQF                                                        377

SEQ ID NO: 48                  moltype = AA   length = 639
FEATURE                        Location/Qualifiers
```

```
source                  1..639
                        mol_type = protein
                        organism = Pseudomonas aeruginosa
SEQUENCE: 48
MSFSSLGLSE ALARAVEAAG YSQPTPVQQR AIPAVLQGRD LMVAAQTGTG KTGGFALPVL    60
ERLFPAGHPD REHRHGPRQA RVLVLTPTRE LAAQVHDSFK VYARDLPLNS TCIFGGVGMN   120
PQIQALAKGV DVLVACPGRL LDLAGQNKVD LSHVEILVLD EADRMLDMGF IHDVKKVLAK   180
LPPKRQNLLF SATFSKDIVD LANKLLHNPE RIEVTPPNTT VERIEQRVFR LPAPQKRALL   240
AHLVTVGAWE QVLVFTRTKH GANRLAEYLT KHGLPAAAIH GNKSQNARTK ALADFKANDV   300
RILVATDIAA RGLDIDQLPH VVNYELPNVE EDYVHRIGRT GRAGRSGEAI SLVAPDEEKL   360
LKAIEKMTRQ RIPDGDAQGF DPEAVLPEVA QPEPREAPQK QPRRDKERRS SRERKPKDAQ   420
ASNPDSNVAA AQDGTEKPAG KRRRRGGKNK ENREAGQAQQ PRQSREARPA KPNRPPEVDG   480
NRDPEEFLDD DFDNFGNRAD YVSPYQGQEN KGRGRRGGQQ KPQGGTGQQG RGQGQGQARG   540
KSQGAAQGGA RGQGAGQGKA KKPRAGKPRG QGRENASRMS DAPLREPSEY GTGKQPSRQP   600
VVINKRDLVR MDRFPTAEQL DELEPRRKGE RPALLTRNR                          639

SEQ ID NO: 49          moltype = AA   length = 652
FEATURE                Location/Qualifiers
source                 1..652
                       mol_type = protein
                       organism = Pseudomonas aeruginosa
SEQUENCE: 49
SEPTTDAALI EKGRYVAQLG DCIACHTGPQ GAPMAGGLEL KTPMGTIYST NITPDRETGI    60
GRYSFEEFDR AMRKGVTAEG VNLYPAMPYP SYAKISEEDM RALYAYLMHG VQPVTQANTP   120
SAMSWPFNQR WGLSLWNWAF LDDAPFTPSS DADPVINRGA YLVQGLGHCG ACHTPRGIAF   180
QEKAMSEAGR SGQFYLAGET VEQWQALSLR NLWTVEDTVQ LLKTGQNRFA TVSGSMTDVI   240
HHSTQHFSDD DLLAIASYLK SLPAGKDDLP MPDSERPLAA PVDLYSSRGG LGYAQFCSDC   300
HRKDGSGVPG MFPPLAGNPT VASANPSTLL HITLTGWKTA QTATHSRVYT MPGFAQLEDR   360
EIAEILSFVR SSWGNQGSSI DAGQVKKLRQ RIEAGNGPAT TFVSPRLADM LAAPNAEQVV   420
RGMRLHLETR ELLPANVGNQ LHCTSCHLNA GTVADGSPPV GVSAFFPSYA PRAGKVIGLE   480
ERINGCFRRS MNGKPLPPDS ADMQAMVAYF DWMKNNTRPQ DKVAGRGVGK VDPALKPDPE   540
NGRKVYARQC VVCHGENGEG LRNSAGEMLF PPLWGDESFN IGAGMARTFT AAAFVKHNMP   600
IGFQERFPLG QGGLSDQDAV DVAEYFSHQP RPDFPDKIKD WPKDKRPLDA RY           652

SEQ ID NO: 50          moltype = AA   length = 456
FEATURE                Location/Qualifiers
REGION                 1..456
                       note = Fusion protein
source                 1..456
                       mol_type = protein
                       organism = synthetic construct
SEQUENCE: 50
GSSIDAGQVK KLRQRIEAGN GPATTFVSPR LADMLAAPNA EQVVRGMRLH LETRELLPAN    60
VGNQLHCTSC HLNAGTVADG SPFVGVSAFF PSYAPRAGKV IGLEERINGC FRRSMNGKPL   120
PPDSADMQAM VAYFDWMKNN TRPQDKVAGR GVGKVDPALK PDPENGRKVY ARQCVVCHGE   180
NGEGLRNSAG EMLFPPLWGD ESFNIGAGMA RTFTAAAFVK HNMPIGFQER FPLGQGGLSD   240
QDAVDVAEYF SHQPRPDFPD KIKDWPKDKR PLDARYAEAA AKEAAAKASE PTTDAALIEK   300
GRYVAQLGDC IACHTGPQGA PMAGGLELKT PMGTIYSTNI TPDRETGIGR YSFEEFDRAM   360
RKGVTAEGVN LYPAMPYPSY AKISEEDMRA LYAYLMHGVQ PVTQANTPSA MSWPFNQRWG   420
LSLWNWAFLD DAPFTPSSDA DPVINRGAYL VQGLGH                             456

SEQ ID NO: 51          moltype = AA   length = 311
FEATURE                Location/Qualifiers
source                 1..311
                       mol_type = protein
                       organism = Pseudomonas aeruginosa
SEQUENCE: 51
RRRREEAPVP AVEPKRRVAL NLPLRRAPRP PAAAPAPAKV EEQARPPVAA PSSPPPSPPP    60
APAAAPRAAM AAADKLDGAD IYIAYGRYGQ ARDLLRQVLA EQPQRLSARM KLLLVLAELG   120
DAAGFDALAE ETLASGGNPE AIDELRGRYP ALLQMPATET PAATTKDDDW SDLPLAESPV   180
LQQPDATSGA DGFGDLNLDL DLDWGALENP LDNPDLPRRA AAGKAEPAEE PLAFESNLHE   240
LPDVAEYEHL ELDQPEPATV PPEEASASLD RARACIDSGD LDQASRILRL VVAHGDPWQK   300
AEARELLALI A                                                       311

SEQ ID NO: 52          moltype = AA   length = 328
FEATURE                Location/Qualifiers
source                 1..328
                       mol_type = protein
                       organism = Pseudomonas aeruginosa
SEQUENCE: 52
LGVGDIILHS ALNQPLDADI ELLDVGDLGA DEIEVRLAGA DVFAAAGVER LQFLNELRFS    60
PVLQGRGGNR IHVSSIRPVQ EPYLNFLVEV ARPNGRIVRE FTVLLDPLGY TPRMLPAARS   120
GIEPQRQSST PVPAPRSAAV VVDPALLEPG DEYLARPSDN LWAISGRLRG AGNADRAQLM   180
EALYQLNPQA FVNADRHRLK AGARLRLPAG YQPERGAPGA VKEAAVEVLP PADAAVVENA   240
PAALVEAQRQ ADAEAEALAR QREELSQRMD DLQRQLQALQ EQLQQRDHQV AELQQQLARR   300
QAVRPAAPPP AAAAPSVAQP VETPTDSQ                                      328

SEQ ID NO: 53          moltype = AA   length = 379
FEATURE                Location/Qualifiers
```

```
REGION                   1..379
                         note = Fusion protein
source                   1..379
                         mol_type = protein
                         organism = synthetic construct
SEQUENCE: 53
ADGRPSELPS QVITANPLGN ESPATPSSVL EGDELTLRQK GSLGETLNGL PGVSSTYFGP   60
GASRPVIRGM DGDRIRLLRN GVGALDASSL SYDHAVPEDP NSVERLEVVR GPAALLYGGN  120
AIGGVVNSFD NRIPSEPVDG IHGSGELRYG GADTTRSRSG ALEAGDGNFA LHVDAASREF  180
NDVRIPGYAH SSRQAEAAAK EAAAKASGRH RNEEGEVVAA GDDEALPEYL YSGVRADFYG  240
VEAQDRIHLL ESPYGNFDLE LSGDYTRAKN KDTGEPLPRI APLRLNTALI WELQQWQARV  300
DVEHAASQHR VPEEELSTDG YTTLGASLGY NFDLGESRWL AFVKGTNLTN QTVRYASSIL  360
RDRVPAAGRG IEAGVKVAF                                              379

SEQ ID NO: 54            moltype = AA  length = 649
FEATURE                  Location/Qualifiers
REGION                   1..649
                         note = Fusion protein
source                   1..649
                         mol_type = protein
                         organism = synthetic construct
SEQUENCE: 54
SGRHRNEEGE VVAAGDDEAL PEYLYSGVRA DFYGVEAQDR IHLLESPYGN FDLELSGDYT   60
RAKNKDTGEP LPRIAPLRLN TALIWELQQW QARVDVEHAA SQHRVPEEEL STDGYTTLGA  120
SLGYNFDLGE SRWLAFVKGT NLTNQTVRYA SSILRDRVPA AGRGIEAGVK VAFAEAAAKE  180
AAAKAADGRP SELPSQVITA NPLGNESPAT PSSVLEGDEL TLRQKGSLGE TLNGLPGVSS  240
TYFGPGASRP VIRGMDGDRI RLLRNGVGAL DASSLSYDHA VPEDPNSVER LEVVRGPAAL  300
LYGGNAIGGV VNSFDNRIPS EPVDGIHGSG ELRYGGADTT RSRSGALEAG DGNFALHVDA  360
ASREFNDVRI PGYAHSSRQR QIDGDTGKHR VQNSDGRQDG GAVGGSYHWE HGYAGLSYSG  420
YDSNYGSPAE DDVRLKMQQD RYAFASEIRD LEGPFTSLKL DAAYTKYEHK EIEDGETGTT  480
FKNEGYEGRI EARHRPLGPL NGVVGAQFAN SRFSALGEEA FVPHTETDSA ALFALEEWKL  540
SDRLDLSFGA RLEHTRVDPD AKGNERFAEN DGSQSFTTGS LSTGAVYKLT PIWSLAATLS  600
YTERAPTFYE LYANGPHAAT GTYEVGDADA DKEKAVSTDL ALRFDNGVH              649

SEQ ID NO: 55            moltype = AA  length = 656
FEATURE                  Location/Qualifiers
source                   1..656
                         mol_type = protein
                         organism = Pseudomonas aeruginosa
SEQUENCE: 55
ADGRPSELPS QVITANPLGN ESPATPSSVL EGDELTLRQK GSLGETLNGL PGVSSTYFGP   60
GASRPVIRGM DGDRIRLLRN GVGALDASSL SYDHAVPEDP NSVERLEVVR GPAALLYGGN  120
AIGGVVNSFD NRIPSEPVDG IHGSGELRYG GADTTRSRSG ALEAGDGNFA LHVDAASREF  180
NDVRIPGYAH SSRQRQIDGD TGKHRVQNSD GRQDGGAVGG SYHWEHGYAG LSYSGYDSNY  240
GSPAEDDVRL KMQQDRYAFA SEIRDLEGPF TSLKLDAAYT KYEHKEIEDG ETGTTFKNEG  300
YEGRIEARHR PLGPLNGVVG AQFANSRFSA LGEEAFVPHT ETDSAALFAL EEWKLSDRLD  360
LSFGARLEHT RVDPDAKGNE RFAENDGSQS FTTGSLSTGA VYKLTPIWSL AATLSYTERA  420
PTFYELYANG PHAATGTYEV GDADADKEKA VSTDLALRFD NGVHKGSVGV FYSRFSNYIG  480
LLASGRHRNE EGEVVAAGDD EALPEYLYSG VRADFYGVEA QDRIHLLESP YGNFDLELSG  540
DYTRAKNKDT GEPLPRIAPL RLNTALIWEL QQWQARVDVE HAASQHRVPE EELSTDGYTT  600
LGASLGYNFD LGESRWLAFV KGTNLTNQTV RYASSILRDR VPAAGRGIEA GVKVAF      656

SEQ ID NO: 56            moltype = AA  length = 546
FEATURE                  Location/Qualifiers
REGION                   1..546
                         note = Fusion protein
source                   1..546
                         mol_type = protein
                         organism = synthetic construct
SEQUENCE: 56
GGTSNNPFQT IQREDVGLKL NIRPQISEGG TVKLDVYQEV SSVDERASTA AGVVTNKRAI   60
DTSILLDDGQ IMVLGGLLQD NVQDNTDGVP GLSSLPGVGS LFRYQKRSRT KTNLMVFLRP  120
YIVRDAAAGR SITLNRYDFI RRAQQRVQPR HDWSVGDMQA PVLPPAQQGI PQAAYDLRPS  180
PRPLRAVPLG EAAPLAEAAA KEAAAKAMRQ SAFHHARRRW PVLGVALGAL LVAACSETPK  240
VPGVPPADEE VGRPLSSVRS GAPLRSADVR ERPQAEQARR ALSAGRGVAR SGGVAPVSAT  300
AAELGEQPVS LNFVDTEVEA VVRALSRATG RQFLVDPRVK GKLTLVSEGQ VPARTAYRML  360
TSALRMQGFS VVDVDGVSQV VPEADAKLLG GPVYGADRPA ANGMVTRTFR LRYENAVNLI  420
PVLRPIVAQN NPINAYPGNN TVVVTDYAEN LDRVAGIIAS IDIPSASDTD VVPIQNGIAV  480
DIASTVSELL DSQGSGGAEQ GQKTVVLADP RSNSIVIRSP SPERTQLARD LIGKLDSVQS  540
NPGNLH                                                           546

SEQ ID NO: 57            moltype = AA  length = 1030
FEATURE                  Location/Qualifiers
source                   1..1030
                         mol_type = protein
                         organism = Pseudomonas aeruginosa
SEQUENCE: 57
GTGLGPRSYS IIEQGMISKL IEARPEDLRN FIEEAAGISK YKERRRETES RIRRTQENLA   60
RLTDLREELG RQLERLHRQA QSAEKYQEHK AEERQLKAQL GAVRWRDLNE QVGQRERVIG  120
```

-continued

```
DQEIAFEALV AEQRGADAGI ERLRDGHHEL SERFNQVQAR FYSVGGDIAR VEQSIQHGQQ  180
RQRQLQDDLR EAERTRQETE SHLGHDRTLL ATLAEEMAML APEQELSAAA AEEAGIALEQ  240
AEQGMQAWQQ QWDAFNQQSA EPRRQAEVQQ SRIQHLEQSL ERLQDRERRL QEERGQLAAD  300
PEDAAILELN EQVAIAELAL EELQLQEQGQ AERLEQLRQE LQQLAAEQHQ AQGELQRLNG  360
RIASLEALQQ AALDPGQGAL EWLREQGLEQ RPRLAEGLRV EPGWELAVET VLGADLQAVL  420
LDGFDGLALA GFGKGELRLL SPARGAATAA GSLLDKVRAD ADLSPWLARV KPVETLEQAL  480
AQRGALDDGE SLISRDGYWV GRHFLRVRRS DEAQGGMLAR AQELEALQER REALETRVAE  540
GEERLAAARD EQRELEGARE QVRRQVQEEG RRHGELKAQL SAQQAKVEQL VLRRRRLDEE  600
VAELAEQRAL EQEQLSEARL TLQEALDSMA LDTERRESLL AERDALRERL DRIRQDARTH  660
KDHAHQLAVR VGSLKAQHNS TQQALERLDQ QSARLNERCE QLNLNLEEGA APLEELRMKL  720
EELLERRMAV EDELKQARLA LEDADRELRE VEKRRGQAEQ QSQLLRGQLE QQRLEWQGLV  780
VRRKALQEQL AEDGYDLHTV LANLPLDASE RDWEERLESL AARIQRLGPI NLAAIEEYQQ  840
QSERKRYLDS QNDDLAEALE TLENVIRKID RETRNRFKET FDQINAGLQA LFPKVFGGGT  900
AYLELTGEDL LDTGVAIMAR PPGKKNSTIH LLSGGEKALT ALALVFAIFQ LNPAPFCMLD  960
EVDAPLDDAN VGRYARLVKE MSEKVQFIYI THNKIAMEMA DQLMGVTMHE PGCSRLVAVD 1020
VEEAVALAEA                                                       1030

SEQ ID NO: 58          moltype = AA  length = 1363
FEATURE                Location/Qualifiers
source                 1..1363
                       mol_type = protein
                       organism = Pseudomonas aeruginosa
SEQUENCE: 58
PSGATVVSGD AGFQTSTDGR HMVIDQQSHK LITNWNEFSV RADERVSFHQ PGQDAVALNR  60
VIGRNGSDIQ GRIDANGKVF LVNPNGVVFG KSAQVNVGGL VASTLDLADR DFLAGNYQFS  120
GDSGATVSNA GSLQASEGGS IALLGARVSN DGLIQAQLGD VALGAGQGIN LNFDGDGLLN  180
LQVDKGSVDA LAHNGGLIRA DGGQVLMSAR SADSLLKTVV NNQGTLEART LRSAEGRIVL  240
DGGEQGTVRV AGKQDASAIG GGNGGLVLNQ GANVEIQRTA QVDTHADQGA TGTWRILSHE  300
VSVAAVGQAN AAGDGSGQVH VAQGPAGANA SDSNGVTIVQ QQPAVDLAAG ANGTSAVQSQ  360
SGANIGSGAN GISVVQSQNS PNIGSGANGI SVVQSQNGAN IGAGASGISV VQSQNSPNIG  420
SGVNGVTVVQ SQNGANIGSG ASGITVVQSQ NGANIGSGAS GISVVQSQSG PSIGSGVNGV  480
TIVQSQSGAN IGPGVSGIDV VQTQTLPNLS PGANGSSIVQ VQTLPDIAAD AGNVHVVQVQ  540
TGGNKVFGNS ATNVRSRTVQ ARSNENVGSG LANPSSAGKG STLHADTLAR NLSTSNVEVV  600
ATRGNAHVGA PLSWDSGNGL TLTAERGDLR INGALTAQGE NASLTLNAGQ RPLRIDDSLS  660
LTGQGARVEF NSDKGYALAE GTRITLSGKN AGFRANGRDY SVIQDLQQLR GIDRDLGGSY  720
VLGNRIAGGN SSFLSIGNAS AFGGTFDGLG NTIDNLAVYG TGAYSGLFSV NRGTLRNLNL  780
ERISADGAQA THYNVQVGSL AAVNLGRIDN VNASDIRIAA ASKLNSLGGL VALNLGSIDN  840
ASASGTLVGN RHTYALGGLA AENISTARGV ASISNSRADF AISGQLKDHA SHYGAGGLVG  900
RNRGGLIRSS GSQGTLSLSG HGMNLGGLVG YSSAGGLADV SASVDVSGNG QRGLYGGLIG  960
LNVNSGIAHA TASGKVRGTD AEALGGLIGR NLNAAINNAS AHGDVSLQAG RYLGGLIGHN 1020
QAGNLANVST SGNLSGGSLL QAGGLIGLNA NASLVNASAK GNVATRGAEA VGGLLGENLY 1080
GSVINGSASG EVTDGSGKTL GGLIGSNLGG NHSNLKASGW VNAGANSDVG GLIGHNRGGN 1140
HSTLAASGNV TGGKGSRVGG LVGYNDAASL TNVSASGNVS ASGSRAIGGL IGSDLRGSLM 1200
LASSHGIVND KTSHNLGGLV GRGENTSIRS AKASGAVSGG AGIRAGGLVG SLEGWQALIL 1260
GASAGGDVTA GYDSYIGGLV GFSTATISGA SASGKVGGSG LLGGLVAWNQ GNVMGSSASG 1320
RLEPQIPNQI HGGLIGINFG WQSWNSVYGA AATVPMIGRH YNL                  1363

SEQ ID NO: 59          moltype = AA  length = 299
FEATURE                Location/Qualifiers
source                 1..299
                       mol_type = protein
                       organism = Pseudomonas aeruginosa
SEQUENCE: 59
PSGATVVSGD AGFQTSTDGR HMVIDQQSHK LITNWNEFSV RADERVSFHQ PGQDAVALNR  60
VIGRNGSDIQ GRIDANGKVF LVNPNGVVFG KSAQVNVGGL VASTLDLADR DFLAGNYQFS  120
GDSGATVSNA GSLQASEGGS IALLGARVSN DGLIQAQLGD VALGAGQGIN LNFDGDGLLN  180
LQVDKGSVDA LAHNGGLIRA DGGQVLMSAR SADSLLKTVV NNQGTLEART LRSAEGRIVL  240
DGGEQGTVRV AGKQDASAIG GGNGGLVLNQ GANVEIQRTA QVDTHADQGA TGTWRILSH   299

SEQ ID NO: 60          moltype = AA  length = 702
FEATURE                Location/Qualifiers
REGION                 1..702
                       note = Fusion protein
source                 1..702
                       mol_type = protein
                       organism = synthetic construct
SEQUENCE: 60
SGKVRGTDAE ALGGLIGRNL NAAINNASAH GDVSLQAGRY LGGLIGHNQA GNLANVSTSG  60
NLSGGSLLQA GGLIGLNANA SLVNASAKGN VATRGAEAVG GLLGENLYGS VINGSASGEV  120
TDGSGKTLGG LIGSNLGGNH SNLKASGWVN AGANSDVGGL IGHNRGGNHS TLAASGNVTG  180
GKGSRVGGLV GYNDAASLTN VSASGNVSAS GSRAIGGLIG SDLRGSLMLA SSHGIVNDKT  240
SHNLGGLVGR GENTSIRSAK ASGAVSGGAG IRAGGLVGSL EGWQALILGA SAGGDVTAGY  300
DSYIGGLVGF STATISGASA SGKVGGSGLL GGLVAWNQGN VMGSSASGRL EPQIPNQIHG  360
GLIGINFGWQ SWNSVYGAAA TVPMIGRHYN LAEAAAKEAA AKAPSGATVV SDAGFQTST   420
DGRHMVIDQQ SHKLITNWNE FSVRADERVS FHQPGQDAVA LNRVIGRNGS DIQGRIDANG  480
KVFLVNPNGV VFGKSAQVNV GGLVASTLDL ADRDFLAGNY QFSGDSGATV SNAGSLQASE  540
GGSIALLGAR VSNDGLIQAQ LGDVALGAGQ GINLNFDGDG LLNLQVDKGS VDALAHNGGL  600
IRADGGQVLM SARSADSLLK TVVNNQGTLE ARTLRSAEGR IVLDGGEQGT VRVAGKQDAS  660
AIGGGNGGLV LNQGANVEIQ RTAQVDTHAD QGATGTWRIL SH                    702
```

-continued

```
SEQ ID NO: 61          moltype = AA   length = 6
FEATURE                Location/Qualifiers
REGION                 1..6
                       note = Peptide linker
source                 1..6
                       mol_type = protein
                       organism = synthetic construct
SEQUENCE: 61
GSGGGA                                                            6

SEQ ID NO: 62          moltype = AA   length = 12
FEATURE                Location/Qualifiers
REGION                 1..12
                       note = Peptide linker
source                 1..12
                       mol_type = protein
                       organism = synthetic construct
SEQUENCE: 62
GSGGGAGSGG GA                                                     12

SEQ ID NO: 63          moltype = AA   length = 18
FEATURE                Location/Qualifiers
REGION                 1..18
                       note = Peptide linker
source                 1..18
                       mol_type = protein
                       organism = synthetic construct
SEQUENCE: 63
GSGGGAGSGG GAGSGGGA                                               18

SEQ ID NO: 64          moltype = AA   length = 24
FEATURE                Location/Qualifiers
REGION                 1..24
                       note = Peptide linker
source                 1..24
                       mol_type = protein
                       organism = synthetic construct
SEQUENCE: 64
GSGGGAGSGG GAGSGGGAGS GGGA                                        24

SEQ ID NO: 65          moltype = AA   length = 10
FEATURE                Location/Qualifiers
REGION                 1..10
                       note = Peptide linker
source                 1..10
                       mol_type = protein
                       organism = synthetic construct
SEQUENCE: 65
GENLYFQSGG                                                        10

SEQ ID NO: 66          moltype = AA   length = 12
FEATURE                Location/Qualifiers
REGION                 1..12
                       note = Peptide linker
source                 1..12
                       mol_type = protein
                       organism = synthetic construct
SEQUENCE: 66
KPEPKPAPAP KP                                                     12

SEQ ID NO: 67          moltype = AA   length = 8
FEATURE                Location/Qualifiers
REGION                 1..8
                       note = Peptide linker
source                 1..8
                       mol_type = protein
                       organism = synthetic construct
SEQUENCE: 67
SACYCELS                                                          8
```

The invention claimed is:

1. A pharmaceutical composition comprising an immunological adjuvant and a polypeptide, wherein the polypeptide comprises:

a) an amino acid sequence, which consists of residues 24-682 of SEQ ID NO: 10, or b) an amino acid sequence consisting of at least or exactly 35 contiguous amino acid residues from residues 24-682 of SEQ ID NO: 10, or c) an amino acid sequence having a sequence identity of at least 80% with the amino acid sequence of a) or with the amino acid sequence of b), wherein, said polypeptide is antigenic in a mammal, and wherein, the amino acid sequence comprises at least one amino acid residue selected from I corresponding to the I in position 30 in SEQ ID NO: 10;

V corresponding to the V in position 155 in SEQ ID NO: 10;

V corresponding to the V in position 163 in SEQ ID NO: 10;

S corresponding to the S in position 181 in SEQ ID NO: 10;

A corresponding to the A in position 226 in SEQ ID NO: 10;

P corresponding to the P in position 381 in SEQ ID NO: 10;

P corresponding to the P in position 510 in SEQ ID NO: 10;

S corresponding to the S in position 549 in SEQ ID NO: 10;

L corresponding to the L in position 569 in SEQ ID NO: 10; and

D corresponding to the D in position 570 in SEQ ID NO: 10.

2. The pharmaceutical composition according to claim 1, wherein the at least or exactly 35 contiguous amino acids are at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least ox exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least ox exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least ox exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly ox at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least: 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least of exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, or exactly or at most 658 contiguous amino acid residues.

3. The pharmaceutical composition according to claim 1, wherein the at least 35 contiguous amino acid residues has an N-terminal amino acid residue corresponding to any one of amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, and 668 in SEQ ID NO: 10 with the proviso that the selected amino acid residue satisfies the formula $N \le L\ n+1$, where N is the number of the selected residue, L is the number of amino acid residues in SEQ ID NO: 10, and n is the number of consecutive amino acid residues.

4. The pharmaceutical composition according to claim 1, wherein the polypeptide is fused or conjugated to an immunogenic carrier molecule, and/or which is fused directly or via a linker to a least one further polypeptide.

5. The pharmaceutical composition according to claim 4, wherein the immunogenic carrier molecule is polypeptide that induces T-helper lymphocyte responses in a majority of humans.

6. The pharmaceutical composition according to claim 1, comprising pharmaceutically acceptable carrier, vehicle or diluent.

7. The pharmaceutical composition according to claim 1, wherein the adjuvant is an aluminum based adjuvant.

8. The pharmaceutical composition according to claim 1, wherein the sequence identity with the amino acid sequence of a) or b) is at least 85%.

9. The pharmaceutical composition according to claim 1. wherein the sequence identity with the amino acid sequence of a) or b) is at least 90%.

10. The pharmaceutical composition according to claim 1, wherein the sequence identity with the amino acid sequence of a) or b) is at least 95%.

11. The pharmaceutical composition according to claim 4, wherein the linker is a polypeptide with SEQ ID NO: 43.

12. The pharmaceutical composition according to claim 5, wherein the polypeptide that induces T-helper lymphocyte response in a majority of humans is an immunogenic carrier protein elected from the group consisting of keyhole limpet hemocyanin or fragment thereof, tetanus toxoid or a fragment thereof, and diphtheria toxoid or a fragment thereof.

* * * * *